US006369267B1

(12) United States Patent
Toan et al.

(10) Patent No.: US 6,369,267 B1
(45) Date of Patent: Apr. 9, 2002

(54) POLYOXYALKYLENE SUBSTITUTED AND BRIDGED TRIAZINE, BENZOTRIAZOLE AND BENZOPHENONE DERIVATIVES AS UV ABSORBERS

(75) Inventors: Vien Van Toan, Rheinfelden (CH); Andreas Valet, Binzen (DE); Pascal Hayoz, Grolley (CH)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/679,231

(22) Filed: Oct. 4, 2000

Related U.S. Application Data

(62) Division of application No. 09/214,859, filed as application No. PCT/EP97/03567 on Jul. 7, 1997, now abandoned.

(30) Foreign Application Priority Data

Jul. 18, 1996 (CH) .............................................. 1806/96

(51) Int. Cl.$^7$ .................... C07D 251/24; C07D 249/18; C07C 409/213; C07C 69/035; C07C 233/08

(52) U.S. Cl. ....................... 560/144; 560/145; 564/152; 568/333

(58) Field of Search .......................... 568/333; 560/144, 560/145, 146; 564/152

(56) References Cited

U.S. PATENT DOCUMENTS 3,580,927 A 5/1971 Wear .......................... 568/333
3,843,371 A 10/1974 Piller et al. .................... 96/84
4,853,471 A 8/1989 Rody et al. ................. 548/261
5,210,195 A 5/1993 Lin et al. ..................... 546/190
5,322,868 A 6/1994 Valet et al. ................... 524/89
5,500,332 A 3/1996 Vishwakarma et al. ..... 430/512
5,571,924 A 11/1996 Kaplan et al. .............. 548/260
5,707,690 A * 1/1998 Valet et al. ................. 568/333

FOREIGN PATENT DOCUMENTS

| | | | |
|---|---|---|---|
| EP | 0434608 | | 6/1991 |
| EP | 0610861 | | 8/1994 |
| GB | 2273498 | | 6/1994 |
| JP | 7 109447 | * | 3/1995 |

OTHER PUBLICATIONS

Derwent Abstr. 95–128316/17 for JP 07053518.

* cited by examiner

*Primary Examiner*—Richard L. Raymond
*Assistant Examiner*—Venkataraman Balasubramanian
(74) *Attorney, Agent, or Firm*—Luther A. R. Hall; Tyler A. Stevenson

(57) ABSTRACT

Triazine, benzotriazole and benzophenone derivatives which are substituted or bridged with polyoxyalkylene groups, according to claim 1, and their use as UV absorbers, especially in photographic materials, in inks, including inkjet inks and printing inks, in transfer prints, in paints and varnishes, organic polymeric materials, plastics, rubber, glass, packaging materials, in sunscreens of cosmetic preparations and in skin protection compositions.

7 Claims, No Drawings

POLYOXYALKYLENE SUBSTITUTED AND BRIDGED TRIAZINE, BENZOTRIAZOLE AND BENZOPHENONE DERIVATIVES AS UV ABSORBERS

This application is a divisional of U.S. application Ser. No. 09/214,859 filed Jan. 13, 1999 now abandoned which is a 371 of PCT/EP97/03567.

The invention relates to novel polyoxyalkylene substituted and bridged triazine, benzotriazole and benzophenone derivatives, to their use in particular as UV absorbers, to compositions and materials, including coating compositions, comprising such polyoxyalkylene substituted and bridged triazine, benzotriazole and benzophenone derivatives, to the use of the coating compositions, and to material, especially organic material, which has been stabilized with the novel polyoxyalkylene substituted and bridged triazine, benzotriazole and benzophenone derivatives.

A range of triazine, benzotriazole and benzophenone derivatives which can be used inter alia as UV absorbers are already known. For example U.S. Pat. No. 3,843,371 describes certain hydroxyphenyltriazines and their use in photographic materials; certain 1,3,5-triphenyl-s-triazines, containing two free phenolic OH groups, which are substituted by a polyalkylene radical, are known from GB-A-2 273 498; certain bridged o-hydroxyphenyl-s-triazines, containing as bridge member a $—CH_2—CH(OH)—CH_2—O—CH_2—CH_2—O—CH_2—CH(OH)—CH_2—$ group, and their use as UV absorbers are known from U.S. Pat. No. 5,322,868; and certain o-hydroxyphenyl-s-triazines, bridged by an α,ω-butylenediol diglycidyl ether radical, are described in EP-A-0 434 608. Furthermore, U.S. Pat. No. 4,853,471 describes a number of 2-(2-hydroxyphenyl)benzotriazoles bridged by way of an α,ω-butylenediol diglycidyl ether radical and their use as UV absorbers, especially in plastics and in photographic materials, and U.S. Pat. No. 3,580,927 describes certain benzophenone derivatives bridged by way of an α,ω-butylenediol diglycidyl ether radical. However, none of these documents refers to triazine, benzotriazole or benzophenone derivatives bridged or substituted by an α,ω-alkanediol diglycidyl ether in which the alkane radical is interrupted one or more times by oxygen.

One of the objects of the invention, then, was to develop further compounds which can be used in particular as UV absorbers and which on the one hand are compatible with polymers and are dispersible in water and which on the other hand can also be used for water-based primers. The properties of a UV absorber are defined not only by the active centre, for example by the spectral properties of the UV-absorbing chromophore. Also of critical importance are those units of the molecule that are the primary determinants of ease of incorporation and mobility in the substrate and of compatibility with the substrate.

The achievement of this object lies in novel polyoxyalkylene substituted and bridged triazine, benzotriazole and benzophenone derivatives, which surprisingly respond very well to the requirements set out above—and set by industry—and which as UV absorbers cover a very wide range of applications.

The invention therefore provides polyoxyalkylene substituted and bridged triazine, benzotriazole and benzophenone derivatives, of the formulae $$A_1—L_1 \quad (I)$$

and $$A_1—L_2—A_1 \quad (II)$$

in which:

$A_1$ independently at each occurrence is a radical of the formula IIIA, IIIB or IIIC (IIIA)

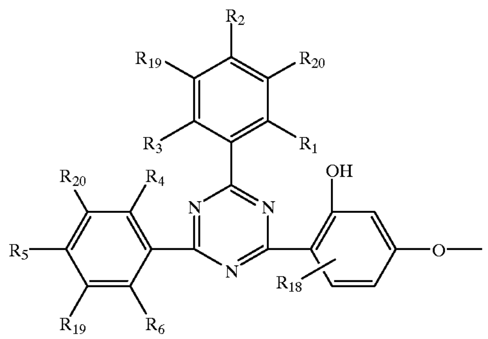

(IIIB)

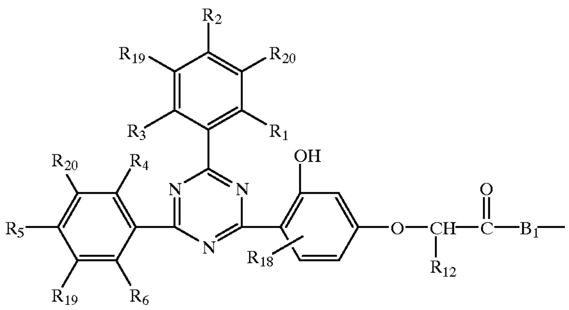

(IIIC)

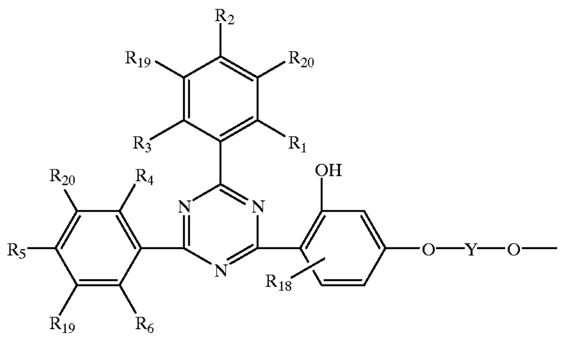

or a radical of the formulae IVA, IVB or IVC (IVA)

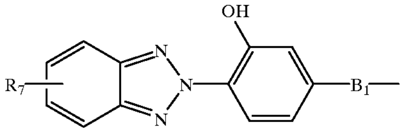

(IVB)

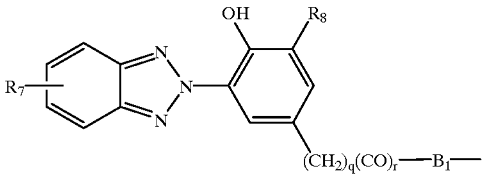

-continued (IVC)

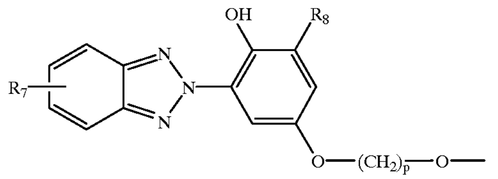

or a radical of the formula VA (VA)

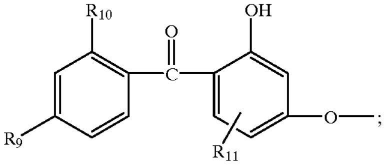

$B_1$ is the bridge member —O— or —NH—, $L_1$ is a polyoxyalkylene radical of the formula VI $$—CH_2—CH(OH)—CH_2—O—(CH_2—(CH_2)_u—O—)_m—D_1 \quad (VI)$$

in which $D_1$ is hydrogen,

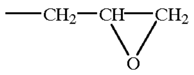

$—CH_2—CH(OH)—CH_2—OH$ or $R_{16}$;

or is a polyoxyalkylene radical of the formula VII $$—CO—(CH_2)_u—O—(CH_2—(CH_2)_u—O—)_m—D_2 \quad (VII)$$

in which $D_2$ is $—(CH_2)_u—CO—R_{13}$ or $R_{16}$;

or is a polyoxyalkylene radical of the formula VIII $$—Y—O—CO—(CH_2)_u—O—(CH_2—(CH_2)_u—O—)_m—D_3 \quad (VIII)$$

in which $D_3$ is $—(CH_2)_u—CO—R_{13}$ or $R_{16}$;

or is a polyoxyalkylene radical of the formula IX $$—(CH_2)_k—CH(R_{12})—CO—B_1—(C_nH_{2n}—O—)_m—C_nH_{2n}—B_1—D_4 \quad (IX)$$

in which $D_4$ is hydrogen or $R_{16}$;

or is a polyoxyalkylene radical of the formula X $$—CO—CH_2—CH_2—NH—(C_nH_{2n}—O—)_m—C_nH_{2n}—D_5 \quad (X)$$

in which $D_5$ is $—NH_2$, $—NH—(CH_2)_2—COO—R_{14}$ or $—O—R_{16}$;

or is a polyoxyalkylene radical of the formula XI $$—Y—O—CO—CH_2—CH_2—NH—(C_nH_{2n}—O—)_m—C_nH_{2n}—D_5 \quad (XI)$$

in which $D_5$ is as defined under formula (X);

or is a polyoxyalkylene radical of the formula XII $$—(C_nH_{2n}—O—)_m—C_nH_{2n}—D_6 \quad (XII)$$

in which $D_6$ is $—NH—CO—R_{15}$, $—OR_{16}$, OH or H;

or is a polyoxyalkylene radical of the formula XIII (XIII)

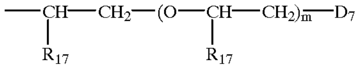

in which $D_7$ is $—OR_{16}$, $—NHCOR_{15}$ or $—OCH_2CH_2OR_{16}$;

$L_2$ is a polyoxyalkylene bridge member of the formula XIV $$—CH_2—CH(OH)—CH_2—O—(CH_2—(CH_2)_u—O—)_m—CH_2—CH(OH)—CH_2— \quad (XIV)$$

or is a polyoxyalkylene bridge member of the formula XV $$—CO—(CH_2)_u—O—(CH_2—(CH_2)_u—O—)_m—(CH_2)_u—CO— \quad (XV)$$

or is a polyoxyalkylene bridge member of the formula XVI $$—Y—O—CO(CH_2)_u—O—(CH_2—(CH_2)_u—O—)_m—(CH_2)_uCOO—Y— \quad (XVI)$$

or is a polyoxyalkylene bridge member of the formula XVII $$—(CH_2)_k—CH(R_{12})—CO—B_1—(C_nH_{2n}—O—)_m—C_nH_{2n}—B_1—CO—CH(R_{12})—(CH_2)_k— \quad (XVII)$$

or is a polyoxyalkylene bridge member of the formula XVIII (XVIII)

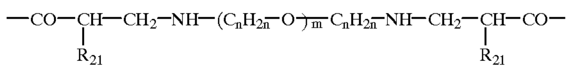

or is a polyoxyalkylene bridge member of the formula XIX $$—Y—O—CO—(CH_2)_2—NH—(C_nH_{2n}—O—)_m—C_nH_{2n}—NH—(CH_2)_2COO—Y— \quad (XIX)$$

or is a polyoxyalkylene bridge member of the formula XX $$—(C_nH_{2n}—O—)_m—C_nH_{2n}— \quad (XX)$$

or is a polyoxyalkylene bridge member of the formula XXI $$—CH(CH_3)—CH_2—(O—CH(CH_3)—CH_2)_a—(O—CH_2—CH_2)_b—(O—CH_2—CH(CH_3)_c— \quad (XXI)$$

in which: a+c=2.5 and b=8.5 to 40.5 or a+c=2 to 33 and b=0;

$R_1$, $R_2$, $R_3$, $R_4$, $R_5$ and $R_6$ independently of one another are: hydrogen, $C_1$–$C_{18}$alkyl, $C_3$–$C_6$alkenyl, halogen, $C_1$–$C_{18}$alkoxy, aryl, $C_1$–$C_{18}$alkoxyaryl, aryl-$C_1$–$C_4$alkyl, CN, $C_1$–$C_{18}$alkyl-S(O)$_t$ or aryl—S(O)$_t$;

$R_7$ is hydrogen, halogen, $C_1$–$C_4$alkyl, $C_1$–$C_8$alkoxy, $C_3$–$C_6$alkenoxy, $C_1$–$C_{18}$alkyl-S(O)$_t$ or aryl-S(O)$_t$;

$R_8$ is hydrogen, $C_1$–$C_{12}$alkyl, aryl-$C_1$–$C_4$alkyl or $C_5$–$C_{12}$cycloalkyl;

$R_9$ is hydrogen, halogen, $C_1$–$C_{18}$alkoxy, $C_3$–$C_6$alkenoxy or aryl-S(O)$_t$;

$R_{10}$ is hydrogen or OH;

$R_{11}$ is hydrogen, $C_1$–$C_{12}$alkyl, aryl-$C_1$–$C_4$alkyl or $C_3$–$C_6$alkenyl;

$R_{12}$ is hydrogen or $C_1$–$C_{16}$alkyl;

$R_{13}$ is halogen or $—O—R_{14}$;

$R_{14}$ is hydrogen, $C_1$–$C_8$alkyl, $C_3$–$C_6$alkenyl, aryl or aryl-$C_1$–$C_4$-alkyl;

$R_{15}$ is hydrogen, $C_1$–$C_{12}$alkyl or aryl;

$R_{16}$ is $C_1$–$C_{18}$alkyl, $C_5$–$C_{12}$cycloalkyl, $C_3$–$C_6$alkenyl, $C_1$–$C_{12}$alkylaryl or aryl-$C_1$–$C_4$alkyl;

$R_{17}$ is hydrogen or $C_1$–$C_4$alkyl;

$R_{18}$ is hydrogen, $C_1$–$C_{18}$alkyl, $C_3$–$C_6$alkenyl, $C_1$–$C_{18}$alkoxy, halogen or aryl-$C_1$–$C_4$alkyl;

$R_{19}$ and $R_{20}$ independently of one another are: hydrogen, $C_1$–$C_{18}$alkyl, $C_3$–$C_6$alkenyl, $C_1$–$C_{18}$alkoxy or halogen;

$R_{21}$ is hydrogen, $C_1$–$C_4$alkyl or CN;

Y is unsubstituted or substituted $C_2$–$C_{20}$alkylene;

k is zero or a number from 1–16, m is a number from 2–60, n is the numbers 2 to 6, p is a number from 2–12, q is a number from 1–6, r is zero or 1, t is zero, 1 or 2, and u is a number from 1–4.

$R_1$ to $R_6$, $R_{16}$ and $R_{18}$ to $R_{20}$ as $C_1$ to $C_{18}$alkyl are independently of one another, for example: an unbranched $C_1$–$C_{18}$alkyl radical, such as the methyl, ethyl, propyl, isopropyl, butyl, pentyl, hexyl, heptyl, octyl, nonyl, decyl, undecyl, dodecyl, tridecyl, tetradecyl, pentadecyl, hexadecyl, heptadecyl or octadecyl radical; a branched $C_1$–$C_{18}$alkyl radical, such as the sec-butyl, isobutyl, tert-butyl, 2-ethylbutyl, isopentyl, 1-methylpentyl, 1,3-dimethylbutyl, 1-methylhexyl, isoheptyl, 1,1,3,3-tetramethylbutyl, 1-methylheptyl, 3-methylheptyl, 2-ethylhexyl, 1,1,3-trimethylhexyl, 1,1,3,3-tetramethylpentyl, 1-methylundecyl or 1,1,3,3,5,5-hexamethylhexyl radical.

All these $C_1$ to $C_{18}$alkyl radicals are either unsubstituted or can be substituted one or more times.

$R_1$ to $R_6$, $R_{11}$, $R_{14}$, $R_{16}$ and $R_{18}$ to $R_{20}$ as $C_3$ to $C_6$alkenyl are independently of one another, for example: an unbranched or branched $C_3$ to $C_6$alkenyl radical such as, for example, the 2-propenyl- (=allyl), butenyl, 2-butenyl, 3-butenyl, isobutenyl, pentenyl, n-2,4-pentadienyl, hexenyl or 3-methyl-2-butenyl radical.

All these $C_3$–$C_6$alkenyl radicals are either unsubstituted or can be substituted one or more times.

If $R_1$ to $R_7$, $R_9$, $R_{13}$ or $R_{18}$ to $R_{20}$ is halogen, then it is in particular fluorine, chlorine, bromine or iodine.

$R_1$ to $R_6$, $R_9$ and $R_{18}$ to $R_{20}$ as a $C_1$–$C_{18}$alkoxy radical are independently of one another an unbranched or branched $C_1$–$C_{18}$alkoxy radical such as, for example, the methoxy, ethoxy, propoxy, isopropoxy, n-butoxy, isobutoxy, pentoxy, isopentoxy, hexyloxy, heptyloxy, octyloxy, decyloxy, dodecyloxy, tetradecyloxy, hexadecyloxy or octadecyloxy radical.

All these $C_1$–$C_{18}$alkoxy radicals are either unsubstituted or can be substituted one or more times.

If $R_1$ to $R_6$, $R_8$, $R_{11}$, $R_{14}$, $R_{16}$ or $R_{18}$ independently of one another are an aryl-$C_1$–$C_4$alkyl radical then this radical is, for example, a phenyl-$C_1$–$C_4$alkyl or naphthyl-$C_1$–$C_2$alkyl radical such as benzyl, α-methylbenzyl, α,α-dimethylbenzyl, 2-phenylethyl, 2-naphthylmethyl, 1-naphthylmethyl, 1-naphthylethyl or 2-naphthylethyl radical.

All these aryl-$C_1$–$C_4$alkyl radicals are either unsubstituted or substituted one or more times by, for example, $C_1$–$C_4$alkyl or $C_1$–$C_4$alkoxy.

If $R_1$ to $R_7$ independently of one another are a $C_1$–$C_{18}$alkyl-S(O)$_t$ radical then this is an unbranched or branched radical such as, for example, the methylthio, ethylthio, propylthio, isopropylthio, n-butylthio, isobutylthio, pentylthio, isopentylthio, hexylthio, heptylthio, octylthio, decylthio, dodecylthio, tetradecylthio, hexadecylthio or octadecylthio radical or the corresponding -sulfoxy or -sulfonyl radicals.

All these $C_1$–$C_{18}$alkyl-S(O)$_t$ radicals are either unsubstituted or substituted one or more times.

If $R_1$ to $R_7$ or $R_9$ is an aryl-S(O)$_t$ radical then it is, for example, the phenylthio, phenylsulfoxy or phenylsulfonyl radical.

If $R_7$, $R_{17}$ or $R_{21}$ is a $C_1$–$1C_4$alkyl radical then it is an unbranched or branched $C_1$–$C_4$-alkyl radical such as, for example, the methyl, ethyl, propyl, isopropyl, butyl, sec-butyl, isobutyl or tert-butyl radical; all these $C_1$–$C_4$alkyl radicals can be unsubstituted or substituted one or more times.

If $R_7$ is a $C_1$–$C_8$alkoxy radical then it is an unbranched or branched $C_1$–$C_8$alkoxy radical such as, for example, the methoxy, ethoxy, propoxy, isopropoxy, n-butoxy, isobutoxy, pentoxy, isopentoxy, hexyloxy, heptyloxy or octyloxy radical; all these $C_1$–$C_8$alkoxy radicals are either unsubstituted or substituted.

If $R_7$ or $R_9$ is a $C_3$–$C_6$alkenoxy radical then it is, in particular, the allyloxy radical.

If $R_8$, $R_{11}$, and $R_{15}$ independently of one another are a $C_1$–$C_{12}$alkyl radical then they are, for example: an unbranched $C_1$–$C_{12}$alkyl radical, such as the methyl, ethyl, propyl, isopropyl, butyl, pentyl, hexyl, heptyl, octyl, nonyl, decyl, undecyl or dodecyl radical, or a branched $C_1$–$C_{12}$alkyl radical, such as the sec-butyl, isobutyl, tert-butyl, 2-ethylbutyl, isopentyl, 1-methylpentyl, 1,3-dimethylbutyl, 1-methylhexyl, isoheptyl, 1,1,3,3-tetramethylbutyl, 1-methylheptyl, 3-methylheptyl, 2-ethylhexyl, 1,1,3-trimethylhexyl, 1,1,3,3-tetramethylpentyl, 1 -methylundecyl or 1,1,3,3,5,5-hexamethylhexyl radical.

All these $C_1$- to $C_{12}$alkyl radicals are unsubstituted or substituted one or more times by, for example, OH, $C_1$–$C_{18}$alkoxy, halogen, phenoxy (unsubstituted or substituent by $C_1$–$C_{18}$alkyl, $C_1$–$C_{18}$alkoxy or halogen), COOH, $CONH_2$, CONH($C_1$–$C_6$alkyl), CON($C_1$–$C_6$alkyl)$_2$, $NH_2$, NH($C_1$–$C_6$alkyl), N($C_1$–$C_6$alkyl)$_2$ or CN.

If $R_8$ and $R_{16}$ are a $C_5$–$C_{12}$cycloalkyl radical then they are, independently of one another, $C_5$–$C_{12}$cycloalkyl such as cyclopentyl, cyclohexyl, cycloheptyl, cyclooctyl, cyclononyl, cyclodecyl, cycloundecyl or cyclododecyl and mixed cycloalkyl/alkyl radicals with the corresponding number of carbon atoms, for example alkyl-substituted cycloalkyl, cydoalkyl-substituted alkyl or alkyl interrupted by cycloalkyl, for example methylcyclopentyl, dimethylcyclopentyl, methylcyclohexyl, dimethylcyclohexyl, trimethylcyclohexyl or tert-butylcyclohexyl; mention is also made, however, for example, of the $C_5$–$C_{12}$cycloalkyls which occur in naphthenic acid (see J. Buckingham, Dictionary of Organic Compounds, Vol. 4 page 4152, $5^{th}$ Edition (1982)).

If $R_{12}$ is a $C_1$–$C_{16}$alkyl radical or $R_{14}$ is a $C_1$–$C_8$alkyl radical, then reference is made to the corresponding $C_1$–$C_{18}$alkyls mentioned above in connection with $R_1$ to $R_6$.

If $R_{16}$ is a $C_1$–$C_{12}$alkylaryl radical then this means, in particular, the tolyl radical and tert-butylphenyl radical, which radicals can be substituted or unsubstituted.

Y as $C_2$–$C_{20}$alkylene is an unbranched or branched alkylene radical such as, for example, the di, tri, tetra, penta, hexa, hepta, octa, deca or dodecamethylene radical, the 2,2-dimethyl-prop-1,3-ylene radical, the 1,2-propylene radical or octadecamethylene radical.

These Y radicals can be unsubstituted or can be substituted one or more times by, for example, $C_1$–$C_{18}$alkoxy, $C_5$–$C_{12}$cycloalkoxy, phenoxy or phenyl-$C_1$–$C_4$alkoxy.

The aryl radical is, in particular, the phenyl, naphthyl or biphenyl radical.

In the preferred polyoxyalkylene substituted and bridged triazine, benzotriazole and benzophenone derivatives:

$R_1$, $R_3$, $R_4$ and $R_6$ independently of one another are hydrogen, $C_1$–$C_{18}$alkyl or phenyl or $C_1$–$C_{18}$alkoxyphenyl;

$R_2$ and $R_5$ independently of one another are hydrogen, $C_1$–$C_{18}$alkyl, halogen, $C_1$–$C_{18}$alkoxy or phenyl;

$R_7$ is hydrogen, halogen, $C_1$–$C_4$alkyl, $C_1$–$C_8$alkoxy or phenyl-S(O)$_t$;

$R_8$ is hydrogen, $C_1C_8$alkyl or phenyl-$C_1$–$C_3$alkyl;

$R_9$ is hydrogen, halogen, $C_1$–$C_{18}$alkoxy or phenyl-S(O)$_t$;

$R_{10}$ is hydrogen or OH;

$R_{11}$ is hydrogen, $C_1$–$C_8$alkyl, phenyl-$C_1$–$C_3$alkyl or allyl;

$R_{12}$ is $C_1$–$C_{10}$alkyl;

$R_{13}$ halogen or —O—$R_{14}$;

$R_{14}$ is hydrogen, $C_1$–$C_4$alkyl, allyl or phenyl;

$R_{15}$ is hydrogen, $C_1$–$C_7$alkyl or phenyl;

$R_{16}$ is $C_1$–$C_{12}$alkyl, cyclohexyl, allyl, $C_1$–$C_9$alkylphenyl or phenyl-$C_1$–$C_4$alkyl;

$R_{17}$ is hydrogen or $C_1$–$C_2$alkyl;

$R_{18}$ is hydrogen, $C_1$–$C_6$alkyl, allyl or chlorine;

$R_{19}$ and $R_{20}$ independently of one another are hydrogen, $C_1$–$C_{18}$alkyl, $C_1$–$C_{18}$alkoxy or halogen;

$R_{21}$ is hydrogen or methyl, especially hydrogen;

Y is unsubstituted or substituted $C_2$–$C_{12}$alkylene, m is the numbers 2 to 50, n is the numbers 2–4, p is the numbers 2 to 12, q is the numbers 1 to 6, k is zero or the numbers 1 to 6, t is zero or the numbers 1 or 2, u is the numbers 1 to 3.

Particular preference is given, however, to those novel polyoxyalkylene substituted and bridged triazine, benzotriazole and benzophenone derivatives in which:

$R_1$, $R_3$, $R_4$ and $R_6$ independently of one another are hydrogen or methyl;

$R_2$ and $R_5$ independently of one another are hydrogen, methyl, chlorine,.methoxy or phenyl;

$R_7$ is hydrogen, chlorine, methyl, methoxy or phenyl-S(O)$_t$;

$R_8$ is hydrogen, $C_1$–$C_4$alkyl or phenyl-$C_1$–$C_3$alkyl;

$R_9$ is hydrogen, chlorine, methoxy or phenyl-S(O)$_t$;

$R_{10}$ is hydrogen;

$R_{11}$ is hydrogen, $C_1$–$C_8$alkyl or phenyl-$C_1$–$C_3$alkyl;

$R_{12}$ is $C_1$–$C_{10}$alkyl;

$R_{13}$ is chlorine or —O—$R_{14}$;

$R_{14}$ is hydrogen, methyl, ethyl, allyl or phenyl;

$R_{15}$ is hydrogen, $C_1$–$C_5$alkyl or phenyl;

$R_{16}$ is $C_1$–$C_8$alkyl, cyclohexyl, allyl, $C_1$–$C_9$alkylphenyl or phenyl-$C_1$–$C_4$alkyl;

$R_{17}$ is hydrogen or $C_1$–$C_2$alkyl;

$R_{18}$ is hydrogen;

$R_{19}$ and $R_{20}$ independently of one another are hydrogen, methyl, methoxy or chlorine;

m is the numbers 2 to 23, n is the numbers 2 or 3, p is the numbers 2 or 3, and u is the number 1.

Of outstanding importance is a compound of the formula I or II, in which $B_1$ is —O— or —NH—;

$D_1$ has the meaning of $R_{16}$;

$D_6$ has the meaning H;

$D_7$ has the meaning —$OR_{16}$;

$L_1$ is a polyoxyalkylene radical of one of the formulae VI, XII and XIII;

$L_2$ is a polyoxyalkylene bridge member of one of the formulae XIV, XV, XVII, XVIII or XXI;

$R_1$ $R_3$, $R_4$ and $R_6$ independently of one another are hydrogen or $C_1$–$C_4$alkyl;

$R_2$ and $R_5$ independently of one another are hydrogen, $C_1$–$C_4$alkyl or phenyl;

$R_7$ is hydrogen, chlorine, methyl or methoxy;

$R_8$ is hydrogen or $C_1$–$C_4$alkyl;

$R_9$, $R_{10}$ and $R_{11}$ are hydrogen;

$R_{12}$ is hydrogen or methyl;

$R_{16}$ is $C_1$–$C_4$alkyl;

$R_{17}$ is hydrogen or methyl;

$R_{18}$, $R_{19}$ and $R_{20}$ and $R_{21}$ are hydrogen;

Y is $C_3$–$C_6$alkylene;

k is zero or 1, m is a number from 2–23, n is 2 to 3, p is 2, q is 2–4, r is zero or 1, and u is 1 to 3.

Among the novel polyoxyalkylene substituted triazine, benzotriazole and benzophenone derivatives, those of the formula I are of particular industrial interest; and of these, in particular, those compounds of the following formulae:

($IIIA_1$)

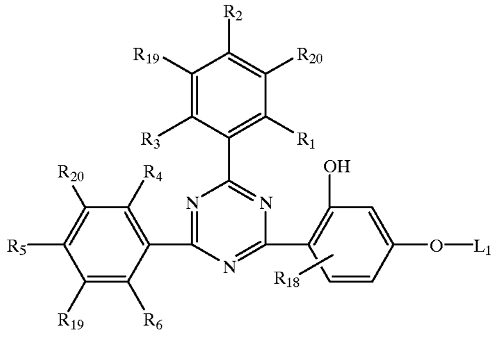

in which the symbols $R_1$, $R_2$, $R_3$, $R_4$, $R_5$, $R_6$, $R_{18}$, $R_{19}$ and $R_{20}$ are as defined at the outset, and $L_1$ is as defined under the formulae VI to XIII, for example VI to XI, especially those triazine derivatives of the formula $IIIA_1$, in which $L_1$ is as defined under the formulae VI to XI, but in particular those in which:

$R_1$, $R_4$, $R_{18}$, $R_{19}$ and $R_{20}$ are each hydrogen, $R_2$, $R_3$, $R_5$ and $R_6$ independently of one another are hydrogen, methyl or phenyl, and $L_1$ is the group of the formula $$-CH_2-CH(OH)-CH_2-O-(CH_2-CH_2-O-)_m-R_{16}$$

(derived from the formula (VI)) in which m is the numbers 2 to 23 and $R_{16}$ is $C_1$–$C_8$alkyl;

(IIIB$_1$)

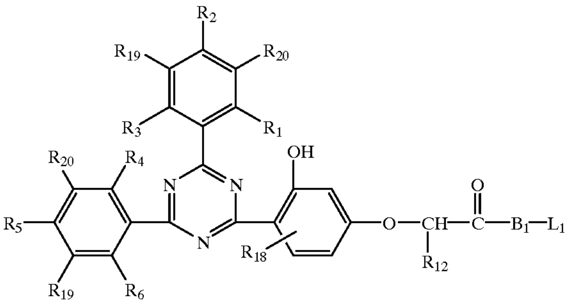

in which the symbols $R_1$, $R_2$, $R_3$, $R_4$, $R_5$, $R_6$, $R_{12}$, $R_{18}$, $R_{19}$, $R_{20}$ and $B_1$ are as defined above and $L_1$ is as defined under the formulae VI to XIII, especially those in which $L_1$ is as defined under the formulae XII and XIII, and in particular those in which:

$R_1$, $R_4$, $R_{18}$, and $R_{20}$ are each hydrogen, $R_2$, $R_3$, $R_5$ and $R_6$ independently of one another are hydrogen, methyl or phenyl, $R_{12}$ is methyl, and $L_1$ is the groups of the formulae $$-(CH_2-CH_2-O-)_m-OR_{16}$$

(derived from the formula (XII)) or

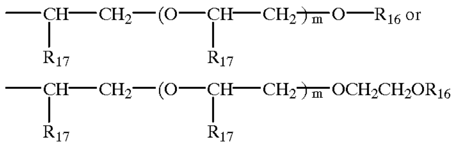

(derived from the formula (XIII) in which m is the numbers 2 to 23 and $R_{16}$ is $C_1$–$C_8$alkyl;

(IIIC$_1$)

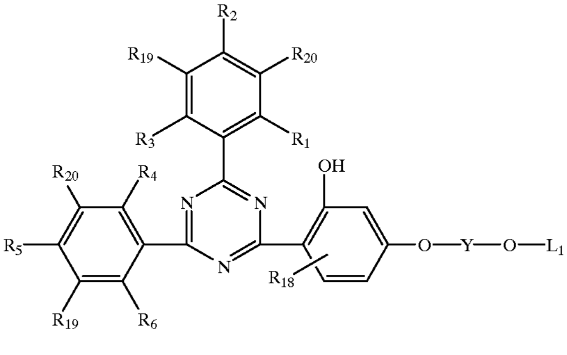

in which the symbols $R_1$, $R_2$, $R_3$, $R_4$, $R_5$, $R_6$, $R_{18}$, $R_{19}$, $R_{20}$ are as and Y are as defined at the outset, and $L_1$ is as defined under the formulae VI, VII and X, especially those in which:

$R_1$, $R_4$, $R_{18}$, $R_{19}$ and $R_{20}$ are each hydrogen, $R_2$, $R_3$, $R_5$ and $R_6$ independently of one another are hydrogen, methyl or phenyl, Y is unsubstituted or substituted, unbranched or branched $C_2$–$C_{12}$alkyl, and $L_1$ is as defined under the formulae VI, VII and X;

(IVA$_1$)

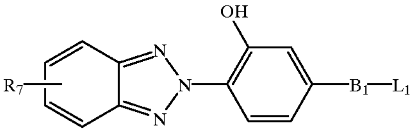

in which the symbols $R_7$ and $B_1$ are as defined at the outset, and $L_1$ is of the formulae VI to XIII, especially those in which $L_1$ is as defined under the formulae VI to XI, and in particular those in which:

$R_7$ is hydrogen or chlorine, and in which $L_1$ is of the formulae VI to XI;

(IVB$_1$)

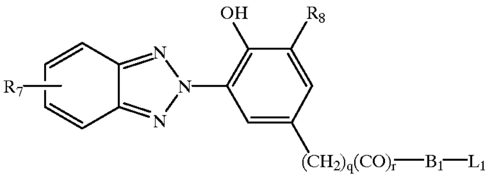

in which the symbols $R_7$, $R_8$, q, r and $B_1$ are as defined at the outset, and $L_1$ is of the formulae VI to XIII, especially those in which, if r=0, $L_1$ is as defined under the formulae VI to VIII and X and XI and, if r=1, $L_1$ is as defined under the formulae VI, VIII, IX, XII and XIII.

Very particularly preferred benzotriazole derivatives of the formula IVB$_1$ are those in which:

$R_7$ is hydrogen or chlorine, $R_8$ is tert-butyl, q is the number 2, r is the number 1, $B_1$ is oxygen, and in which $L_1$ is of the formulae VI to XIII, especially those in which:

$R_7$ is hydrogen or chlorine, $R_8$ is tert-butyl, q is the numbers 2–6, r is zero, $B_1$ is oxygen, and in which $L_1$ is of the formulae VI to XIII, or those in which $R_7$, $R_8$ and q are as defined, r is the number 1, $B_1$ is oxygen, and $L_1$ is as defined under the formulae VI, XII and XIII, or those in which $R_7$, $R_8$ and q are as defined at the outset, r is the number 1, $B_1$ is the —NH— group, and $L_1$ is of the formula XII or XIII, or those in which $R_7$, $R_8$ and q are as defined at the outset, r is zero, $B_1$ is oxygen, and $L_1$ is of the formulae VII and X;

($IVC_1$)

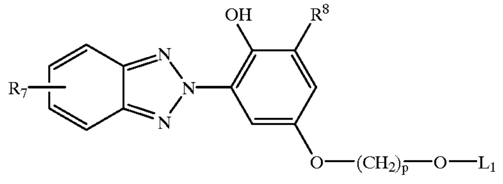

in which the symbol $R_7$, $R_8$ and p are as defined at the outset, and $L_1$ is of the formulae VI to XIII, or those in which $L_1$ is as defined under the formulae VI–VIII, X and XI, or those in which the symbols $R_7$, $R_8$ and p are as defined at the outset, and $L_1$ is of the formulae VII and X;

($VA_1$)

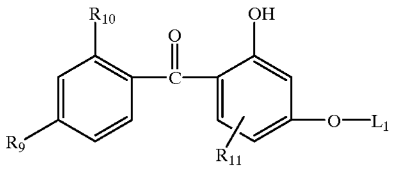

in which the symbols $R_9$, $R_{10}$ and $R_{11}$ are as defined at the outset and $L_1$ is of the formulae VI to XIII, or those in which $L_1$ is as defined under the formulae VI to XI, but especially those of the formulae $VA_1$ in which $R_9$, $R_{10}$ and $R_{11}$ are each hydrogen and $L_1$ is of the formulae VI to XIII.

Preferred polyoxyalkylene bridged triazine, benzotriazole and benzophenone derivatives which are of the formula II are in particular those of the formulae:

the symbols $R_1$, $R_2$, $R_3$, $R_4$, $R_5$, $R_6$, $R_{18}$, $R_{19}$ and $R_{20}$ are as defined at the outset and $L_2$ is as defined under the formulae XIV to XXI, especially those in which $L_2$ is as defined under the formulae XIV to XIX, or those in which the symbols $R_1$, $R_4$, $R_{18}$, $R_{19}$ and $R_{20}$ are each hydrogen, $R_2$, $R_3$, $R_5$ and $R_6$ independently of one another are hydrogen, methyl and phenyl, and $L_2$ is as defined under the formulae XIV to XXI, and then those in which $L_2$ is the following bridge members:

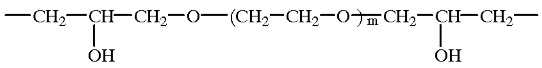 or (derived from the formula (XIV))

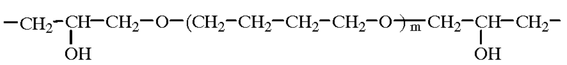

or (derived from the formula (XIV))

$$—CO—CH_2—O—(CH_2—CH_2—O—)_m—CH_2—CO—$$

(derived from the formula (XV)) in which "m" is the numbers 2 to 23;

($IIIA_2$)

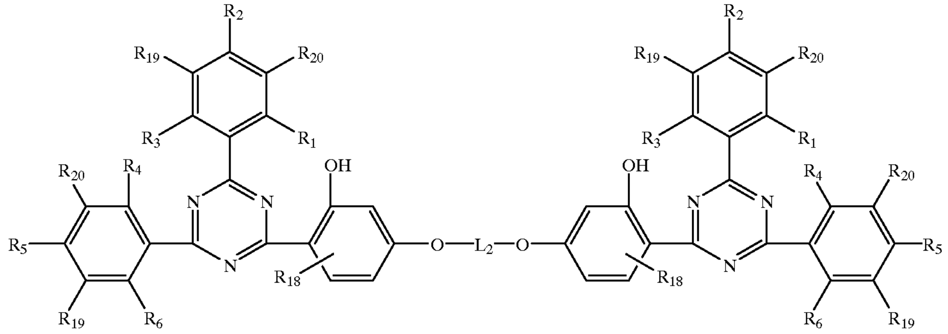

in which (IIIB$_2$)

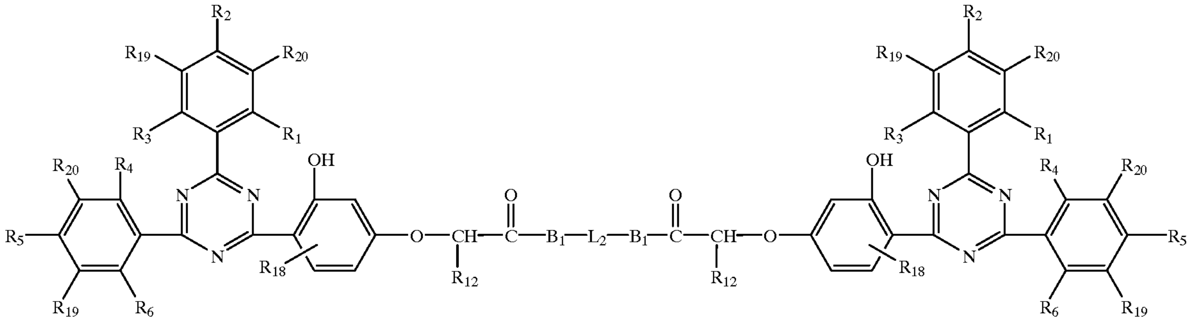

in which the symbols $R_1$, $R_2$, $R_3$, $R_4$, $R_5$, $R_6$, $R_{12}$, $R_{18}$, $R_{19}$, $R_{20}$ and $B_1$ are as defined at the outset and and $L_2$ is as defined under the formulae XIV to XXI, especially those in which $L_2$ is as defined under the formulae XX and XXI; but in particular those in which $R_1$, $R_4$, $R_{18}$, $R_{19}$ and $R_{20}$ are each hydrogen, $R_2$, $R_3$, $R_5$ and $R_6$ independently of one another are hydrogen, methyl and phenyl, $R_{12}$ is methyl, and $L_2$ is as defined under the formulae XX and XXI;

$L_2$ is the bridge member $$—CO—(CH_2)_u—O—(CH_2—(CH_2)_u—O—)_m—(CH_2)_u—CO— (XV),$$

or $$—CO—CH_2—CH_2—NH—(CH_2—CH_2—O—)_m—CH_2—CH_2—NH—CH_2—CH_2—CO—$$

or (derived from the formula (XVIII))

(IIIC$_2$)

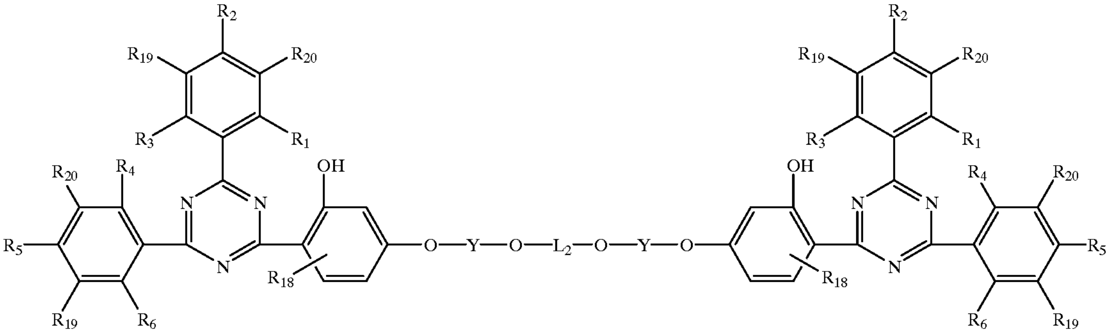

in which the symbols $R_1$, $R_2$, $R_3$, $R_4$, $R_5$, $R_6$, $R_{18}$, $R_{19}$, $R_{20}$ and Y are as defined at the outset and $L_2$ is as defined under the formulae XIV, XV and XVIII, especially those in which $R_1$, $R_4$, $R_{18}$, $R_{19}$ and $R_{20}$ are each hydrogen, $R_2$, $R_3$, $R_5$ and $R_6$ independently of one another are hydrogen, methyl and phenyl, Y is unsubstituted or substituted, unbranched or branched $C_2$–$C_{12}$alkylene, and

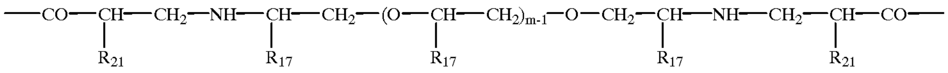

(derived from the formula (XVIII)) in which m is the numbers 2 to 50;

(IVA2)

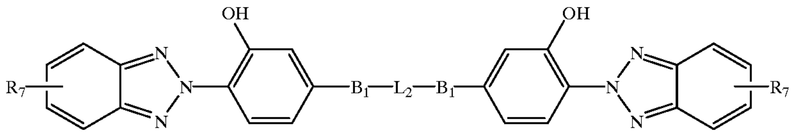

in which the symbols $R_7$ and $B_1$ are as defined at the outset and $L_2$ is as defined under the formulae XIV to XXI, especially those in which $L_2$ is as defined under the formulae XIV to XIX, and in particular those in which $R_7$ is hydrogen or chlorine, $B_1$=O and $L_2$ is of the formula $$—CH_2—CH(OH)—CH_2—O—(CH_2—CH_2—O—)_m—CH_2—CH(OH)—CH_2—$$

(derived from the formula (XIV)) in which m is the numbers 2 to 23;

q vis the number 2, r is the number 1, $B_1$ is the bridge member —NH—, and $L_2$ is the group of the formula $—(C_nH_{2n}—O—)_m—C_nH_{2n}—$ (XX) or $$—CH(CH_3)—CH_2—(O—CH(CH_3)—CH_2)_a—(O—CH_2—CH_2)_b—(O—CH_2—CH(CH_3)_c— \quad (XXI);$$

in which: a+c=2.5 and b=8.5 to 40.5 or a+c=2 to 33 and b=0, and also those in which $R_7$, $R_8$ and q are as defined at the outset, r is zero, $B_1$ is oxygen, and (IVB2)

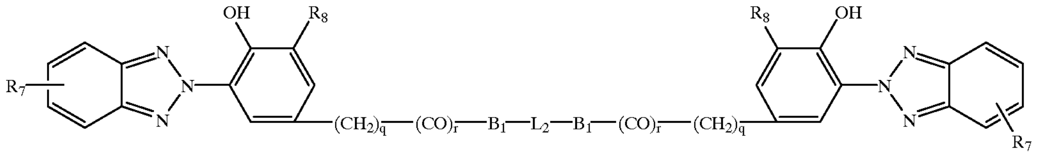

in which $R_7$, $R_8$, q, r and $B_1$ are as defined at the outset, and $L_2$ is of the formulae XIV to XXI, especially those in which, if r=0, $L_2$ is as defined under the formulae XIV, XV and XVIII and, if r=1, $L_2$ is as defined under the formulae XIV, XVI, XIX, XX and XXI.

Particular preference is given, however, to those benzotriazole derivatives of the formula $IVB_2$ in which $R_7$, $R_8$ and q are as defined at the outset, r is the number 1, $B_1$ is oxygen, and $L_2$ is of the formulae XIV, XVI, XIX and XX, or those in which $R_7$ is hydrogen or chlorine, $R_8$ is tert-butyl or hydrogen, q is the number 2, r is the number 1, $B_1$ is oxygen, and $L_2$ is of the formula $$—CH_2—CH(OH)—CH_2—O—(CH_2—CH_2—O—)_m—CH_2—CH(OH)—CH_2—$$

(derived from the formula (XIV)) in which m is the numbers 2 to 23, or those in which $R_7$ and $R_8$ are as defined at the outset, $L_2$ is of the formulae XV and XVIII or those in which $R_7$ is hydrogen or chlorine, $R_8$ is tert-butyl or hydrogen, q is the numbers 2 to 6, r is zero, $B_1$ is oxygen, and $L_2$ is of the formula $$—CO—CH_2—O—(CH_2—CH_2—O—)_m—CH_2—CO—$$

(derived from the formula (XV)) or (XVIII)

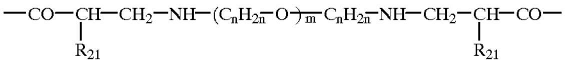

in which m is the numbers 2 to 23, or those in which if r=1, $L_2$ is as defined under the formulae XX and XXI, in which m is the numbers 2 to 50;

(IVC2)

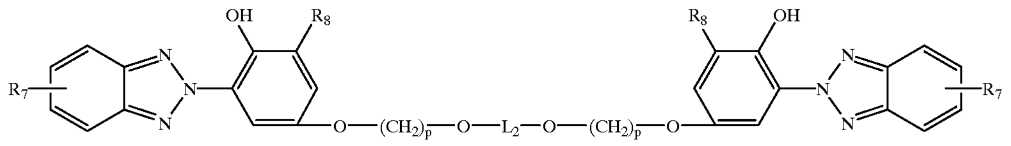

in which $R_7$, $R_8$ and p are as defined at the outset, and $L_2$ is of the formulae XIV, XV and XVIII, or those in which $R_7$, $R_8$ and p are as defined at the outset, and $L_2$ is of the formulae XV and XVIII; but in particular those in which $R_7$ is hydrogen, methyl or chlorine, $R_8$ is tert-butyl, p is the numbers 2 or 3, and $L_2$ is of the formula XV, in which m is the numbers 2 to 23;

(VA2)

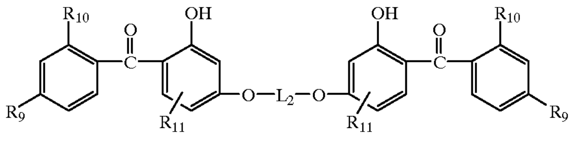

in which $R_9$, $R_{10}$ and $R_{11}$ are as defined at the outset, and $L_2$ is of the formulae XIV to XXI, or those in which $L_2$ is as defined under the formula XIV to XIX, or in which $R_9$, $R_{10}$ and $R_{11}$ are each hydrogen and $L_2$ is of the bridge member of the formula XIV, in which m is the numbers 2 to 23.

The novel, polyoxyalkylene substituted and bridged triazine, benzotriazole and benzophenone derivatives according to the invention are predominantly compounds of low volatility which in the case of compounds of the formula II can be preferably symmetrical (each $A_1$ 1 identical) or else asymmetrical (each $A_1$ different from the other).

The novel, polyoxyalkylene substituted and bridged triazine, benzotriazole and benzophenone derivatives according to the invention are used in particular as UV absorbers which serve to stabilize organic compounds that are light-sensitive, in a wide variety of products and materials.

In the narrower sense, UV absorbers are compounds which possess a pronounced absorption capacity for ultraviolet radiation, and are used in particular for improving light stability in a wide variety of materials in order, for example, to limit yellowing and embrittlement.

The novel, polyoxyalkylene substituted and bridged triazine, benzotriazole and benzophenone derivatives according to the invention can therefore be used with advantage as stabilizers for a wide variety of materials against damage thereto by light, oxygen and heat. The invention therefore also provides a process for stabilizing various materials against damage by light, oxygen and heat, by admixing with these materials at least one compound of the formula I and/or II, and for the use of these compounds as stabilizers for a wide variety of materials against damage by light, oxygen and heat.

Examples of materials sensitive to damage by light, oxygen and/or heat are photographic materials, inks, including inkjet inks and printing inks, transfer prints, paints and varnishes, organic polymeric materials, plastics, rubber, glass, packaging materials, sunscreens and skin protection compositions. Preferred uses are in coating materials, especially in water-based primer coating materials, for coatings.

The invention therefore additionally provides a composition comprising i) a material, especially an organic polymeric material, sensitive to damage by light, oxygen and/or heat, and ii) as stabilizer at least one polyoxyalkylene substituted and/or bridged triazine, benzotriazole and benzophenone derivative of the formula I and/or II.

Particular interest attaches to the use of the novel compounds of the formula I or II in organic polymeric materials as present, for example, in plastics, rubbers, coating materials or adhesives. Examples of materials to be stabilized in accordance with the invention are:

1. Polymers of monoolefins and diolefins, for example polypropylene, polyisobutylene, polybut-1-ene, poly-4-methylpent-1-ene, polyisoprene or polybutadiene, as well as polymers of cycloolefins, for instance of cyclopentene or norbornene, polyethylene (which optionally can be crosslinked), for example high density polyethylene (HDPE), high density and high molecular weight polyethylene (HDPE-HMW), high density and ultrahigh molecular weight polyethylene (HDPE-UHMW), medium density polyethylene (MDPE), low density polyethylene (LDPE), linear low density polyethylene (LLDPE), (VLDPE) and (ULDPE).

Polyolefins, i.e. the polymers of monoolefins exemplified in the preceding paragraph, preferably polyethylene and polypropylene, can be prepared by different, and especially by the following, methods:

a) radical polymerisation (normally under high pressure and at elevated temperature).

b) catalytic polymerisation using a catalyst that normally contains one or more than one metal of groups IVb, Vb, VIb or VIII of the Periodic Table. These metals usually have one or more than one ligand, typically oxides, halides, alcoholates, esters, ethers, amines, alkyls, alkenyls and/or aryls that may be either π- or σ-coordinated. These metal complexes may be in the free form or fixed on substrates, typically on activated magnesium chloride, titanium(III) chloride, alumina or silicon oxide. These catalysts may be soluble or insoluble in the polymerisation medium. The catalysts can be used by themselves in the polymerisation or further activators may be used, typically metal alkyls, metal hydrides, metal alkyl halides, metal alkyl oxides or metal alkyloxanes, said metals being elements of groups Ia, IIa and/or IIIa of the Periodic Table. The activators may be modified conveniently with further ester, ether, amine or silyl ether groups. These catalyst systems are usually termed Phillips, Standard Oil Indiana, Ziegler (-Natta), TNZ (DuPont), metalloceneor single site catalysts (SSC).

2. Mixtures of the polymers mentioned under 1), for example mixtures of polypropylene with polyisobutylene, polypropylene with polyethylene (for example PP/HDPE, PP/LDPE) and mixtures of different types of polyethylene (for example LDPE/HDPE).
3. Copolymers of monoolefins and diolefins with each other or with other vinyl monomers, for example ethylene/propylene copolymers, linear low density polyethylene (LLDPE) and mixtures thereof with low density polyethylene (LDPE), propylene/but-1-ene copolymers, propylene/isobutylene copolymers, ethylene/but-1-ene copolymers, ethylene/hexene copolymers, ethylene/methylpentene copolymers, ethylene/heptene copolymers, ethylene/octene copolymers, propylene/butadiene copolymers, isobutylene/isoprene copolymers, ethylene/alkyl acrylate copolymers, ethylenelalkyl methacrylate copolymers, ethylene/vinyl acetate copolymers and their copolymers with carbon monoxide or ethylene/acrylic acid copolymers and their salts (ionomers) as well as terpolymers of ethylene with propylene and a diene such as hexadiene, dicyclopentadiene or ethylidene-norbornene; and mixtures of such copolymers with one another and with polymers mentioned in 1) above, for example polypropylene/ethylene-propylene copolymers, LDPE/ethylene-vinyl acetate copolymers (EVA), LDPE/ethylene-acrylic acid copolymers (EAA), LLDPE/EVA, LLDPE/EAA and alternating or random polyalkylene/carbon monoxide copolymers and mixtures thereof with other polymers, for example polyamides.
4. Hydrocarbon resins (for example $C_5$–$C_9$) including hydrogenated modifications thereof (e.g. tackifiers) and mixtures of polyalkylenes and starch.
5. Polystyrene, poly(p-methylstyrene), poly(α-methylstyrene).
6. Copolymers of styrene or α-methylstyrene with dienes or acrylic derivatives, for example styrene/butadiene, styrene/acrylonitrile, styrene/alkyl methacrylate, styrene/butadiene/alkyl acrylate, styrene/butadiene/alkyl methacrylate, styrene/maleic anhydride, styrene/acrylonitrile/methyl acrylate; mixtures of high impact strength of styrene copolymers and another polymer, for example a polyacrylate, a diene polymer or an ethylene/propylene/diene terpolymer; and block copolymers of styrene such as styrene/butadiene/styrene, styrene/isoprene/styrene, styrene/ethylene/butylene/styrene or styrene/ethylene/propylene/ styrene.
7. Graft copolymers of styrene or α-methylstyrene, for example styrene on polybutadiene, styrene on polybutadiene-styrene or polybutadiene-acrylonitrile copolymers; styrene and acrylonitrile (or methacrylonitrile) on polybutadiene; styrene, acrylonitrile and methyl methacrylate on polybutadiene; styrene and maleic anhydride on polybutadiene; styrene, acrylonitrile and maleic anhydride or maleimide on polybutadiene; styrene and maleimide on polybutadiene; styrene and alkyl acrylates or methacrylates on polybutadiene; styrene and acrylontrile on ethylene/propylene/diene terpolymers; styrene and acrylonitrile on polyalkyl acrylates or polyalkyl methacrylates, styrene and acrylonitrile on acrylate/butadiene copolymers, as well as mixtures thereof with the copolymers listed under 6), for example the copolymer mixtures known as ABS, MBS, ASA or AES polymers.
8. Halogen-containing polymers such as polychloroprene, chlorinated rubbers, chlorinated and brominated copolymer of isobutylene-isoprene (halobutyl rubber), chlorinated or sulfochlorinated polyethylene, copolymers of ethylene and chlorinated ethylene, epichlorohydrin homo- and copolymers, especially polymers of halogen-containing vinyl compounds, for example polyvinyl chloride, polyvinylidene chloride, polyvinyl fluoride, polyvinylidene fluoride, as well as copolymers thereof such as vinyl chloride/vinylidene chloride, vinyl chloride/vinyl acetate or vinylidene chloride/vinyl acetate copolymers.
9. Polymers derived from α,β-unsaturated acids and derivatives thereof such as polyacrylates and polymethacrylates; polymethyl methacrylates, polyacrylamides and polyacrylonitriles, impact-modified with butyl acrylate.
10. Copolymers of the monomers mentioned under 9) with each other or with other unsaturated monomers, for example acrylonitrile/ butadiene copolymers, acrylonitrile/alkyl acrylate copolymers, acrylonitrile/alkoxyalkyl acrylate or acrylonitrilevinyl halide copolymers or acrylonitrile/alkyl methacrylate/butadiene terpolymers.
11. Polymers derived from unsaturated alcohols and amines or the acyl derivatives or acetals thereof, for example polyvinyl alcohol, polyvinyl acetate, polyvinyl stearate, polyvinyl benzoate, polyvinyl maleate, polyvinyl butyral, polyallyl phthalate or polyallyl melamine; as well as their copolymers with olefins mentioned in 1) above.
12. Homopolymers and copolymers of cyclic ethers such as polyalkylene glycols, polyethylene oxide, polypropylene oxide or copolymers thereof with bisglycidyl ethers.
13. Polyacetals such as polyoxymethylene and those polyoxymethylenes which contain ethylene oxide as a comonomer; polyacetals modified with thermoplastic polyurethanes, acrylates or MBS.
14. Polyphenylene oxides and sulfides, and mixtures of polyphenylene oxides with styrene polymers or polyamides.
15. Polyurethanes derived from hydroxyl-terminated polyethers, polyesters or polybutadienes on the one hand and aliphatic or aromatic polyisocyanates on the other, as well as precursors thereof.
16. Polyamides and copolyamides derived from diamines and dicarboxylic acids and/or from aminocarboxylic acids or the corresponding lactams, for example polyamide 4, polyamide 6, polyamide 6/6, 6/10, 6/9, 6/12, 4/6, 12/12, polyamide 1 1, polyamide 12, aromatic polyamides starting from m-xylene diamine and adipic acid; polyamides prepared from hexamethylenediamine and isophthalic or/and terephthalic acid and with or without an elastomer as modifier, for example poly-2,4,4,-trimethylhexamethylene terephthalamide or poly-m-phenylene isophthalamide; and also block copolymers of the aforementioned polyamides with polyolefins, olefin copolymers, ionomers or chemically bonded or grafted elastomers; or with polyethers, e.g. with polyethylene glycol, polypropylene glycol or polytetramethylene glycol; as well as polyamides or copolyamides modified with EPDM or ABS; and polyamides condensed during processing (RIM polyamide systems).
17. Polyureas, polyimides, polyamide-imides, polyetherimids, polyesterimids, polyhydantoins and polybenzimidazoles. 18. Polyesters derived from dicarboxylic acids and diols and/or from hydroxycarboxylic acids or the corresponding lactones, for example polyethylene terephthalate, polybutylene terephthalate, poly-1,4- dimethylolcyclohexane terephthalate and polyhydroxybenzoates, as well as block copolyether esters derived from hydroxyl-terminated polyethers; and also polyesters modified with polycarbonates or MBS.

19. Polycarbonates and polyester carbonates.
20. Polysulfones, polyether sulfones and polyether ketones.
21. Crosslinked polymers derived from aldehydes on the one hand and phenols, ureas and melamines on the other hand, such as phenol/formaldehyde resins, urea/formaldehyde resins and melamine/formaldehyde resins.
22. Drying and non-drying alkyd resins.
23. Unsaturated polyester resins derived from copolyesters of saturated and unsaturated dicarboxylic acids with polyhydric alcohols and vinyl compounds as crosslinking agents, and also halogen-containing modifications thereof of low flammability.
24. Crosslinkable acrylic resins derived from substituted acrylates, for example epoxy acrylates, urethane acrylates or polyester acrylates.
25. Alkyd resins, polyester resins and acrylate resins crosslinked with melamine resins, urea resins, isocyanates, isocyanurates, polyisocyanates or epoxy resins.
26. Crosslinked epoxy resins derived from aliphatic, cycloaliphatic, heterocyclic or aromatic glycidyl compounds, e.g. products of diglycidyl ethers of bisphenol A and bisphenol F, which are crosslinked with customary hardeners such as anhydrides or amines, with or without accelerators.
27. Natural polymers such as cellulose, rubber, gelatin and chemically modified homologous derivatives thereof, for example cellulose acetates, cellulose propionates and cellulose butyrates, or the cellulose ethers such as methyl cellulose; as well as rosins and their derivatives.
28. Blends of the aforementioned polymers (polyblends), for example PP/EPDM, Polyamide/EPDM or ABS, PVC/EVA, PVC/ABS, PVC/MBS, PC/ABS, PBTP/ABS, PC/ASA, PC/PBT, PVC/CPE, PVC/acrylates, POM/thermoplastic PUR, PC/thermoplastic PUR, POM/acrylate, POM/MBS, PPO/HIPS, PPO/PA 6.6 and copolymers, PAIHDPE, PA/PP, PN/PPO, PBT/PC/ABS or PBT/PET/PC.

The amount of the polyoxyalkylene substituted and bridged triazine, benzotriazole and benzophenone derivatives of the formula I or II added in accordance with the invention depends on the respective substrate and its intended use. In general, amounts of from 0.1 to 10.0% by weight are sufficient; it is preferred to use from 0.1 to 5 and, in particular, from 0.1 to 3% by weight, based on the polymer to be stabilized. In accordance with the invention, therefore, the polymers involved are in particular those comprising from 0.1 to 5% by weight, in particular from 0.1 to 3% by weight, of at least one compound of the formula I and/or II.

In certain cases it may be of advantage to use two or more of the novel compounds of the formula I or II.

The novel compositions may—in addition to the novel polyoxyalkylene substituted and bridged triazine, benzotriazole and benzophenone derivative of the formel I or II—also include other stabilizers or other additives, examples being antioxidants, further light stabilizers, metal passivators, phosphites or phosphonites. Examples of these are the following types of compounds:

1. Antioxidants 1.1. Alkylated monophenols, for example 2,6-di-tert-butyl-4-methylphenol, 2-tert-butyl-4,6-di-methylphenol, 2,6-di-tert-butyl-4-ethylphenol, 2,6-di-tert-butyl-4-n-butylphenol, 2,6-di-tert-butyl-4-isobutylphenol, 2,6-dicyclopentyl-4-methylphenol, 2- (α-methylcyclohexyl)-4,6-dimethylphenol, 2,6-dioctadecyl-4-methylphenol, 2,4,6-tricyclohexylphenol, 2 ,6-di-tert-butyl-4-methoxymethylphenol, nonylphenols which are linear or branched in the side chains, for example, 2,6-di-nonyl-4-methylphenol, 2,4-dimethyl-6-(1'-methylundec-1'-yl) phenol, 2,4-di-methyl-6-(1'-methylheptadec-1'-yl)phenol, 2,4-dimethyl-6-(1'-methyltridec-1'-yl)phenol and mixtures thereof.

1.2. Alkylthiomethylphenols, for example 2,4-dioctylthiomethyl-6-tert-butylphenol, 2,4-dioctylthiomethyl-6-methylphenol, 2,4-dioctylthiomethyl-6-ethylphenol, 2,6-di-dodecylthiomethyl-4-nonylphenol.

1.3. Hydroquinones and alkylated hvdroaquinones, for example 2,6-di-tert-butyl-4-methoxyphenol, 2,5-di-tert-butylhydroquinone, 2,5-di-tert-amylhydroquinone, 2,6-diphenyl-4-octadecyloxyphenol, 2,6-di-tert-butylhydroquinone, 2,5-di-tert-butyl-4-hydroxyanisole, 3,5-di-tert-butyl-4-hydroxyanisole, 3,5-di-tert-butyl-4-hydroxyphenyl stearate, bis-(3,5-di-tert-butyl-4-hydroxyphenyl) adipate.

1.4. Tocopherols, for example α-tocopherol, β-tocopherol, γ-tocopherol, δ-tocopherol and mixtures thereof (Vitamin E).

1.5. Hydroxylated thiodiphenyl ethers, for example 2,2'-thiobis(6-tert-butyl-4-methylphenol), 2,2'-thiobis(4-octylphenol), 4,4'-thiobis(6-tert-butyl-3-methylphenol), 4,4'-thiobis(6-tert-butyl-2-methylphenol), 4,4'-thiobis-(3,6-di-sec-amylphenol), 4,4'-bis(2,6-dimethyl-4-hydroxyphenyl)disulfide.

1.6. Alkylidenebisphenols, for example 2,2'-methylenebis(6-tert-butyl-4-methylphenol), 2,2'-methylenebis(6-tert-butyl-4-ethylphenol), 2,2'-methylenebis[4-methyl-6-(α-methylcyclohexyl)-phenol], 2,2'-methylenebis(4-methyl-6-cyclohexylphenol), 2,2'-methylenebis(6-nonyl-4-methylphenol), 2,2'-methylenebis(4,6-di-tert-butylphenol), 2,2'-ethylidenebis(4,6-di-tert-butylphenol), 2,2'-ethylidenebis(6-tert-butyl-4-isobutylphenol), 2,2'-methylenebis[6-(α-methylbenzyl)-4-nonylphenol], 2,2'-methylenebis[6-(α,α-dimethylbenzyl)-4-nonylphenol], 4,4'-methylenebis(2,6-di-tert-butylphenol), 4,4'-methylenebis(6-tert-butyl-2-methylphenol), 1,1-bis(5-tert-butyl-4-hydroxy-2-methylphenyl)butane, 2,6-bis(3-tert-butyl-5-methyl-2-hydroxybenzyl)-4-methylphenol, 1,1,3-tris(5-tert-butyl-4-hydroxy-2-methylphenyl)butane, 1,1 -bis(5-tert-butyl-4-hydroxy-2-methyl-phenyl)-3-n-dodecylmercaptobutane, ethylene glycol bis[3,3-bis(3'-tert-butyl-4'-hydroxyphenyl)butyrate], bis(3-tert-butyl-4-hydroxy-5-methyl-phenyl)dicyclopentadiene, bis[2-(3'-tert-butyl-2'-hydroxy-5'-methylbenzyl)-6-tert-butyl-4-methylphenyl]terephthalate,r 1,1-bis-(3,5-dimethyl-2-hydroxyphenyl)butane, 2,2-bis-(3,5-di-tert-butyl-4-hydroxyphenyl)propane, 2,2-bis-(5-tert-butyl-4-hydroxy2-methylphenyl)-4-n-dodecylmercaptobutane, 1,1,5,5-tetra-(5-tert-butyl-4-hydroxy-2-methylphenyl) pentane.

1.7. O—, N— and S-benzyl compounds, for example 3,5,3',5'-tetra-tert-butyl-4,4'-dihydroxydibenzyl ether, octadecyl-4-hydroxy-3,5-dimethylbenzylmercaptoacetate, tridecyl-4-hydroxy-3,5-di-tert-butylbenzylmercaptoacetate, tris(3,5-di-tert-butyl-4-hydroxybenzyl)amine, bis(4-tert-butyl-3-hydroxy-2,6-dimethylbenzyl)dithioterephthalate, bis(3,5-di-tert-butyl-4-hydroxybenzyl)sulfide, isooctyl-3,5-di-tert-butyl-4-hydroxybenzylmercaptoacetate.

1.8. Hydroxybenzylated malonates, for example dioctadecyl-2,2-bis-(3,5-di-tert-butyl-2-hydroxybenzyl)-malonate, di-octadecyl-2-(3-tert-butyl-4-hydroxy-5-methylbenzyl)-malonate, di-dodecylmercaptoethyl-2,2-bis-(3,5-di-tert-butyl-4-hydroxybenzyl)malonate, bis[4-(1,1,3,3-tetramethylbutyl)phenyl]-2,2-bis(3,5-di-tert-butyl-4-hydroxybenzyl)malonate.

1.9. Aromatic hydroxybenzyl compounds, for example 1,3,5-tris-(3,5-di-tert-butyl-4-hydroxybenzyl)-2,4,6-trimethylbenzene, 1,4-bis(3,5-di-tert-butyl-4-hydroxybenzyl)-2,3,5,6-tetramethylbenzene, 2,4,6-tris(3,5-di-tert-butyl-4-hydroxybenzyl)phenol.

1.10. Triazine Compounds, for example 2,4-bis(octylmercapto)-6-(3,5-di-tert-butyl-4-hydroxyanilino)-1,3,5-triazine, 2-octylmercapto-4,6-bis(3,5-di-tert-butyl-4-hydroxyanilino)-1,3,5-triazine, 2-octylmercapto-4,6-bis(3,5-di-tert-butyl-4-hydroxyphenoxy)-1,3,5-triazine, 2,4,6-tris(3,5-di-tert-butyl-4-hydroxyphenoxy)- 1,2,3-triazine, 1,3,5-tris-(3,5-di-tert-butyl-4-hydroxybenzyl) isocyanurate, 1,3,5-tris(4-tert-butyl-3-hydroxy-2,6-dimethyl benzyl)isocyanurate, 2,4,6-tris(3,5-di-tert-butyl-4-hydroxyphenylethyl)-1,3,5-triazine, 1,3,5-tris(3,5-di-tert-butyl-4-hydroxyphenylpropionyl)-hexahydro-1,3,5-triazine, 1,3,5-tris(3,5-dicyclohexyl-4-hydroxybenzyl) isocyanurate.

1.11. Benzylphosphonates, for example dimethyl-2,5-di-tert-butyl-4-hydroxybenzylphosphonate, diethyl-3,5-di-tert-butyl-4-hydroxybenzylphosphonate, dioctadecyl3,5-di-tert-butyl-4-hydroxybenzylphosphonate, dioctadecyl-5-tert-butyl-4-hydroxy-3-methylbenzylphosphonate, the calcium salt of the monoethyl ester of 3,5-di-tert-butyl-4-hydroxybenzylphosphonic acid.

1.12. Acylaminophenols, for example 4-hydroxylauranilide, 4-hydroxystearanilide, octyl N-(3,5-di-tert-butyl-4-hydroxyphenyl)carbamate.

1.13. Esters of β-(3,5-di-tert-butyl-4-hydroxyphenyl) propionic acid with mono- or polyhydric alcohols, e.g. with methanol, ethanol, n-octanol, i-octanol, octadecanol, 1 ,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1 -phospha-2,6,7-trioxabicyclo[2.2.2] octane.

1.14. Esters of β-(5-tert-butyl-4-hydroxy-3-methylphenyl) propionic acid with mono- or poly-hydric alcohols, e.g. with methanol, ethanol, n-octanol, i-octanol, octadecanol, 1,6 -hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.15. Esters of β-(3,5-dicyclohexyl-4-hydroxyphenyl) propionic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl)isocyanurate, N,N'-bis(hydroxyethyl) oxamide, 3-thiaundecanol, 3-thiapentadecanol, trimethylhexanediol, trimethylolpropane, 4-hydroxymethyl-1-phospha-2,6,7-trioxabicyclo[2.2.2] octane.

1.16. Esters of 3,5-di-tert-butyl-4-hydroxyphenyl acetic acid with mono- or polyhydric alcohols, e.g. with methanol, ethanol, octanol, octadecanol, 1,6-hexanediol, 1,9-nonanediol, ethylene glycol, 1,2-propanediol, neopentyl glycol, thiodiethylene glycol, diethylene glycol, triethylene glycol, pentaerythritol, tris(hydroxyethyl) isocyanurate, N,N'-bis(hydroxyethyl)oxamide, 3-thiaundecanol, 3-thiapentadecanol, trimethylhexanediol, trimethylolpropane, 4-hydroxymethyl- 1-phospha-2,6,7-trioxabicyclo[2.2.2] octane.

1.17. Amides of β-(3,5-di-tert-butyl-4-hydroxyphenyl) propionic acid e.g. N,N'-bis(3,5-di-tert-butyl-4-hydroxyphenylpropionyl)hexamethylenediamide, N,N'-bis(3,5-di-tert-butyl-4-hydroxyphenylpropionyl) trimethylenediamide, N,N'-bis(3,5-di-tert-butyl-4-hydroxyphenylpropionyl)hydrazide, N,N'-bis[2-(3-[3,5-di-tert-butyl-4-hydroxyphenyl]propionyloxy)ethyl] oxamide (Naugard®XL-1 supplied by Uniroyal).

1.18. Ascorbic acid (vitamin C)

1.19. Aminic antioxidants, for example N,N'-di-isopropyl-p-phenylenediamine, N,N'-di-sec-butyl-p-phenylenediamine, N,N'-bis(1,4-dimethylpentyl)-p-phenylenediamine, N,N'-bis(1-ethyl-3-methylpentyl)-p-phenylenediamine, N,N'-bis(1-methylheptyl)p-phenylenediamine, N,N'-dicyclohexyl-p-phenylenediamine, N,N'-diphenyl-p-phenylenediamine, N,N'-bis(2-naphthyl)-p-phenylenediamine, N-isopropyl-N'-phenyl-p-phenylenediamine, N-(1,3dimethylbutyl)N'-phenyl-p-phenylenediamine, N-(1-methylheptyl)-N'-phenyl-p-phenylenediamine, N-cyclohexyl-N'-phenyl-p-phenlenediamine, 4-(p-toluenesulfamoyl)diphenylamine, N,N'-dimethyl-N,N'-di-sec-butyl-p-phenylenediamine, diphenylamine, N-allyidiphenylamine, 4-isopropoxydiphenylamine, N-phenyl-1-naphthylamine, N-(4-tert-octylphenyl)-1-naphthylamine, N-phenyl-2-naphthylamine, octylated diphenylamine, for example p,p'-di-tert-octyidiphenylamine, 4-n-butylaminophenol, 4-butyrylaminophenol, 4-nonanoylaminophenol, 4-dodecanoylaminophenol, 4-octadecanoylaminophenol, bis(4-methoxyphenyl)amine, 2,6-di-tert-butyl-4-dimethylaminomethylphenol, 2,4'-diaminodiphenylmethane, 4,4'-diaminodiphenylmethane, N,N,N',N'-tetramethyl-4,4'-diaminodiphenylmethane, 1,2-bis[(2-methylphenyl)amino]ethane, 1,2-bis(phenylamino)propane, (o-tolyl)biguanide, bis[4-(1',3'-dimethylbutyl)phenyl]amine, tert-octylated N-phenyl-1-naphthylamine, a mixture of mono- and dialkylated tert-butyl/tert-octyidiphenylamines, a mixture of mono- and dialkylated nonyldiphenylamines, a mixture of mono- and dialkylated dodecyidiphenylamines, a mixture of mono- and dialkylated isopropyl/isohexyldiphenylamines, a mixture of mono- und dialkylated tert-butyidiphenylamines, 2,3-dihydro-3,3-dimethyl-4H-1,4-benzothiazine, phenothiazine, a mixture of mono- und dialkylated tert-butyl/tert-octylphenothiazines, a mixture of mono- und dialkylated tert-octyl-phenothiazines, N-allylphenothiazin, N,N,N',N'-tetraphenyl-1,4-diaminobut-2-ene, N,N-bis-(2,2,6,6-tetramethyl-piperid-4-yl-hexamethylenediamine, bis(2,2,6,6-tetramethylpiperid-4-yl)sebacate, 2,2,6,6-tetramethylpiperidin-4-one, 2,2,6,6-tetramethylpiperidin-4-ol.

2. UV Absorbers and Light Stabilisers 2.1. 2-(2'-Hydroxyphenyl)benzotriazoles, for example 2-(2'-hydroxy-5'-methylphenyl)-benzotriazole, 2-(3',5'-di-tert-butyl-2'-hydroxyphenyl)benzotriazole, 2-(5'-tert-butyl-2'-hydroxyphenyl)benzotriazole, 2-(2'-hydroxy-5'-(1,1,3,3-tetramethylbutyl)phenyl)benzotriazole, 2-(3',5'-di-tert-butyl-2'-hydroxyphenyl)-5-chloro-benzotriazole, 2-(3'- tert-butyl-2'-hydroxy-5'-methylphenyl)-5-chloro-benzotriazole, 2-(3'-sec-butyl-5'-tert-butyl-2'-hydroxyphenyl)benzotriazole 2-(2'-hydroxy-4'-octyloxyphenyl)benzotriazole, 2-(3',5'-di-tert-amyl-2'-hydroxyphenyl)benzotriazole, 2-(3',5'-bis-(α,α-dimethylbenzyl)-2'-hydroxyphenyl)benzotriazole, 2-(3'tert-butyl-2'-hydroxy-5'-(2-octyloxycarbonylethyl) phenyl)-5-chloro-benzotriazole, 2-(3'-tert-butyl-5'-[2-(2-ethylhexyloxy)-carbonylethyl]-2'-hydroxyphenyl)-5-chloro-benzotriazole, 2-(3'-tert-butyl-2'-hydroxy-5'-(2-methoxycarbonylethyl)phenyl)-5-chloro-benzotriazole, 2-(3'-tert-butyl-2'-hydroxy-5'-(2-methoxycarbonylethyl) phenyl)benzotriazole, 2-(3'-tert-butyl-2'-hydroxy-5'-(2-octyloxycarbonylethyl)phenyl)benzotriazole, 2-(3'-tert-butyl-5'-[2-(2'-ethylhexyloxy)carbonylethyl]-2'-hydroxyphenyl)benzotriazole, 2-(3'-dodecyl-2'-hydroxy-5'-methylphenyl)benzotriazole, 2-(3'-tert-butyl-2'-hydroxy-5'-(2-isooctyloxycarbonylethyl) phenylbenzotriazole, 2,2'-methylene-bis-[4-(1,1,3,3-tetramethylbutyl)-6-benzotriazole-2-ylphenol]; the transesterification product of 2-[3'-tert-butyl-5'-(2-methoxycarbonylethyl)-2'-hydroxyphenyl]-2H-benzotriazole with polyethylene glycol 300; $[R—CH_2CH_2—COO—CH_2CH_2 ]_2$ where R=3'-tert-butyl-4'-hydroxy-5'-2H-benzotriazol-2-ylphenyl, 2-[2'-hydroxy-3'-(α,α-dimethylbenzyl)-5'-(1,1,3,3-tetramethylbutyl)-phenyl]benzotriazole; 2-[2'-hydroxy-3'-(1,1,3,3-tetramethylbutyl)-5'-(α,α-dimephenyl] benzotriazole.

2.2. 2-Hydroxybenzophenones, for example the 4-hydroxy, 4-methoxy, 4-octyloxy, 4-decyloxy, 4-dodecyloxy, 4-benzyloxy, 4,2',4'-trihydroxy and 2'-hydroxy-4,4'-dimethoxy derivatives.

2.3. Esters of substituted and unsubstituted benzoic acids, as for example 4-tertbutyl-phenyl salicylate, phenyl salicylate, octylphenyl salicylate, dibenzoyl resorcinol, bis(4-tert-butylbenzoly) resorcinol, benzoyl resorcinol, 2,4-di-tert-butylphenyl 3,5-di-tert-butyl-4-hydroxybenzoate, hexadecyl 3,5-di-tert-butyl-4-hydroxybenzoate, octadecyl 3,5-di-tert-butyl-4-hydroxybenzolate, 2-methyl-4,6-di-tert-butylphenyl 3,5-di-tert-butyl-4-hydroxybenzoate.

2.4. Acrylates, for example ethyl α-cyano-β,β-diphenylacrylate, isooctyl α-cyano-β,β-diphenylacrylate, methyl α-carbomethoxycinnamate, methyl α-cyano-β-methyl-p-methoxy-cinnamate, butyl α-cyano-β-methyl-p-methoxy-cinnamate, methyl α-carbomethoxy-p-methoxycinnamate and N-(β-carbomethoxy-β-cyanovinyl)-2-methylindoline.

2.5. Nickel compounds, for example nickel complexes of 2,2'-thio-bis-[4-(1,1,3,3-tetramethylbutyl)phenol], such as the 1:1 or 1:2 complex, with or without additional ligands such as n-butylamine, triethanolamine or N-cyclohexyldiethanolamine, nickel dibutyidithiocarbamate, nickel salts of the monoalkyl esters, e.g. the methyl or ethyl ester, of 4-hydroxy-3,5-di-tert-butylbenzylphosphonic acid, nickel complexes of ketoximes, e.g. of 2-hydroxy-4-methylphenyl undecylketoxime, nickel complexes of 1-phenyl-4-lauroyl-5-hydroxypyrazole, with or without additional ligands.

2.6. Sterically hindered amines, for example bis(2,2,6,6-tetramethyl-4-piperidyl)sebacate, bis(2,2,6,6-tetramethyl-4-piperidyl)succinate, bis(1,2,2,6,6-pentamethyl-4-piperidyl)sebacate, bis(1-octyloxy-2,2,6,6-tetramethyl-4-piperidyl)sebacate, bis(1,2,2,6,6-pentamethyl-4-piperidyl) n-butyl-3,5-di-tert-butyl-4-hydroxybenzylmalonate, the condensate of 1-(2-hydroxyethyl)-2,2,6,6-tetramethyl-4-hydroxypiperidine and succinic acid, linear or cyclic condensates of N,N'-bis(2,2,6,6-tetramethyl-4-piperidyl) hexamethylenediamine and 4-tert-octylamino-2,6-dichloro-1,3,5-triazine, tris(2,2,6,6-tetramethyl-4-piperidyl)nitrilotriacetate, tetrakis(2,2,6,6-tetramethyl-4-piperidyl)-1,2,3,4-butane-tetracarboxylate, 1,1'-(1,2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2-(2-hydroxy-3,5-di-tert-butylbenzyl)malonate, 3-n-octyl-7,7,9,9-tetramethyl-1,3,8-triazaspiro[4.5]decan-2,4-dione, bis(1-octyloxy-2,2,6,6-tetramethylpiperidyl)sebacate, bis(1-octyloxy-2,2,6,6-tetramethylpiperidyl)succinate, linear or cyclic condensates of N,N'-bis-(2,2,6,6-tetramethyl-4-piperidyl) hexamethylenediamine and 4-morpholino-2,6-dichloro-1,3,5-triazine, the condensate of 2-chloro-4,6-bis(4-n-butylamino-2,2,6,6-tetramethylpiperidyl )-1 ,3,5-triazine and 1 ,2-bis (3-aminopropylamino)ethane, the condensate of 2-chloro-4,6-di-(4-n-butylamino-1,2,2,6,6-pentamethylpiperidyl)-1,3,5-triazine and 1,2-bis-(3-aminopropylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)pyrrolidin-2,5-dione, 3-dodecyl-1-(1,2,2,6,6-pentamethyl-4-piperidyl)pyrrolidine-2,5-dione, a mixture of 4-hexadecyloxy- and 4-stearyloxy-2,2,6,6-tetramethylpiperidine, a condensation product of N,N'-bis (2,2,6,6-tetramethyl-4-piperidyl)hexamethylenediamine and 4-cyclohexylamino-2,6-dichloro-1,3,5-triazine, a condensation product of 1,2-bis(3-aminopropylamino) ethane and 2,4,6-trichloro-1,3,5-triazine as well as 4-butylamino-2,2,6,6-te-(tramethylpiperidine (CAS Reg. No. [136504-96-6]); N-(2,2,6,6-tetramethyl-4-piperidyl)-n-do-decylsuccinimid, N-(1,2,2,6,6-pentamethyl-4-piperidyl)-n-dodecylsuccinimid, 2-undecyl-7,7,9,9-tetramethyl-1-oxa-3,8-diaza-4-oxo-spiro[4,5]decane, a reaction product of 7,7,9,9-tetramethyl-2-cycloundecyl-1-oxa-3,8-diaza-4-oxospiro [4,5]decane und epichlorohydrin, 1,1 -bis(1,2,2,6,6-pentamethyl-4-piperidylaxycarbony-2-(4-methoxyphenyl)ethene, N,N'-bis-formyl-N,N'-bis(2,2,6,6-tetramethyl-4-piperidyl) hexamethylenediamine, diester of 4-methoxy-methylene-malonic acid with 1,2,2,6,6-pentamethyl-4-hydroxypiperidine, poly[methylpropyl-3-oxy-4-(2,2,6,6-tetramethyl-4-piperidyl)]siloxane, reaction product of maleic acid anhydride-α-olefin-copolymer with 2,2,6,6-tetramethyl-4-aminopiperidine or 1,2,2,6,6-pentamethyl4-aminopiperidine.

2.7. Oxamides, for example 4,4'-dioctyloxyoxanilide, 2,2'-diethoxyoxanilide, 2,2'-dioctyloxy-5,5'-di-tert-butoxanilide, 2,2'-didodecyloxy-5,5'-di-tert-butoxanilide, 2-ethoxy-2'ethyloxanilide, N,N'-bis(3-dimethylaminopropyl)oxamide, 2-ethoxy-5-tert-butyl-2'-ethoxanilide and its mixture with 2-ethoxy-2'-ethyl-5,4'-di-tert-butoxanilide, mixtures of o- and p-methoxy-disubstituted oxanilides and mixtures of o- and p-ethoxy-disubstituted oxanilides.

2.8. 2-(2-Hydroxyphenyl)-1,3,5-triazines, for example 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4,6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-(2-hydroxy-4-tridecyloxyphenyl)-4,6-bis(2,4-dimethylphenyl)-1,3,5-triazine, 2-[2-hydroxy-4-(2-hydroxy-3-butyloxy-propoxy)phenyl]-4,6-bis(2,4- dimethyl)-1,3,5-triazine, 2-[2-hydroxy-4-(2-hydroxy-3-octyloxy-propyloxy)phenyl]-4,6-bis(2,4-dimethyl)-1,3,5-triazine, 2-[4-(dodecyloxyltridecyloxy-2-hydroxypropoxy)-2-hydroxy-phenyl]-4,6-bis(2,4-dimethylphenyl)-1,3,5-triazine, 2-[2-hydroxy-4-(2-hydroxy-3-dodecyloxy-propoxy)phenyl]-4,6-bis(2,4-dimethylphenyl)-1,3,5-triazine, 2-(2-hydroxy-4-hexyloxy)phenyl-4,6-diphenyl- 1,3,5-triazine, 2-(2-hydroxy-4-methoxyphenyl)-4,6-diphenyl-1,3,5-triazine, 2,4,6-tris[2-hydroxy-4-(3-butoxy-2-hydroxy-propoxy) phenyl]-1,3,5-triazine, 2-(2-hydroxyphenyl)-4-(4-methoxyphenyl)-6-phenyl-1,3,5-triazine, 2-{2-hydroxy-4-[3-(2-ethylhexyl-1-oxy)-2-hydroxypropyloxy] phenyl}4,6-bis(2,4-dimethylphenyl)-1,3,5-triazine.

3. Metal deactivators, for example N,N'-diphenyloxamide, N-salicylal-N'-salicyloyl hydrazine, N,N'-bis(salicyloyl) hydrazine, N,N'-bis(3,5-di-tert-butyl-4-hydroxyphenylpropionyl) hydrazine, 3-salicyloylamino-1,2,4-triazole, bis(benzylidene)oxalyl dihydrazide, oxanilide, isophthaloyl dihydrazide, sebacoyl bisphenylhydrazide, N,N'-diacetyladipoyl dihydrazide, N,N'-bis(salicyloyl) oxalyl dihydrazide, N,N'-bis(salicyloyl)thiopropionyl dihydrazide.

4. Phosphites and phosphonites, for example triphenyl phosphite, diphenyl alkyl phosphites, phenyl dialkyl phosphites, tris(nonylphenyl) phosphite, trilauryl phosphite, trioctadecyl phosphite, distearyl pentaerythritol diphosphite, tris(2,4-di-tert-butylphenyl) phosphite, diisodecyl pentaerythritol diphosphite, bis(2,4-di-tert-butylphenyl) pentaerythritol diphosphite, bis(2,6-di-tert-butyl-4-methylphenyl)-pentaerythritol diphosphite, diisodecyloxypentaerythritol diphosphite, bis(2,4-di-tert-butyl-6-methylphenyl)pentaerythritol diphosphite, bis(2,4,6-tris(tert-butylphenyl)pentaerythritol diphosphite, tristearyl sorbitol triphosphite, tetrakis(2,4-di-tert-butylphenyl) 4,4'-biphenylene diphosphonite, 6-isooctyloxy-2,4,8,10-tetra-tert-butyl-12H-di-benz[d,g]-1,3,2-dioxaphosphocin, 6-fluoro-2,4,8,10-tetra-tert-butyl- 1 2-methyl-dibenz[d,g]-1,3,2-dioxaphosphocin, bis(2,4-di-tert-butyl-6-methylphenyl) methyl phosphite, bis(2,4-di-tert-butyl-6-methylphenyl) ethyl phosphite, 2,2',2''-nitrilo[triethyltris(3,3',5,5'-tetra-tert-buty-1,1'-biphenyl-2,2'-diyl)phosphite], 2-ethylhexyl(3,3',5,5'-tetra-tert-butyl-1,1'-biphenyl-2,2'-di-yl)phosphite.

Especially preferred are the following phosphites:

Tris(2,4-di-tert-butylphenyl) phosphite (Irgafos®168, Ciba-Geigy), tris(nonylphenyl) phosphite, (A)

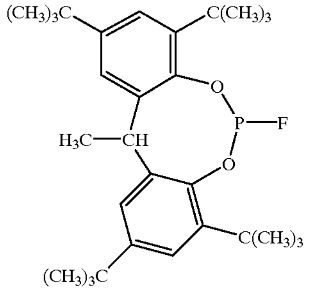

-continued (B)

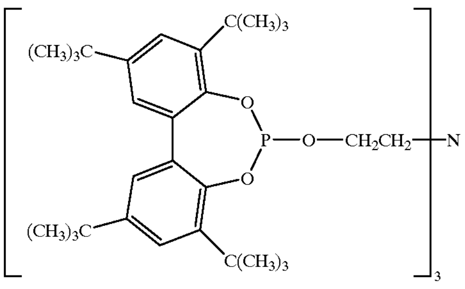

(C)

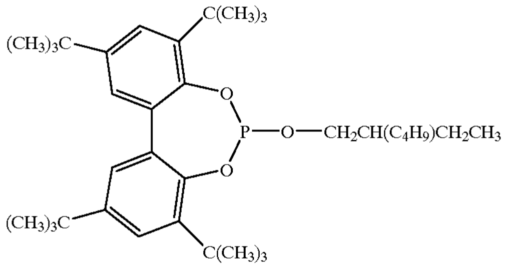

(D)

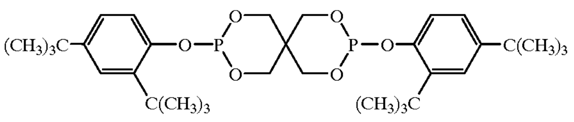

(E)

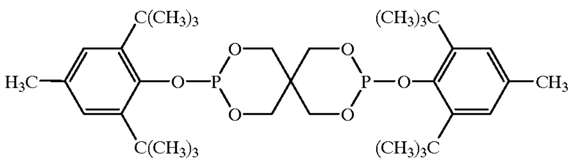

(F)

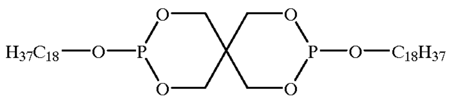

(G)

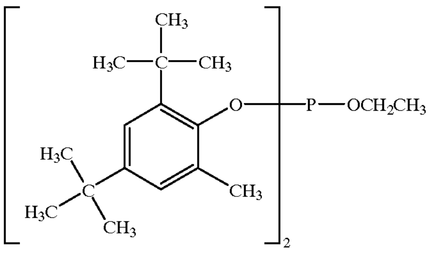

5. Hydroxylamines, for example, N,N-dibenzylhydroxylamine, N,N-diethylhydroxylamine, N,N-dioctylhydroxylamine, N,N-dilaurylhydroxylamine, N,N-ditetradecylhydroxylamine, N,N-dihexadecylhydroxylamine, N,N-dioctadecylhydroxylamine, N-hexadecyl-N-octadecylhydroxylamine, N-heptadecyl-N-octadecylhydroxylamine, N,N-dialkylhydroxylamine derived from hydrogenated tallow amine.

6. Nitrones, for example, N-benzyl-alpha-phenyl-nitrone, N-ethyl-alpha-methyl-nitrone, N-octyl-alpha-heptyl-nitrone, N-lauryl-alpha-undecyl-nitrone, N-tetradecylalpha-tridcyl-nitrone, N-hexadecyl-alpha-pentadecyl-nitrone, N-octadecyl-alpha-heptadecyl-nitrone, N-hexadecyl-alpha-heptadecyl-nitrone, N-ocatadecyl-alpha-pentadecyl-nitrone, N-heptadecyl-alpha-heptadecyl-nitrone, N-octadecyl-alpha-hexadecyl-nitrone, nitrone derived from N,N-dialkylhydroxylamine derived from hydrogenated tallow amine.

7. Thiosynergists, for example, dilauryl thiodipropionate or distearyl thiodipropionate.

8. Peroxide scavengers, for example esters of β-thiodipropionic acid, for example the lauryl, stearyl, myristyl or tridecyl esters, mercaptobenzimidazole or the zinc salt of 2-mercaptobenzimidazole, zinc dibutyldithiocarbamate, dioctadecyl disulfide, pentaerythritol tetrakis(β-dodecylmercapto)propionate.

9. Polyamide stabilisers, for example, copper salts in combination with iodides and/or phosphorus compounds and salts of divalent manganese.

10. Basic co-stabilisers, for example, melamine, polyvinylpyrrolidone, dicyandiamide, triallyl cyanurate, urea derivatives, hydrazine derivatives, amines, polyamides, polyurethanes, alkali metal salts and alkaline earth metal salts of higher fatty acids for example calcium stearate, zinc stearate, magnesium behenate, magnesium stearate, sodium ricinoleate and potassium palmitate, antimony pyrocatecholate or zink pyrocatecholate.

11. Nucleating agents, for example, inorganic substances such as talcum, metal oxides such as titanium dioxide or magnesium oxide, phosphates, carbonates or sulfates of, preferably, alkaline earth metals; organic compounds such as mono- or polycarboxylic acids and the salts thereof, e.g. 4-tert-butylbenzoic acid, adipic acid, diphenylacetic acid, sodium succinate or sodium benzoate; polymeric compounds such as ionic copolymers (ionomers).

12. Fillers and reinforcing agents, for example, calcium carbonate, silicates, glass fibres, glass bulbs, asbestos, talc, kaolin, mica, barium sulfate, metal oxides and hydroxides, carbon black, graphite, wood flour and flours or fibers of other natural products, synthetic fibers.

13. Other additives, for example, plasticisers, lubricants, emulsifiers, pigments, rheology additives, catalysts, flow-control agents, optical brighteners, flameproofing agents, antistatic agents and blowing agents.

14. Benzofuranones and indolinones, for example those disclosed in U.S. Pat. Nos. 4,325,863; 4,338,244; 5,175,312; 5,216,052; 5,252,643; DE-A-4316611; DE-A-4316622; DE-A-4316876; EP-A-0589839 or EP-A-0591 102 or 3-[4-(2-acetoxyethoxy)phenyl]-5,7-di-tert-butyl-benzofuran-2-one, 5,7-di-tert-butyl-3-[4-(2-stearoyloxyethoxy)phenyl] benzofuran-2-one, 3,3'-bis[5,7-di-tert-butyl-3-(4-[2-hydroxyethoxy]phenyl)benzofuran-2-one],5,7-di-tert-butyl-3-(4-ethoxyphenyl)benzofuran-2-one, 3-(4-acetoxy-3, 5dimethylphenyl)-5,7-di-tert-butyl-benzofuran-2-one, 3-(3, 5-dimethyl-4-pivaloyloxyphenyl)-5,7-di-tert-butyl-benzofuran-2-one, 3-(3,4-dimethylphenyl)-5,7-di-tert-butyl-benzofuran-2-one, 3-(2,3-dimethylphenyl)-5,7-di-tert-butyl-benzofuran-2-one.

Finally, examples of other suitable additives are plasticizers, lubricants, emulsifiers, pigments, rheologial additives, catalysts, levelling assistants, optical brighteners, flameproofing agents, antistats, blowing agents, solvents, dyes, stabilizers and thixotropic agents.

Examples of benzofuran-2-ones are compounds of the formula

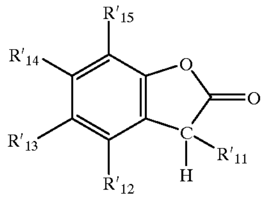

in which $R'_{11}$ is an unsubstituted or substituted carbocyclic or heterocyclic aromatic ring system;

$R'_{12}$ is hydrogen;

$R'_{14}$ is hydrogen, alkyl of 1 to 12 carbon atoms, cyclopentyl, cyclohexyl or chlorine;

$R'_{13}$ has the meaning of $R'_{12}$ or $R'_{14}$ or is a radical of the formula

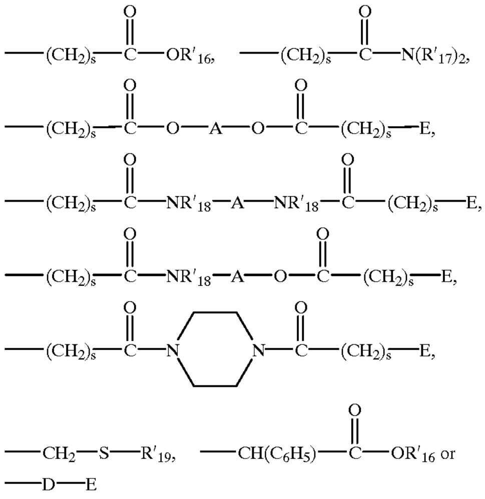

which $R'_{16}$ is hydrogen, alkyl of 1 to 18 carbon atoms, alkyl of 2 to 18 carbon atoms which is interrupted by oxygen or sulfur, dialkylaminoalkyl with a total of 3 to 16 carbon atoms, cyclopentyl, cyclohexyl, phenyl, or phenyl which is substituted by 1 to 3 alkyl radicals having together not more than 18 carbon atoms;

s is 0, 1 or 2;

the substituents $R'_{17}$ independently of one another are hydrogen, alkyl of 1 to 18 carbon atoms, cyclopentyl, cyclohexyl, phenyl, or phenyl which is substituted by 1 or 2 alkyl radicals having together not more than 16 carbon atoms, a radical of the formula $—C_2H_4OH$,

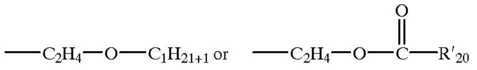

or, together with the nitrogen atom to which they are attached, form a piperidine or morpholine radical;

t is 1 to 18;

$R'_{20}$ is hydrogen, alkyl of 1 to 22 carbon atoms or cycloalkyl of 5 to 12 carbon atoms;

A is alkylene of 2 to 22 carbon atoms which is uninterrupted or interrupted by nitrogen, oxygen or sulfur;

R'$_{18}$ is hydrogen, alkyl of 1 to 18 carbon atoms, cyclopentyl, cyclohexyl, phenyl, or benzyl or phenyl which is substituted by 1 or 2 alkyl radicals having together not more than 16 carbon atoms;

R'$_{19}$ is alkyl of 1 to 18 carbon atoms;

D is —O—, —S—, —SO—, —$SO_2$— or —C(R'$_{21}$)$_2$—; the substituents R'$_{21}$ independently of one another are hydrogen or $C_1$–$C_{16}$alkyl, the two R'$_{21}$s together containing 1 to 16 carbon atoms, or R'$_{21}$ is phenyl or a radical of the formula

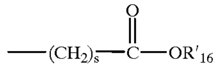
or
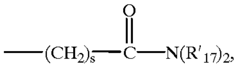

in which s, R'$_{16}$ and R'$_{17}$ are as defined above;

E is a radical of the formula

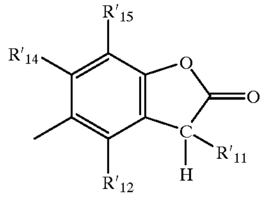

in which R'$_{11}$, R'$_{12}$ and R'$_{14}$ are as defined above; and

R'$_{15}$ is hydrogen, alkyl of 1 to 20 carbon atoms, cyclopentyl, cyclohexyl, chlorine or a radical of the formula

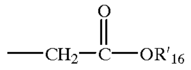
or
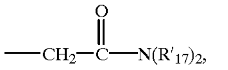

in which R'$_{16}$ and R'$_{17}$ are as defined above, or R'$_{15}$ together with R'$_{14}$ forms a tetramethylene radical.

Preferred benzofuran-2-ones are those in which R'$_{13}$ is hydrogen, alkyl of 1 to 12 carbon atoms, cyclopentyl, cyclohexyl, chlorine or a radical of the formula

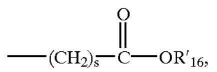
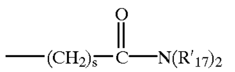
or

—D—E, in which s, R'$_{16}$, R'$_{17}$, D and E are as defined above, and R'$_{16}$ in particular has the meaning of hydrogen, alkyl of 1 to 18 carbon atoms, cyclopentyl or cyclohexyl.

Preference is also given to those benzofuran-2-ones in which R'$_{11}$ is phenyl or is phenyl which is substituted by 1 or 2 alkyl radicals having together not more than 12 carbon atoms;

R'$_{12}$ is hydrogen; R'$_{14}$ is hydrogen or alkyl of 1 to 12 carbon atoms;

R'$_{13}$ is hydrogen, alkyl of 1 to 12 carbon atoms,

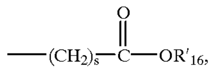
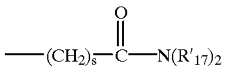
or

-continued

—D—E;

R'$_{15}$ is hydrogen, alkyl of 1 to 20 carbon atoms,

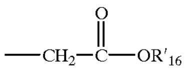
or
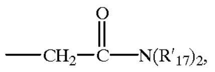

or R'$_{15}$ together with R'$_{14}$ forms a tetramethylene radical, where s, R'$_{16}$, R'$_{17}$, D and E are as defined at the beginning.

Likewise of particular interest are those benzofuran-2-ones in which R'$_{13}$ is hydrogen, alkyl of 1 to 12 carbon atoms or -D-E: R'$_{12}$ and R'$_{14}$ independently of one another are hydrogen or alkyl of 1 to 4 carbon atoms; and R'$_{15}$ is alkyl of 1 to 20 carbon atoms, where D and E are as defined at the beginning.

Likewise of special interest, finally, are benzofuran-2-ones in which R'$_{13}$ is alkyl of 1 to 4 carbon atoms or -D-E; R'$_{12}$ and R'$_{14}$ are hydrogen; and R'$_{15}$ is alkyl of 1 to 4 carbon atoms, cyclopentyl or cyclohexyl, where D is a group —C(R'$_{21}$)$_2$— and E is a radical of the formula

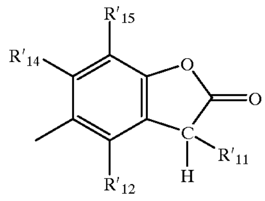

the substituents R'$_{21}$ being identical to or different from one another and each being alkyl of 1 to 4 carbon atoms, and R'$_{11}$, R'$_{12}$, R'$_{14}$ und R'$_{15}$ being as defined.

The amount of additionally employed benzofuran-2-ones can vary within wide limits. For example, their content in the novel compositions can be from 0.0001 to 5, preferably from 0.001 to 2, in particular from 0.01 to 2% by weight.

The nature and amount of the further stabilizers added is determined by the nature of the substrate to be stabilized and by its intended use. In many cases from 0.1 to 5% by weight is used, based on the polymer to be stabilized.

The novel composition comprising i) a material, especially an organic polymeric material, sensitive to damage by light, oxygen and/or heat, and ii) as stabilizer at least one polyoxyalkylene substituted and bridged triazine, benzotriazole and benzophenone derivative of the formula I or II preferably comprises, as a further component in addition to these components, a light stabilizer of the sterically hindered amine and/or of the 2-hydroxyphenyl-2H-benzotriazole type. Examples of such costabilizers can be found in the above listing under sections 2.1 and 2.6.

For achieving maximum light stability, there is particular interest in the addition of sterically hindered amines, as given in the above list in 2.6. A composition which comprises a light stabilizer of the sterically hindered amine type (HALS) has a further component in addition to components i and ii is therefore particularly preferred.

The light stabilizer involved here is preferably a 2,2,6,6-tetraalkylpiperidine derivative containing at least one group of the formula

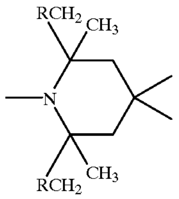

in which R is hydrogen or methyl, especially hydrogen.

The novel, polyoxyalkylene substituted and bridged triazine, benzotriazole and benzophenone derivatives can be employed with particular advantage in compositions which as one component comprise a synthetic organic polymer, especially a thermoplastic polymer, or a binder for coatings such as, for example, paints.

If the component is a binder for coatings, the addition of the above-described light stabilizers of the sterically hindered amine type (HALS) to the novel composition is particularly worthy of recommendation.

Also of interest are compositions in which the synthetic organic polymer is a polyolefin, for example polyethylene or polypropylene.

Incorporation into the organic material to be stabilized, for example into the synthetic organic, especially thermoplastic polymers, can be carried out by adding the novel, polyoxyalkylene substituted and bridged triazine, benzotriazole and benzophenone derivatives, with or without additional additives, by the methods customary in the art.

Incorporation can judiciously be effected before or during the shaping operation, for example by mixing the pulverulent components or by adding the stabilizers to the melt or solution of the polymer, or by applying the dissolved or dispersed compounds to the polymer, with or without subsequent evaporation of the solvent. In the case of elastomers, these can also be stabilized as latices. A further possibility for incorporating the novel, polyalkylene substituted and bridged triazine, benzotriazole and benzophenone derivatives in polymers is to add them before or during the polymerization of the corresponding monomers and/or prior to crosslinking.

The novel, polyoxyalkylene substituted and bridged triazine, benzotriazole and benzophenone derivatives or mixtures thereof can also be added to the plastics to be stabilized in the form of a masterbatch which comprises these compounds in a concentration, for example, of from 2.5 to 25% by weight.

The novel, polyoxyalkylene substituted and bridged triazine, benzotriazole and benzophenone derivatives can judiciously be incorporated by the following methods:

as emulsion or dispersion (e.g. to latices or emulsion polymers);

as a dry mix during the mixing of additional components or polymer mixtures;

by direct addition to the processing apparatus (for example extruders, internal mixers, etc.); or as a solution or melt.

The stabilized polymer compositions obtained in this way can be converted by the customary methods, for example by hot pressing, spinning, extrusion or injection moulding, into shaped articles, for example fibres, films, tapes, sheets, including multi-wall sheets, vessels, pipes and other profiles.

The invention therefore additionally provides for the use of the novel polymer composition for producing a shaped article.

Particular preference is also given to the use of the novel compounds of the formulae I and/or II as stabilizers in coating compositions, for example paints of all kinds. This also means a process as described above in which the organic polymer is a binder for coating material. The coating materials can be pigmented or unpigmented coating materials or metal-effect (metallic) paints. They may contain an organic solvent or may be solvent-free or may be aqueous coating materials. Water-based coating materials are preferred in this context.

Use in multicoat systems is possible, in which case the concentration of the novel, polyoxyalkylene substituted and bridged triazine, benzotriazole and benzophenone derivatives in the topcoat can be relatively high, for example from 1 to 15 parts by weight. in particular 3–10 parts by weight per 100 parts by weight of solid binder.

Suitable binders are in principle all those customary in the art, for example those as described in Ullmann's Encyclopedia of Industrial Chemistry, 5th Ed., Vol. A18, pp. 368–426, VCH, Weinheim 1991. The binder is generally a film-forming binder based on a thermoplastic or thermosetting resin, predominantly on a thermosetting resin. Examples of these are alkyd, acrylic, polyester, phenolic, melamine, epoxy and polyurethane resins and mixtures thereof.

Preference is given to coating compositions including a binder comprising a functional acrylate resin and a crosslinker.

Examples of coating compositions with specific binders are the following:

1. paints based on cold- or hot-crosslinkable alkyd, acrylate, polyester, epoxy or melamine resins or mixtures of such resins, with or without addition of a curing catalyst;
2. two-component polyurethane paints based on hydroxyl-containing acrylate, polyester or polyether resins and on aliphatic or aromatic isocyanates, isocyanurates or polyisocyanates;
3. one-component polyurethane paints based on blocked isocyanates, isocyanurates or polyisocyanates, which are deblocked in the course of stoving; the addition of melamine resins may also be possible;
4. one-component polyurethane paints based on aliphatic or aromatic urethanes or polyurethanes and on hydroxyl-containing acrylate, polyester or polyether resins;
5. one-component polyurethane paints based on aliphatic or aromatic urethane acrylates or polyurethane acrylates having free amine groups in the urethane structure and on melamine resins or polyether resins, with or without addition of a curing catalyst;
6. two-component paints based on (poly)ketimines and aliphatic or aromatic isocyanates, isocyanurates or polyisocyanates;
7. two-component paints based on (poly)ketimines and on an unsaturated acrylate resin or on a polyacetoacetate resin or on a methacrylamidoglycolate methyl ester;
8. two-component paints based on carboxyl- or amino-containing polyacrylates and polyepoxides;
9. two-component paints based on acrylate resins containing anhydride groups and on a polyhydroxy or polyamino component;
10. two-component paints based on acrylate-containing anhydrides and polyepoxides;
11. two-component paints based on (poly)oxazolines and on acrylate resins containing anhydride groups, or unsaturated acrylate resins or aliphatic or aromatic isocyanates, isocyanurates or polyisocyanates;
12. two-component paints based on unsaturated polyacrylates and polymalonates;

13. thermoplastic polyacrylate paints based on thermoplastic acrylate resins or externally crosslinking acrylate resins in combination with etherified metamine resins;

14. paint systems based on siloxane-modified or fluorine-modified acrylate resins.

In addition to components i) and ii), the novel coating composition preferably comprises, as further component, a light stabilizer of the sterically hindered amine, 2-(2-hydroxyphenyl)-1 ,3,5-triazine and/or 2-hydroxyphenyl-2H-benzotriazole type, for example as mentioned in the above list under sections 2.1, 2.6 and 2.8. Of particular industrial interest in this context is the addition of 2-monoresorcinyl-4,6-diaryl-1,3,5-triazines and/or 2-hydroxyphenyl-2H-benzotriazoles.

In order to attain maximum light stability it is of particular interest to add sterically hindered amines as given by way of example in the above list under 2.6. The invention therefore also provides a coating composition which, in addition to components i) and ii), comprises as further component a light stabilizer of the sterically hindered amine type.

This is preferably a 2,2,6,6-tetraalkylpiperidine derivative as indicated above.

The further component is preferably used in an amount of 0.05–5 parts by weight per 100 parts by weight of the solid binder.

Examples of tetraalkylpiperidine derivatives that can be used as the further component are given in EP-A-356 677, pages 3–17, sections a) to f). Those sections of that EP-A are regarded as part of the present description. It is particularly judicious to employ the following tetraalkylpiperidine derivatives:

bis(2,2,6,6-tetramethylpiperidin-4-yl) succinate, bis(2,2,6,6-tetramethylpiperidin-4-yl) sebacate, bis(1,2,2,6,6-pentamethylpiperidin-4-yl) sebacate, di(1,2,2,6,6-penta-methylpiperidin-4-yl) butyl-(3,5-di-tert-butyl-4-hydroxybenzyl)malonate, bis(1 -octyloxy-2,2,6,6-tetramethylpiperidin-4-yl) sebacate, tetra(2,2,6,6-tetramethylpiperidin-4-yl) butane-1,2,3,4-tetracarboxylate, tetra(1,2,2,6,6-pentamethylpiperidin-4-yl) butane-1,2,3,4-tetracarboxylate, 2,2,4,4-tetramethyl-7-oxa-3,20-diaza-21 -oxodispiro [5.1.11.2]heneicosane, 8-acetyl-3-dodecyl-1,3,8-triaza-7,7,9,9-tetramethylspiro [4.5]-decane-2,4-dione, 1,1 -bis(1,2,2,6,6-pentamethylpiperidin-4-yl-oxycarbonyl)-2-(4-methoxyphenyl)ethene, or a compound of the formulae

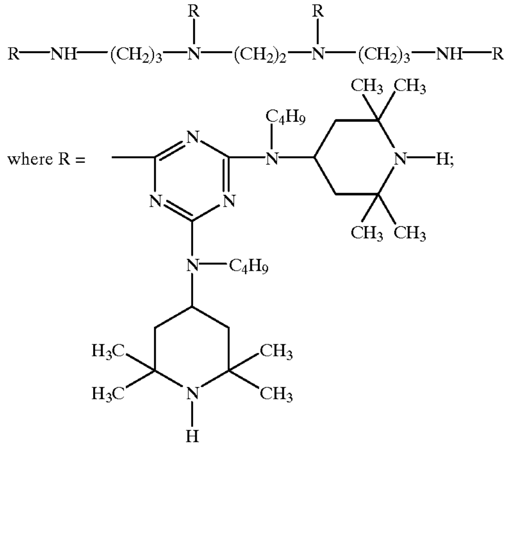

-continued

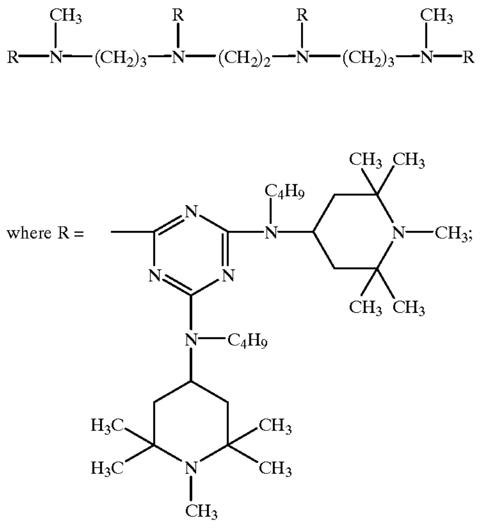

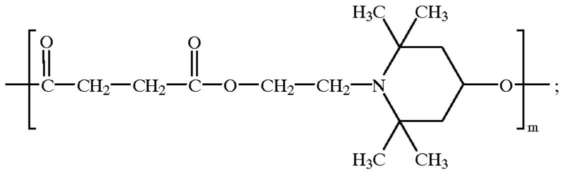

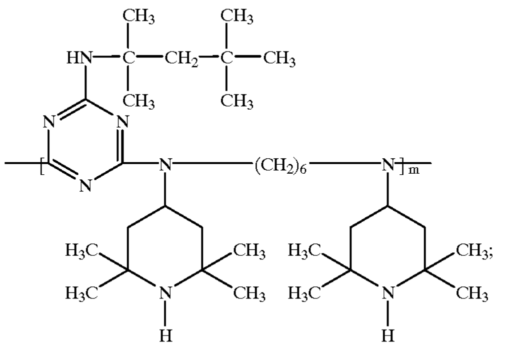

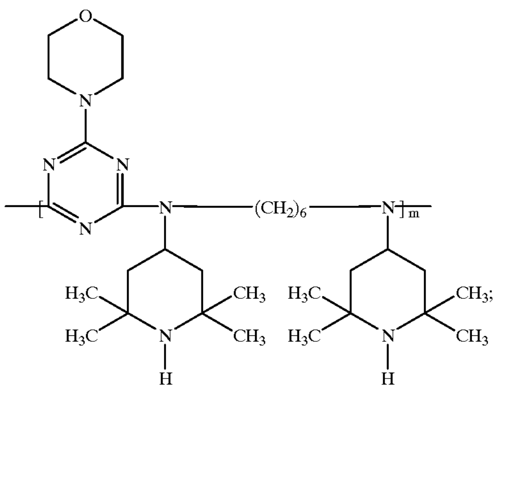

-continued

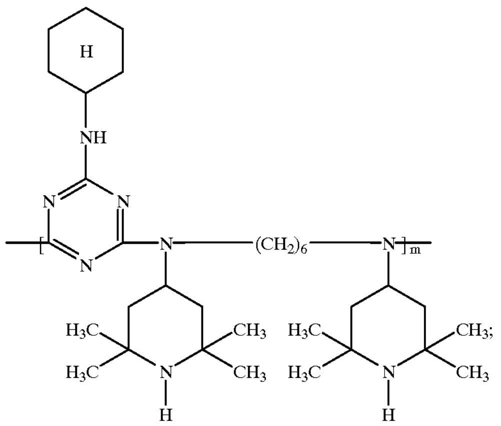

or

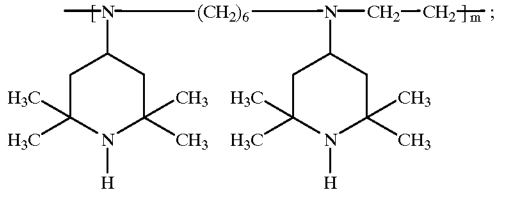

in which m is 5–50.

In addition to components i), ii) and, if used, a further light stabilizer, the coating composition can comprise further components, examples being solvents, pigments, dyes, plasticizers, stabilizers, thixotropic agents, drying catalysts and/or levelling assistants.

Examples of possible components are those as described in Ullmann's Encyclopedia of Industrial Chemistry, 5th Ed., Vol. A18, pp. 429–471, VCH, Weinheim 1991.

Possible drying catalysts or curing catalysts are, for example, organometallic compounds, amines, amino-containing resins and/or phosphines. Examples of organometallic compounds are metal carboxylate, especially those of the metals Pb, Mn, Co, Zn, Zr or Cu, or metal chelates, especially those of the metals Al, Ti or Zr, or organometallic compounds such as, for example, organotin compounds.

Examples of metal carboxylates are the stearates of Pb, Mn or Zn, the octoates of Co, Zn or Cu, the naphthenates of Mn and Co or the corresponding linoleates, resinates or tallates.

Examples of metal chelates are the aluminium, titanium or zirconium chelates of acetylacetone, ethyl acetylacetate, salicylaldehyde, salicylaldoxime, o-hydroxyacetophenone or ethyl trifluoracetylacetate, and the alkoxides of these metals.

Examples of organotin compounds are dibutyltin oxide, dibutyltin dilaurate or dibutyltin dioctoate.

Examples of amines are, in particular, tertiary amines, for example tributylamine, triethanolamine, N-methyidiethanolamine, Ndimethylethanolamine, N-ethylmorpholine, N-methylmorpholine or diazabicyclooctane (triethylenediamine) and salts thereof. Further examples are quaternary ammonium salts, for example trimethylbenzylammonium chloride.

Amino-containing resins are simultaneously binder and curing catalyst. Examples thereof are amino-containing acrylate copolymers.

The curing catalyts used can also be phosphines, for example triphenylphosphine.

The novel coating compositions may also be radiation-curable coating compositions. In this case the binder consists essentially of monomeric or oligomeric compounds having ethylenically unsaturated bonds (prepolymers) which, following application, are cured—i.e. converted to a crosslinked, high molecular mass form—by means of actinic radiation. Where the system involved is a UV-curing system it generally comprises, in addition, a photoinitiator. Corresponding systems are described in the abovementioned publication, Ullmann's Encyclopedia of Industrial Chemistry, 5th Ed., Vol.A18, pages 451–453. In radiation-curable coating compositions the novel stabilizer mixtures can be employed even without the addition of sterically hindered amines.

The novel coating compositions can be applied to any desired substrates, for example to metal, wood, plastic or ceramic materials. In the finishing of automotbiles they are preferably used as a topcoat. Where the topcoat comprises two layers, of which the bottom layer is pigmented and the top layer is not, the novel coating composition can be used for the top or the bottom layer or for both layers, but preferably for the top layer.

The novel coating compositions can be applied to the substrates by the customary techniques, for example by spreading, spraying, flowcoating, dipping or electrophoresis; see also Ullmann's Encyclopedia of Industrial Chemistry, 5th Ed., Vol. A18, pp. 491–500.

Depending on the binder system, the coatings can be cured at room temperature or by heating. The coatings are preferably cured at 50–150° C., powder coatings also at higher temperatures.

The coatings obtained in accordance with the invention have excellent resistance to damaging effects of light, oxygen and heat; particular mention should be made of the good light stability and weathering resistance of the resulting coatings, for example paints.

The invention therefore also provides a coating, especially a paint, which has been stabilized against the damaging effects of light, oxygen and heat by adding a compound of the formula I and/or II. The paint is preferably a topcoat for automobiles. The invention additionally comprises a process for stabilizing a coating based on organic polymers against damage by light, oxygen and/or heat, which comprises admixing to the coating composition a compound of the formula I or II or a mixture of compounds of the formulae I and II and for the use of these compounds in the coating compositions as stabilizers against damage by light, oxygen and heat.

The coatings can comprise an organic solvent or solvent mixture in which the binder is soluble. However, the coating composition can also be an aqueous solution or dispersion. The vehicle can also be a mixture of an organic solvent and water. The coating composition can also be a high-solids paint or may be free from solvent (e.g. a powder coating). Powder coatings are, for example, those as described in Ullmann's Encyclopedia of Industrial Chemistry, 5th Ed., Vol. A18, pp. 438–444. The powder coating can also be in the form of powder slurry, i.e. of a dispersion of the powder, preferably in water.

The pigments can be inorganic, organic or metallic pigments. The novel coating compositions preferably contain no pigments and are used as clearcoat.

Preference is likewise given to the use of the coating composition as a topcoat for applications in the automobile industry, especially as pigmented or unpigmented topcoat of the paint system. However, use for underlying coats is also possible.

The novel, polyoxyalkylene substituted and bridged triazine, benzotriazole and benzophenone derivatives according to the invention are, moreover, readily dispersible in aqueous gelatin, which simplifies their incorporation into, for example, photographic layers and renders the use of oils superfluous. This results in a low layer thickness or, with a constant layer thickness, in a higher concentration of UV absorber. The polyalkylene substituted and bridged triazine, benzotriazole and benzophenone derivatives are particularly suitable for increasing the stability of the magenta, cyan and yellow layer of photographic materials by being able to be incorporated into layers disposed above the magenta or cyan layer or directly into the cyan layer.

The polyoxyalkylene substituted and bridged triazine, benzotriazole and benzophenone derivatives according to the invention can be used for all kinds of photosensitive material.

For example, they can be employed for colour paper, colour reversal paper, direct positive colour material, colour negative film, colour positive film and colour reversal film. They are preferably used, inter alia, for photosensitive colour material which comprises a reversal substrate or which forms positives.

Also possible is the use of mixtures of the novel, polyoxyalkylene substituted and bridged triazine, benzotriazole and benzophenone derivatives with one another, or in particular, of the dimeric triazine compounds of the formula II in which $A_1$ is a triazine radical of the formula III, with other UV absorbers, such as hydroxyphenylbenzotriazoles (e.g. U.S. Pat. Nos. 4,853,471 or 4,973,702 or 4,921,966 or 4,973,701), benzophenones, oxanilides, cyanoacrylates, salicylic esters, acrylonitriles or thiazolines, although it is advantageous to employ these other UV absorbers, which are dissolved in oil, in the photographic material in layers other than those in which the novel, polyoxyalkylene substituted and bridged triazine, benzotriazole and benzophenone derivatives are situated.

In particular it is possible with great success to stabilize photographic materials similar to those described in U.S. Pat. No. 4,518,686.

Of particular interest is photographic material comprising, on a support, a blue-sensive, a green-sensitive and/or a red-sensitive silver halide emulsion layer and, if desired, a top layer and intermediate layer, in a system which comprises at least one polyoxyalkylene substituted and/or bridged triazine, benzotriazole or benzophenone derivative of the formula I or II in at least one layer, in the top layer and/or intermediate layer.

The compounds of the formula I and II stabilize both the colour couplers and the photodyes which are formed after exposure and development against the effect of light. They prevent or retard the bleaching or changing colour of the photodyes under the effect of light. They do not react with the customary dye couplers and do not impair the photographic process of colour formation.

As mentioned, the polyoxyalkylene substituted and bridged triazine, benzotriazole and benzophenone derivatives according to the invention can also be used for stabilizing printing inks, including inkjet printing inks. In this case the inks are notable for good stability against the effect of light. They can be used, for example, for felt-tip pens, stamp pads, fountain pens and pen plotters and in offset, letterpress, flexographic and intaglio printing processes, as well as in ink ribbons for dot matrix printing and letter-quality printing. The printers used in modern-day inkjet printing techniques are divided into those with a continuous ink jet and drop-on-demand printers, especially bubble-jet printers. For this kind of printer, it is possible to use inks comprising the novel polyoxyalkylene substituted and bridged triazine, benzotriazole and benzophenone derivatives of the formula I and/or II.

The inks preferably contain 0.01–30% by weight, in particular 0.1–20% by weight, of at least one compound of the formulae I or II.

A further use of the novel compounds I and II is in printing inks which are used in particular for printing polyester fibre materials with disperse dyes. In this case both the applied printing inks and the fibre materials are considerably enhanced by the action of light and, in particular, with simultaneous thermal irradiation. Printing inks comprising the novel compounds I and II can therefore be used for printing polyester fibre materials, especially in the automotive sector or in the swimwear sector, or else in interior textile applications or in connection with so-called outdoor articles, where there are stringent requirements on the lightfastness of the printing inks and on the photochemical stability of the fibres, with very great success. Polyester fibres are photochemically stabilized and the lightfastness of the printing inks applied to these fibre materials is increased. The fibres are printed with an aqueous printing paste which comprises not only the disperse dye but also at least one novel compound of the formula I and/or II. The compounds of the formula I or II used for such an application advantageously have a sublimation resistance of up to about 165° C.

The suitable compounds of the formula I or II are employed as aqueous dispersions.

Suitable dispersants for this process are compounds selected from the following classes:

(a) acidic esters or their salts of alkylene oxide adducts of the formula

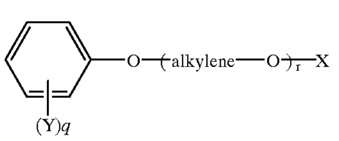

in which

X is the acid radical of an inorganic, oxygen-containing acid, for example sulfuric acid or, preferably, phosphoric acid, or else is the radical of an organic acid, and Y is $C_1$–$C_{12}$alkyl, aryl or aralkyl, alkylene is the ethylene or propylene radical, q is 1 to 4 and r is 4 to 50, (b) polystyrenesulfonates, (c) fatty acid taurides, (d) alkylated diphenyl oxide mono- or disulfonates, (e) sulfonates of polycarboxylic esters, (f) the adducts of from 1 to 60, preferably from 2 to 30 mol of ethylene oxide and/or propylene oxide with fatty amines, fatty amides, fatty acids or fatty alcohols having in each case 8 to 22 carbon atoms or with trihydric to hexahydric alkanols having 3 to 6 carbon atoms, which adducts are converted with an organic dicarboxylic acid or with an inorganic polybasic acid into an acidic ester, (g) Agninsulfonates and (h) formaldehyde condensation products.

The dispersions can also include additional constituents, such as nonionic surfactants, other anionic and/or nonionic compounds, customary commercial antifoams, preservatives and antifreeze agents.

These dispersions are judiciously prepared by forming a paste from the compounds of the formula I and/or II with a dispersant, for example with the acidic ester and water, in a mixer and dispersing this paste, with the addition if appropriate of the desired additional constituents such as nonionic surfactants, other anionic and/or nonionic compounds, including the antifoams, preservatives and antifreeze agents, for from 1 to 30 hours, preferably from 1 to 10 hours. The dispersing operation is advantageously conducted by the action of high shear forces, for example by milling in a ball mill, sand mill or bead mill. After milling it is possible to add an aqueous solution of a customary commercial stabilizer or thickener and, if desired, more water, after which stirring is carried out until distribution is homogeneous.

The compounds of the formulae I or II are admixed in the form of their aqueous dispersions to the printing pastes.

The printing paste here contains the corresponding compound of the formula I or II in amounts from 0.5 to 8%, preferably from 1 to 2%, based on the weight of the printing paste. Examples of suitable fibre materials are acid-modified polyester fibres and, in particular, linear polyester fibres. Linear polyester fibres are synthetic fibres obtained, for example, by condensing terephthalic acid with ethylene glycol or isophthalic acid or terephthalic acid with 1,4-bis (hydroxymethyl)cyclohexane, and copolymers of terephthalic and isophthalic acid and ethylene glycol. The linear polyester employed almost exclusively to date in the textile industry consists of terephthalic acid and ethylene glycol. Examples of acid-modified polyester fibres are polycondensation products of terephthalic acid or isophthalic acid, ethylene glycol and 1,2-dihydroxy-3- or 1,3-dihydroxy-2-(3-sodium sulfopropoxy)propane, 2,3-dimethylol-1-(sodium sulfopropoxy)butane, 2,2-bis(3-sodium sulfopropoxyphenyl)propane or 3,5-dicarboxybenzenesulfonic acid and/or sulfonated terephthalic acid, sulfonated 4-methoxybenzenecarboxylic acid or sulfonated biphenyl-4,4'-dicarboxylic acid.

The disperse dyes are dyes from various classes which are of low or zero solubility in water, examples being nitro dyes, aminoketone dyes, ketonimine dyes, methine dyes, nitrodiphenyl dyes, quinoline dyes and, in particular, anthraquinone dyes or azo dyes, such as monoazo dyes or disazo dyes. It is also possible to employ mixtures of different disperse dyes.

However, it is advantageous to use the dye (extended or unextended) not as it is but as an aqueous preparation comprising the dye (or dye mixtures) which is of low or zero solubility in water. Particularly suitable such aqueous preparations are those described in DE-A-2 850 482.

The amount of dyes to be added to the printing paste depends on the desired colour strength; amounts which have proven to be appropriate are in general from 0.01 to 15, preferably from 0.02 to 10 per cent by weight, based on the textile material employed.

In addition to the dyes and the aqueous dispersion comprising the compound of the formula I or II, the printing pastes judiciously include acid-stable thickeners, preferably of natural origin, such as flour derivatives, especially sodium alginate, on its own or as a mixture with modified cellulose, in particular with preferably from 20 to 25 per cent by weight of carboxymethylcellulose. If desired, the printing pastes may also include acid donors, such as butyrolactone or sodium hydrogen phosphate, preservatives, sequestering agents, emulsifiers, water-insoluble solvents, oxidizing agents or deaerating agents.

Particularly suitable preservatives are formaldehyde donors, for example paraformaldehyde and trioxane, especially aqueous formaldehyde solutions with strengths of from about 30 to 40 per cent by weight; examples of suitable sequestering agents are sodium nitrilotriacetate, sodium ethylenediaminetetraacetate, and especially sodium polymetaphosphate, especially sodium hexametaphosphate; particularly suitable emulsifiers are adducts of an alkylene oxide and a fatty alcohol, in particular an adduct of oleyl alcohol and ethylene oxide; suitable water-insoluble solvents are high-boiling saturated hydrocarbons, especially paraffins with a boiling range from about 160 to 210° C. (so-called painters' and varnish-makers' spirits); a suitable example of an oxidizing agent is an aromatic nitro compound, especially an aromatic mono- or dinitrocarboxylic acid or -sulfonic acid, possibly present in the form of an alkylene oxide adduct, especially a nitrobenzenesulfonic acid, and examples of suitable deaerating agents are high-boiling solvents, especially terpentine oils, higher alcohols, preferably $C_8$- to $C_{10}$alcohols, terpene alcohols or deaerating agents based on mineral oils and/or silicone oils, especially commercial formulations comprising from about 15 to 25 per cent by weight of a mineral oil and silicone oil mixture and from about 75 to 85 per cent by weight of a $C_8$alcohol such as, for example, 2-ethyl-n-hexanol.

In the printing of the fibre materials, the printing paste is applied directly to parts or to all of the fibre material, judiciously employing printing machines of customary construction, for example intaglio printing, rotary screen printing and flat-film printing machines.

After printing, the fibre material is dried at temperatures of up to 150' C., preferably from 80 to 120° C.

Subsequent fixing of the fibre material is usually conducted by dry heat (thermofixing) or with superheated steam under atmospheric pressure (HT fixing). Fixing is carried out under the following conditions:

HT fixing: 4 to 8 minutes at 170 to 180° C.

Thermofixing: 1 to 2 minutes at 200 to 230° C.

The prints are finished likewise in conventional manner by washing with water followed by an optional reductive afterclear in alkaline medium, for example with sodium dithionite. In the latter case, the prints are again washed and dried.

The present process is also suitable for transfer printing. For this utility the printing paste is applied to the entire surface of the support, preferably in a patterned arrangement, judiciously using printing machines of conventional construction, such as rotary screen printing and intaglio printing machines.

The support employed in the transfer printing technique is conveniently a flexible, preferably dimensionally stable ribbon, strip or sheet with a smooth surface. The support must be heat-stable and inert, i.e. have no affinity for the various components of the printing paste. It may consist of various materials, for example of metal, such as an aluminium or steel sheet, plastic, paper or a planar textile material, which materials may be coated with a film of vinyl resin, ethylcellulose or polyurethane resin. For reasons of cost, paper webs are principally used.

After the printing paste has been applied, the printed support is dried at from about 80 to 150° C., in particular from 80 to 120° C., for about 5 to 20 seconds. The actual transfer printing is conducted batchwise on a press or continuously in a conventional thermal printing unit at from 160 to 250° C., in particular from 190 to 220° C. The contact time is dependent on the set temperature and is between 20 and 60, preferably between 30 and 45 seconds at 230° C. and is carried out under pressure, the dye transferring from the support onto the printed fibre material.

After the heat and pressure treatment has been concluded, the printed fibre material is removed from the support. Normally neither an aftertreatment, i.e. generally a steam treatment, to fix the dye, nor a washing step to improve the fastness properties, is required.

The present process makes it possible to obtain on the fabric strong, wash-fast and rub-fast prints with a good white ground, the prints being distinguished by high light fastness with high stability of the fibre material.

The compounds of the formula I and/or II according to the invention can also be used in sunscreen compositions for pharmaceutical or cosmetic use whose purpose is to protect the human skin. Compounds which have proven to be particularly judicious are those which are present in the sunscreen composition in a very finely divided state (particle size <0.005 mm), the preferred particle size being in the range from 0.02 to 2 and, in particular, from 0.05 to 1.5, especially from 0.1 to 1.0 $\mu$. This desired particle size can be obtained by means of various conventional methods, for example by grinding the insoluble, coarse particles of the compounds of the formulae I or II in the presence of suitable milling assistants and using known milling devices, such as a jet mill, ball mill, vibrating mill or hammer mill, in particular a high-speed mixer or an impact mill, especially a rotating ball mill, vibrating mill, drum mill or rod mill. Milling is preferably carried out in the presence of from 0.1 to 30%, preferably from 0.5 to 15% by weight, based on the very finely divided insoluble organic compound I or II of a milling assistant. Examples of suitable such milling assistants are alkylated vinylpyrrolidone polymer, the vinylpyrrolidone-vinyl acetate copolymer, acyl glutamate, an acrylate tert-octylpropenamide copolymer, a ditolyl ether sulfonic acid-formaldehyde condensate, a Carbomer, a conventional commercial mixture of fatty acid esters comprising a nonionic prehardener, for example tristyrylphenol ethoxylate, in particular a phosphatide (of natural or synthetic origin).

Under the influence of light the compounds of the formula I or II do not exhibit the tendency of generating free radicals which might destroy the human skin or sensitize it. Furthermore, their insolubility in sunscreen compositions means that they do not penetrate the skin, so that they are also unable to induce any unwanted allergy on the skin.

The very finely divided, insoluble compounds of the formula I and II can also be used together with one or more UV absorbers which are customarily used in cosmetic preparations for protecting the human skin against UV radiation.

The content of the very finely divided compounds of the formula I or II in the sunscreen composition is from about 0.1 to 15% by weight, preferably from 0.5 to 10% by weight, based on the overall composition; in some cases, other cosmetically permissible additives may also be present.

The sunscreen compositions can be prepared by physical mixing of the very finely divided, insoluble compounds I or II and additives by any conventional means, for example simply by mixing these components together. However, it is also possible to mill a mixture of a coarse compound of the formula I or II the milling assistant and the grinding media until the coarse compound is in the very finely divided form. After removing the grinding media, for example quartz sand or glass balls, by filtration, the filtrate, containing the very finely divided compound of the formula I or II and milling assistant, can be mixed with the cosmetically permissible additives.

The sunscreen compositions can be in liquid form as a water-in-oil or oil-in-water formulation, as a cream or milk, as an oil, or as an oil-alcohol lotion; or else in gel form or in solid form, such as in stick form, or as an aerosol formulation.

If the sunscreen composition is present in the form of a water-in-oil or oil-in-water emulsion, then the cosmetically permissible additive preferably contains from 5 to 50% of an oil phase, from 5 to 20% of an emulsifier and from 30 to 90% by weight of water.

The oil phase can comprise any oil which is suitable for cosmetic formulations, for example one or more hydrocarbon oils, wax, natural oil, silicone oil, a fatty acid ester or a fatty alcohol. Preferred monools or polyols are ethanol, isopropanol, propylene glycol, hexylene glycol, glycerol and sorbitol.

The emulsifier can be any emulsifier commonly employed in cosmetic formulations, for example one or more ethoxylated esters of a natural oil derivative, such as a polyethoxylated ester of a hydrogenated castor oil, a silicone oil emulsifier, such as a silicone polyol; an unmodified or ethoxylated fatty acid soap; an ethoxylated fatty alcohol; an unmodified or ethoxylated sorbitan ester; an ethoxylated fatty acid, or an ethoxylated glyceride.

The sunscreen composition can include further known additives having a useful effect. Examples of such additives are emollients, skin moisteners, tanning accelerators, emulsion stabilizers, thickeners such as xanthan, moisture retention agents such as glycerol, film formers, preservatives, fragrances and colourants.

Sunscreen compositions of this kind afford excellent protection to the human skin against the damaging effect of sunlight and allow unendangered tanning of the skin. Furthermore, they have a water-repelling effect.

The invention additionally provides coating compositions containing from 0.1 to 10% by weight of a polyoxyalkylene substituted and/or bridged triazine, benzotriazole and benzophenone derivative of the formula I or II and, optionally as further components, solvents, pigments, dyes, plasticizers, antioxidants, stabilizers, thixotropic agents, levelling assistants and/or other light stabilizers, metal passivators, phosphites or phosphonites, and for the use of such coating compositions as topcoat, and a stabilized organic material, especially organic polymer material, which contains at least 0.1 to 10.0% by weight of a polyoxyalkylene substituted and/or bridged triazine, benzotriazole and benzophenone derivative of the formula I or II, this material being in particular a polyester, hot-crosslinkable acrylic resin, thermoplastic acrylic resin, polyamide, MF or UF resin, or a polyurethane, and also a stabilized coating material based on one or more polymers, and a stabilized organic material which is in the form of photo material or is part of a photo material, the photo material containing, preferably in the top layer and the intermediate layer, from 0.1 to 5.0% by weight of at least one polyoxyalkylene substituted and/or bridged triazine, benzotriazole and benzophenone derivative of the formula I or II.

The invention additionally provides a process for preparing a stabilized material, especially an organic, polymeric material, by adding at least one polyoxyalkylene substituted and/or bridged triazine, benzotriazole and benzophenone derivative of the formula I or II to the organic material.

The preparation or the synthesis of the novel, polyoxyalkylene substituted and bridged triazine, benzotriazole and benzophenone derivatives is carried out by various known techniques.

Examples of procedures for preparing the novel, polyoxyalkylene substituted and bridge triazine, benzotriazole and benzophenone derivatives of the formulae I and II and the starting compounds, are as follows:

a) Starting compounds:

The diglycidyl ether of the formula (A)

(A)

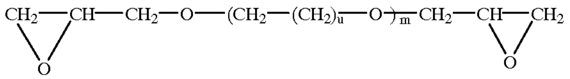

is obtained by reacting polyalkylene glycol (for example polyethylene glycol, polypropylene glycol or polytetrahydrofuran [Terathan®]) of the formula (B)

$$HO—(CH_2—(CH_2)_u—O—)_m—H \quad (B),$$

which is known and is commercially available, with epichlorohydrin in the presence of a base (e.g. NaOH or KOH) and of a phase transfer catalyst (for example tetraalkylammonium bromide or chloride, such as tetra-n-butylammonium bromide=TBAB) at a temperature of about 20° C.–100° C., preferably 30° C.–50° C.

Compounds of the formula A in which u is 3 to 4, especially 3, and m is as defined above are novel and are likewise provided by the invention.

The polyalkylene glycol bis(chlorocarbonylalkyl) ether of the formula (C)

(C)

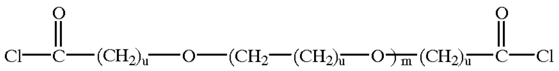

is obtained by chlorination of the polyalkylene glycol biscarboxyalkyl ether of the formula (D)

(D)

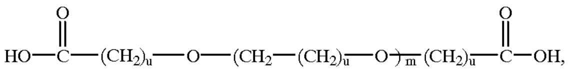

which is known and is commercially available, with a chlorinating agent (such as thionyl chloride) in an aprotic organic solvent (e.g. tetrahydrofuran (THF), dioxane, hexane, heptane, cyclohexane, toluene or xylene) in the presence of catalytic amounts of dimethylformamide at a temperature of 30° C.–80° C., preferably 50° C–80° C.

The polyalkylene glycol di(alkoxycarbonylalkyl) ether of the formula (E)

(E)

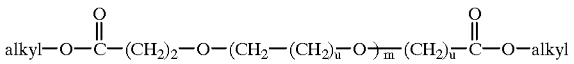

in which alkyl has 1 to 4, preferably 1 to 2 carbon atoms, is obtained either by esterifying 1 mol of the polyalkylene glycol bis(chlorocarbonylalkyl) ether of the formula (C) with 2 mol of an alcohol (alkyl-OH), 2 mol of pyridine in a solvent (for example methylene chloride) at a temperature of 20° C. to 30° C., or by esterifying 1 mol of the polyalkylene glycol bis(chlorocarbonylalkyl) ether of the formula (C) with an excess of alcohol (alkyl-OH) in a solvent (e.g. toluene or xylene) and with an acid catalyst (for example sulfuric acid or toluenesulfonic acid).

The diester of the formula (F)

(F)

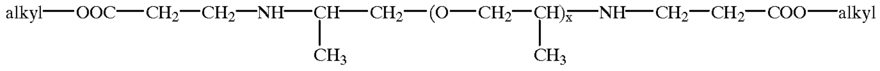

is obtained by a Michael addition of 2 mol of an alkyl acrylate of the formula (G)

$$alkyl\text{-}OOC—CH{=}CH_2 \quad (G)$$

in which alkyl has 1 to 4, preferably 1 to 2 carbon atoms, and which is known, onto 1 mol of a diamine of the formula ($H_1$)

($H_1$)

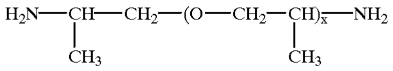

in which x is the range of numbers from 2 to 68, preferably 2 to 35, and which is likewise known (Jeffamine® D series; see in particular the publication Jeffamine® of polyoxyalkylene-amines by TEXACO Chemical Company and U.S. Pat. No. 5,210,195).

Instead of the abovementioned diamine of the Jeffamine® D series it is also possible to use diamines of the Jeffamine® ED series of the formula ($H_2$)

($H_2$)

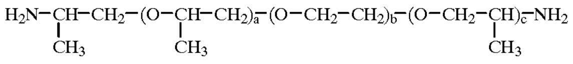

in which a+c=2.5 and b is the range of numbers from 8.5–86.0, preferably 8.5–40.5, or a+c is the range of numbers from 2 to 33 and b=0, or diamines of the Jeffamine® EDR series, of the formula ($H_3$)

$$H_2N(CH_2—CH_2—O)_n—CH_2—CH_2—NH_2 \quad (H_3)$$

in which n is the number 2 or 3.

The polyalkylene glycol monoglycidyl ether of the formula (I)

(I)

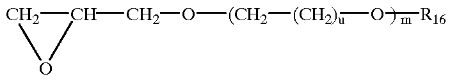

is obtained from the polyalkylene glycol monoalkyl ether of the formula (K)

$$OH—(CH_2—(CH_2)_u—O—)_m—R_{16} \quad (K),$$

which is known and is commercially available, by reaction with epichlorohydrin in the presence of a base (e.g. NaOH) at a temperature of 20° C. to 100° C., preferably 80° C.

In a procedure analogous to the reactions of the compound (D) to form the compound (C) and (E) above, the compounds (L) and (M) of the formulae $$Cl—CO—(CH_2)_u—O—(CH_2—(CH_2)_u—O—)_m—R_{16} \quad (L)$$

and $$alkyl\text{-}O—CO—(CH_2)_uO—(CH_2—(CH_2)_u—O—)_m—R_{16} \quad (M)$$

respectively are obtained from the compound (N)

$$HO—CO—(CH_2)_u—O—(CH_2—(CH_2)_u—O—)_m—R_6 \quad (N)$$

Likewise, the compound (O) of the formula $$alkyl\text{-}O—CO—CH_2—CH_2—NH—(C_nH_{2n}—O—)_m—C_nH_{2n}—O—R_{16} \quad (O)$$

in analogy to the Michael addition of an alkyl acrylate of the formula (G) onto a diamine of the formulae ($H_1$), ($H_2$) or ($H_3$) above, is obtained by a Michael addition of an alkyl acrylate of the formula (G) onto a monoamine of the formula (P)

$$NH_2—(C_nH_{2n}—O—)_m—R_{16} \quad (P).$$

The monoamines of the formula (P) are known and are available under the trade name "Jeffamine® M series".

b) Mono-polyoxyalkylene substituted triazine, benzotriazole and benzophenone derivatives of the formula I For the mono-polyoxyalkylene substituted triazine, benzotriazole and benzophenone derivatives of the formula I there are various preparation options.

One option is to react 1 mol of a chromophoric compound of the formulae ($IIIA_1'$)

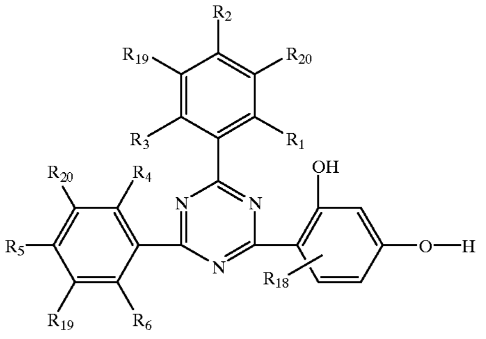

-continued ($IIIB_1'$)

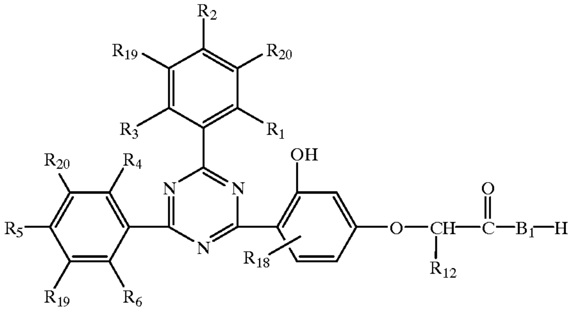

($IIIC_1'$)

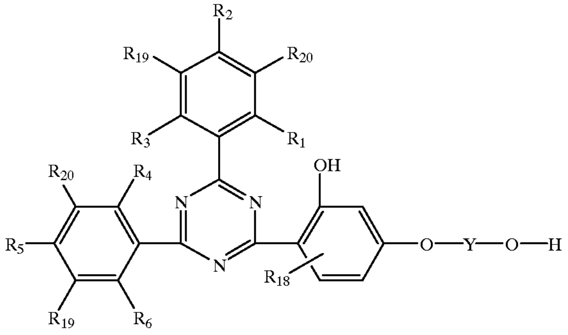

($IVA_1'$)

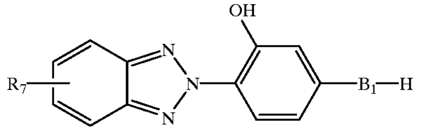

($IVB_1'$)

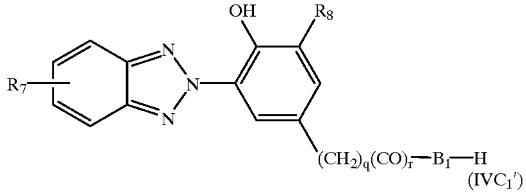

($IVC_1'$)

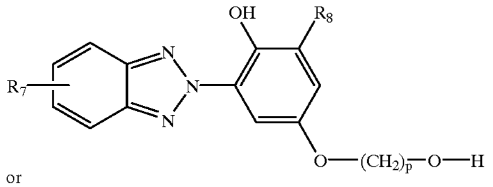

or ($VA_1'$)

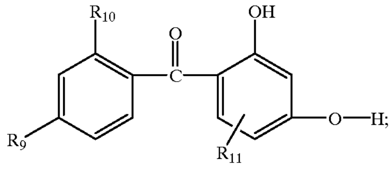

with 1 mol of a compound of the formulae I to P which introduces the polyoxyalkylene group.

This takes place, for example, by reacting 1 mol of a chromophoric compound of the formula $IIIA_1'$ with 1 mol of a polyalkylene glycol monoglycidyl ether of the formula (I) in a solvent (e.g. mesitylene or xylene) in the presence of a catalyst (for example ethyltriphenylphosphonium bromide or dimethylbenzylamine) in a temperature range from about 120° C. to 150° C., preferably 140° C., to give a mono-polyoxyalkylene substituted triazine derivative of the formula (F91)

(F91)

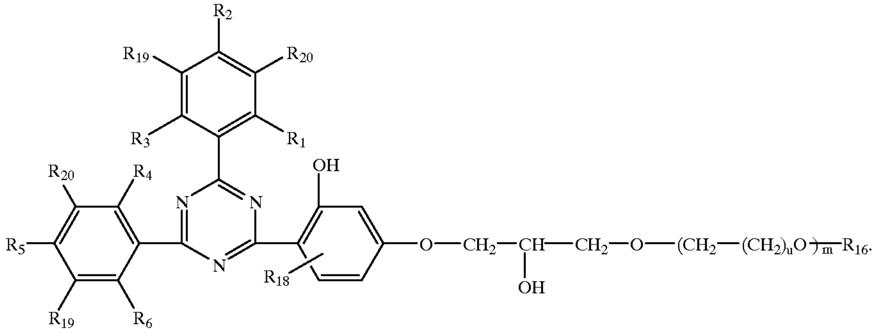

Another option is to esterify a chromophoric compound of the formula $IIIA_1$' in a first stage with an α-bromoalkyl ester in the presence of a base to give a compound of the formula (F92)

(F92)

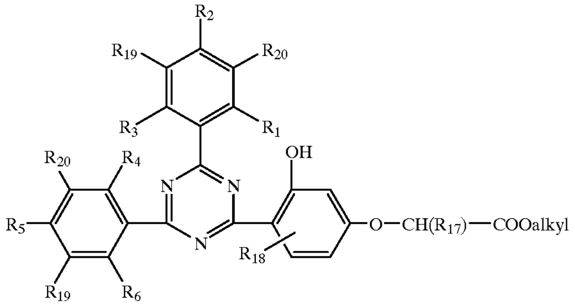

in which alkyl is an alkyl radical of 1 to 6, preferably 1 to 2 carbon atoms, and to react this ester in a second stage with 1 mol of a monofunctional polyalkylene glycol monoalkyl ether of the formula (K) in the presence of a catalyst (for example dibutyltin oxide, titanium tetraalkoxide or aluminium trialkoxide) in a temperature range of about 120° C.–160° C., preferably 120° C., to give a mono-polyoxyalkylene substituted triazine derivative of the formula (F93)

(F93)

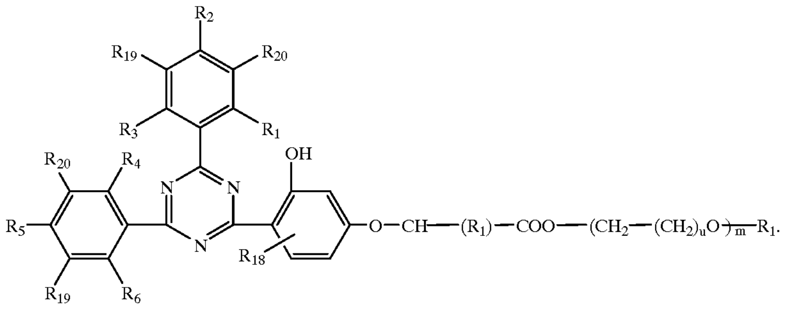

Yet another option is to react the abovementioned compound of the formula (F92) with a monoamine of the Jeffamine® M series (formula (P)) to give a mono-polyoxyalkylene substituted triazine derivative of the formula (F94)

(F94)

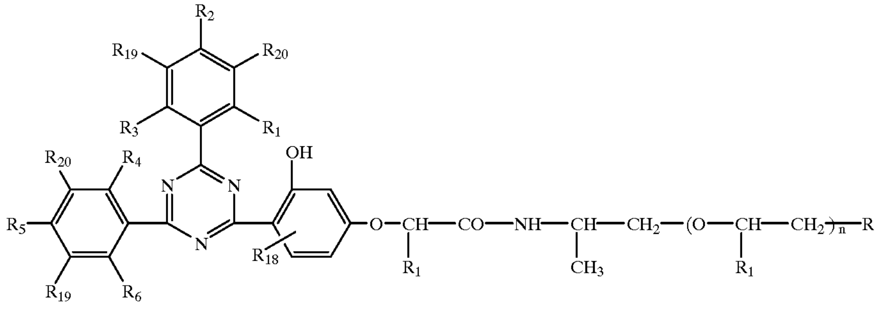

in which $R_1$ is H or $CH_3$, n=the range of numbers 2–41, preferably 9–41, and R is $C_1$–$C_4$alkoxy or $C_1$–$C_4$alkoxyethoxy, especially methoxy or methoxyethoxy.

c) Polyoxyalkylene bridged triazine, benzotriazole and benzophenone derivatives of the formula II Starting compounds are:

i) Chromophoric compounds of the formulae $IIIA_1'$, $IVA_1'$ and $VA_1'$, which contain a phenolic OH group. Such compounds are known and are described in the case of benzotriazole, for example, in U.S. Pat. No. 3,072,585.

By reacting 2 mol of a compound of the formulae $IIIA_1'$, $IVA_1'$ or $VA_1'$, containing a phenolic OH group, with 1 mol of a diglycidyl ether of the formula (A) in a solvent (e.g. toluene, xylene or mesitylene), in the presence of a catalyst (e.g. ethyltriphenylphosphonium bromide or dimethylbenzylamine) in a temperature range of 100° C.–160° C., especially 120° C.–160° C., a polyoxyalkylene bridged triazine, benzotriazole or benzophenone compound is obtained of the formula

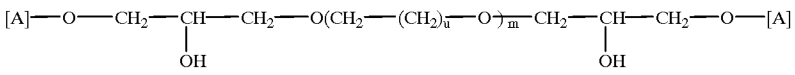

in which each A denotes alternatively the triazine radicals of the formula (F95)

(F95)

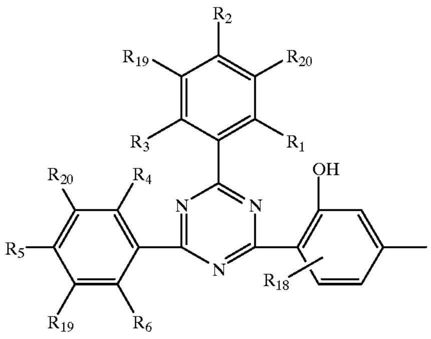

or the benzotriazole radicals of the formula (F96)

(F96)

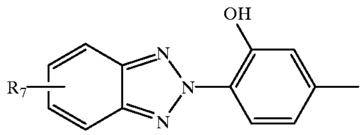

or the benzophenone radicals of the formula (F97)

(F97)

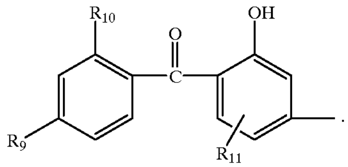

The reaction of 2 mol of a compound of the formulae $IIIA_1'$, $IVA_1'$ or $VA_1'$, containing a phenolic OH group, with 1 mol of polyalkylene glycol bis(chlorocarbonylalkyl) ether of the formula (C) in a solvent (e.g. toluene or diethylene glycol dimethyl ether [diglyme]) in the presence of a catalyst (e.g. pyridine) in a temperature range of about 20° C.–100° C., preferably 60° C–80° C., leads to polyoxyalkylene bridged triazine, benzotriazole and benzophenone derivatives of the formula (F98)

$$[A]—O—CO—(CH_2)_u—O—(CH_2—(CH_2)_u—O—)_m—(CH_2)_u—CO—O—[A] \quad (F98)$$

in which each A denotes the above-indicated structure of the formula (F95), (F96) or (F97), respectively.

The reaction of 1 mol of a compound of the formulae $IIIA_1'$, $IVA_1'$ or $VA_1'$, containing a phenolic OH group, with an α-bromoalkyl ester of the formula (F98)

(F98)

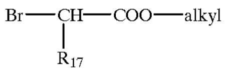

in a solvent (e.g. diglyme) in the presence of a base (e.g. $K_2CO_3$) at a temperature of about 100° C. gives an ester of the formula (F99)

(F99)

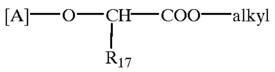

in which formulae alkyl has 1 to 6, in particular 1 to 2, carbon atoms, $R_{17}$ is as defined at the outset and A has the above-indicated structures (F95, F96 or F97, respectively).

2 mol of the abovementioned ester of the formula (F99), which is known, when reacted with 1 mol of polyalkylene glycol of the formula (B) in the presence of a catalyst (e.g. titanium tetraalkoxide, dibutyltin oxide, aluminium trialkoxide or lithium amide) by transesterification, give rise to bridged triazine, benzotriazole and benzophenone derivatives of the formula (F100)

(F100)

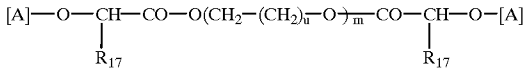

in which each A has the above-indicated structure (F95, F96 or F97, respectively).

By reacting 2 mol of said ester of the formula (F99) with 1 mol of a diamine of the formula ($H_1$), ($H_2$) or ($H_3$), respectively, in the presence of a catalyst (e.g. lithium amide, sodium methoxide) in a temperature range of about 80° C.–230° C., preferably 110° C.–230° C., bridged triazine, benzotriazole and benzophenone derivatives are obtained which are of the formula (F101)

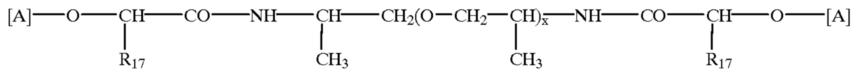

or (F102)

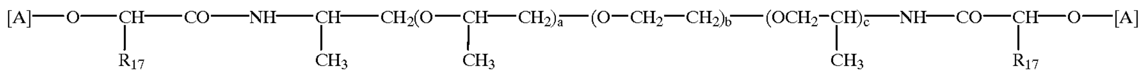

or (F103)

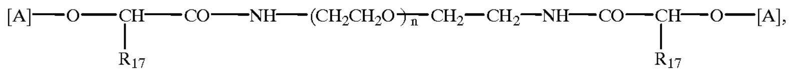

respectively, in which each A has the above-indicated structure (F95, F96 or F97, respectively).

By alkylating the chromophoric compounds of the formulae $IIIA_1'$, $IVA_1'$ or $VA_1'$, which contain a phenolic OH group, with, for example, an alkylene oxide such as butylene oxide, with ω-bromo alcohols or with alkyl glycidyl ethers whose alkylene or alkyl radical is of 2–20 carbon atoms in a solvent (e.g. toluene, xylene or mesitylene) in the presence of a catalyst (such as ethyltriphenylphosphonium bromide or dimethylbenzyl amine) in a temperature range of about 120° C.–180° C. and possibly in an autoclave, compounds are obtained which are of the formula (F104)

[A]—O—Y—OH (F104)

in which A has the above-indicated structures (F95, F96 or F97) of triazine, benzotriazole or benzophenone, respectively, and Y is as defined at the outset. These compounds (F 104) are known and in the case of benzotriazole, for example, are described in U.S. Pat. No. 5,147,902. By reacting 2 mol of said compound of the formula (F104) with 1 mol of a diester of the formula F in the presence of a catalyst (e.g. titanium tetraalkoxide, such as titanium tetrabutoxide, aluminium trialkoxide or dibutyltin oxide) by transesterification in a temperature range of about 110° C.–230° C., preferably 110° C.–180° C., compounds are obtained which are of the formula (F 105)

(F105)

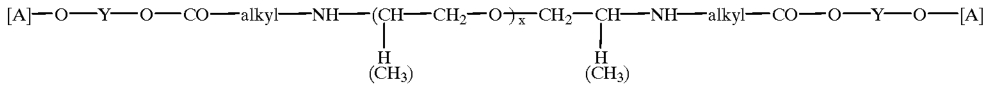

in which each A denotes the above-indicated structures (F95, F96 or F97) of triazine, benzotriazole or benzophenone, respectively, Y is as defined at the outset, alkyl is of 1–4, especially 1–2 carbon atoms, and x denotes the range of numbers from 2 to 68, in particular from 2 to 35.

By reacting 2 mol of said compound of the formula (F104) with 1 mol of a polyalkylene glycol bis (chlorocarbonylalkyl) ether of the formula (C) in a solvent (e.g. toluene, xylene or diglyme) in the presence of a catalyst (e.g pyridine) at a temperature of about 80° C.–120° C., preferably 50° C.–120° C., compounds are obtained which are of the formula (F106)

$$[A]—O—Y—O—CO(CH_2)_u—O(CH_2(CH_2)_u—O—)_m—(CH_2)_u—CO—O—Y—O—[A] \quad (F106)$$

in which each A denotes the above-indicated structures (F95, F96 or F97) of triazine, benzotriazole or benzophenone, respectively, and the other symbols are as defined.

(ii) Chromophoric compounds which contain an aliphatically attached COOH group and are of the formula ($IVB_1$') in which $B_1$ is oxygen; these compounds have the following structures (formulae F107):

(F107a)

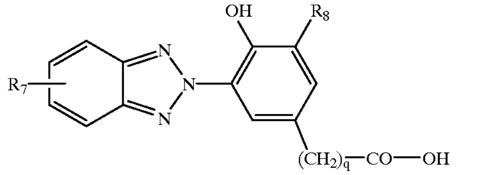

(F107b)

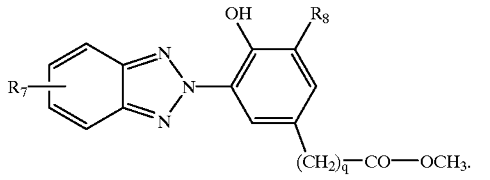

These compounds are known and can be prepared in a known manner, for example by hydrolysis of the corresponding esters.

By amidating 2 mol of this ester with 1 mol of diamine of the formula ($H_1$), ($H_2$) or ($H_3$), polyoxyalkylene bridged benzotriazole compounds are obtained whose benzotriazole radical is of the formula

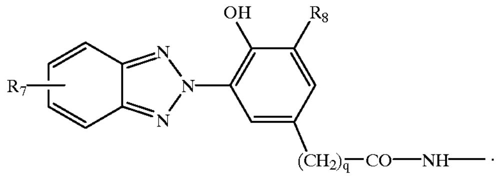

By reacting 2 mol of the compound of the formula (F107a) with 1 mol of a diglycidyl ether of the formula (A) in a solvent (e.g. toluene, xylene or mesitylene) in the presence of a catalyst (e.g. ethyltriphenylphosphonium bromide or dimethylbenzylamine) in a temperature range of about 100° C.–160° C., preferably 120° C.–160° C., polyoxyalkylene bridged benzotriazole compounds are obtained which are of the formula (F108)

(F108)

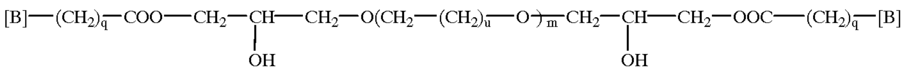

in which B is the benzotriazole radical of the formula (F109)

(F109)

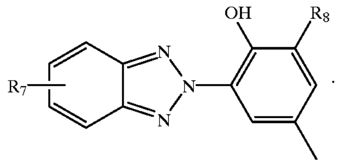

By alkylating the compounds of the formula (F107a or F107b) with ω-bromo alcohols, alkylene oxides or with alkyl glycidyl ethers, in analogy to the earlier alkylation of the chromophoric compounds of the formulae $IIIA_1$', $IVA_1$' or $VA_1$', compounds are obtained which are of the formula (F110)

(F110)

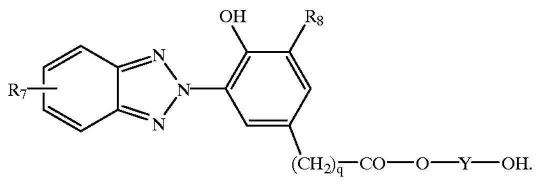

By esterifying the compound (F110) with compounds of the formulae (C) and (E), polyoxyalkylene bridged benzotriazole derivatives are obtained which are of the formula $$[B]—O—Y—O—CO—(CH_2)_u—O—(CH_2—(CH_2)_u—O—)_m—(CH_2)_u—CO—O—Y—O—[B]$$

in which B is the benzotriazole radical of the formula (F111)

(F111)

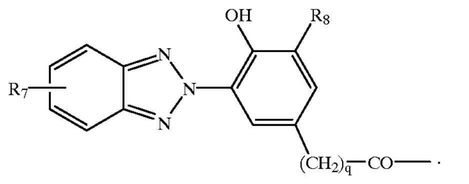

By transesterifying the compound of the formula (F110) with a diester of the formula (F), compounds are obtained which are of the formula (F112)

$$[B]—O—Y—O—CO—CH_2—CH_2—NH—(C_nH_{2n}O—)_m—C_nH_{2n}—NH—CH_2—CH_2—COOY—O—[B] \quad (F112)$$

in which B is the benzotriazole radical of the formula (F111).

iii) Chromophoric compounds which contain an aliphatically attached OH group and are of the formula $IVB_1$' (in which r=zero) and $IVC_1$'.

The esterification of these compounds with the compound (C) or (E) leads, for example, to polyoxyalkylene bridged benzotriazole compounds of the formula $$[B]—O—C(O)(CH_2)_u—O(CH_2)_u—O—)_m—(CH_2)_uC(O)—O—[B]$$

in which B is the benzotriazole radical of the formula (F113)

(F113)

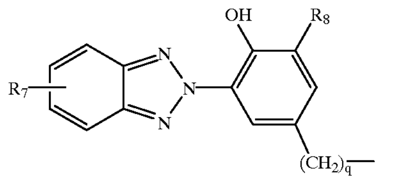

-continued (F114)

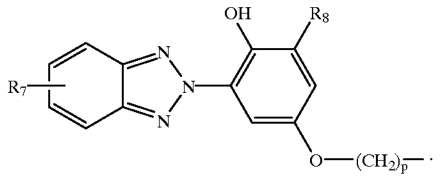

The hydroxy compounds of the formula (F114) are known and are described, for example, in JP 74-68436 and can be prepared in a known manner.

The examples which follow illustrate the invention without limiting it thereto. Where the formulae contain indices that are not integral, these indices correspond to the average value in the mixture of compounds in question. The use of mixtures of precursors with different degrees of polymerization leads, therefore, to products with a non-integral "m".

EXAMPLE 1

Polyethylene glycol α-methyl ω-glycidyl diether 405

12.0 g (0.30 mol) of pulverized sodium hydroxide in 105.1 g (0.30 mol) of polyethylene glycol monomethyl ether 350 (average molecular weight=350) are stirred at about 80° C. for about 3 hours, during which the sodium hydroxide is almost completely dissolved. After cooling to about 25° C., 83.2 g (0.90 mol) of epichlorohydrin (FLUKA, 99.5%) are added to the brown solution with vigorous stirring. An exothermic reaction is observed, and the temperature is held below 40° C. by occasional cooling with an ice bath.

After an hour, the mixture is heated at 75° C. for about 2 hours. After cooling to 50° C., the solid (NaCl) is filtered off and pressed dry. The filtrate is distilled at 110° C./15 mm Hg and then at 110° C./0.5 mm Hg in order to remove the excess epichlorohydrin and water. The residue is filtered to remove the solid particles. 106.2 g (89.3% yield) of polyethylene glycol α-methyl ω-glycidyl diether 405 (average molecular weight=405.29) are obtained as a weakly viscous, pale yellow liquid (for constitution of this glycidyl ether see Example 8, Tab. 1).

An analogous method is used to obtain the polyalkylene glycol α-methyl ω-glycidyl ethers designated in Table 1. The physical data for these glycidyl ethers can be seen from Table 2.

TABLE 1

| | Precursor $HO—(CH_2—CH_2—O—)_m—R_{16}$ | Polyalkylene glycol α-alkyl ω-glycidyl ethers 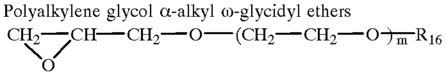 |
|---|---|---|
| Ex. | m | $R_{16}$ |
| 2 | 2 | $CH_3$ |
| 3 | 2 | $C_2H_5$ |
| 4 | 2 | $n-C_4H_9$ |
| 5 | 3 | $CH_3$ |
| 6 | 3 | $C_2H_5$ |
| 7 | 3 | $n-C_4H_9$ |
| 8 | 7.2 | $CH_3$ |
| 9 | 11.8 | $CH_3$ |
| 10 | 16.3 | $CH_3$ |

TABLE 2

Physical data of the polyalkylene glycol α-alkyl ω-glycidyl ethers of Table 1

| Ex. No. | Boiling point | Empirical formula (mol. wt.) | Analysis b[2]) g[3]) | C in % | H in % | Epoxide content b[2]) g[3]) | mol/kg mol/kg |
|---|---|---|---|---|---|---|---|
| 2 | 103° C./ 3 mbar | $C_8H_{16}O_4$ (176.21) | c: | 54.53 | 9.15 | c: | 5.68 |
| | | | f: | 54.49 | 9.25 | f: | 5.58 |
| 3 | 65–75° C./ 0.35 mbar | $C_9H_{18}O_4$ (190.24) | c: | 56.82 | 9.54 | c: | 5.26 |
| | | | f: | 56.71 | 9.57 | f: | 5.06 |
| 4 | 88–90° C./ 0.2 mbar | $C_{11}H_{22}O_4$ (218.29) | c: | 60.53 | 10.16 | c: | 4.58 |
| | | | f: | 60.41 | 10.17 | f: | 4.37 |
| 5 | — | $C_{10}H_{20}O_5$ (220.27) | c: | 54.53 | 9.15 | c: | 4.54 |
| | | | f: | 54.30 | 9.19 | f: | 4.02 |
| 6 | 90–96° C./ 0.10 mbar | $C_{11}H_{22}O_5$ (234.29) | c: | 56.39 | 9.46 | c: | 4.26 |
| | | | f: | 56.27 | 9.13 | f: | 4.07 |
| 7 | 113° C./ 0.1 mbar | $C_{13}H_{26}O_5$ (262.35) | c: | 59.52 | 9.99 | c: | 3.81 |
| | | | f: | 59.31 | 10.07 | f: | 3.70 |
| 8 | Oil | $C_{18.4}H_{36.8}O_{9.2}$ (405.29) | c: | 54.53 | 9.15 | c: | 2.47 |
| | | | f: | 54.03 | 9.01 | f: | 2.06 |
| 9 | Oil | $C_{27.6}H_{55.2}O_{13.8}$ (607.94) | c: | 54.53 | 9.15 | c: | 1.64 |
| | | | f: | 54.40 | 9.07 | f: | 1.63 |
| 10 | Oil | $C_{36.6}H_{73.2}O_{18.3}$ (806.18) | c: | 54.53 | 9.15 | c: | 1.24 |
| | | | f: | 53.51 | 9.36 | f: | 1.00 |

The $^1H$ NMR ($CDCl_3$, 300 MHz) spectra are in agreement with the desired products.
[2])Calculated
[3])Found

EXAMPLE 11

Diethylene glycol α-methyl ω-[3-(4-(2,4-di(2',4'-dimethylphenyl)-1,3,5-triazin-6-yl)-3-hydroxyphenyloxy)-2-hydroxypropyl]diether A mixture of 20.0 g (0.050 mol) of 2,4-bis(2',4'-dimethylphenyl)-6-(2',4"-dihydroxyphenyl)-1,3,5-triazine (compound (I) of Tab. 3, in which $R_2$=$R_3$=$R_5$=$R_6$=$CH_3$), 9.75 g (0.055 mol) of diethylene glycol α-methyl ω-glycidyl diether (compound (II) of Tab. 3, in which $R_{16}$=$CH_3$ and m=2) and 1.87 g (0.005 mol) of ethyltriphenylphosphonium bromide (FLUKA, 97%) in 100 ml of xylene (isomer mixture, FLUKA) is heated with stirring at 120° C. for 16 hours, during which the yellow suspension turns into a reddish orange solution. After cooling, the solvent is removed on a rotary evaporator. The crude material is dissolved in 100 ml of ethyl acetate and filtered through a silica gel column (Ø=6 cm; H=5 cm; 230–400 mesh; silica gel 60). After elution with 300 ml of ethyl acetate, the solvent is removed on a rotary evaporator and the solid is dried at 135° C./0.5 mm Hg. 27.0 g (93.5% yield) of diethylene glycol α-methyl ω-[3-(4-(2,4-di(2',4'-dimethylphenyl)-1,3,5-triazin-6-yl-)-3-hydroxyphenyloxy)-2-hydroxypropyl] diether (Example 12, Tab. 3) are obtained as an orange-coloured resin.

Following the above procedure, the triazine derivatives designated in Tab 3, Examples 13 to 33, are obtained analogously.

TABLE 3

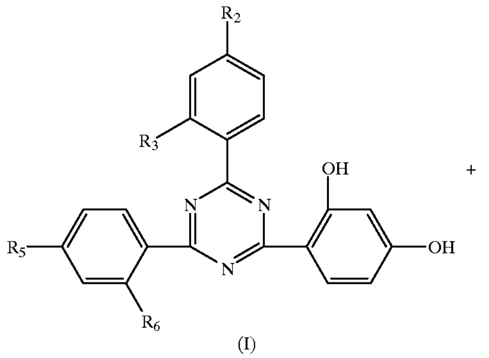

(I)

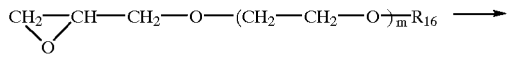

(II)

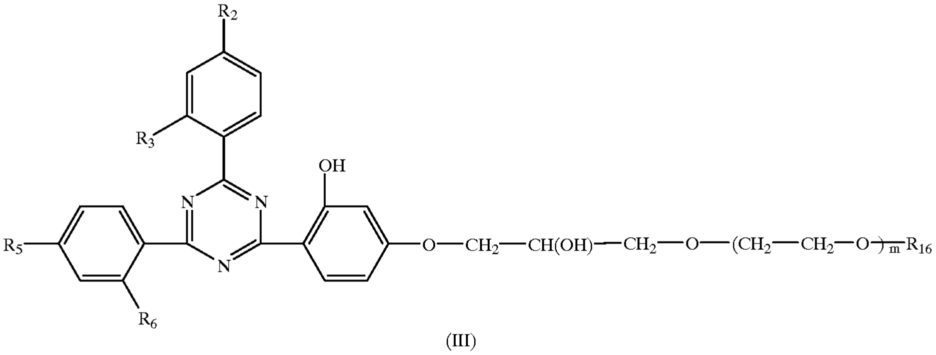

(III)

| Ex. No. | $R_2$ | $R_3$ | $R_5$ | $R_6$ | $R_{16}$ | m |
|---|---|---|---|---|---|---|
| 12 | $CH_3$ | $CH_3$ | $CH_3$ | $CH_3$ | $CH_3$ | 2 |
| 13 | $CH_3$ | $CH_3$ | $CH_3$ | $CH_3$ | $C_2H_5$ | 2 |
| 14 | $CH_3$ | $CH_3$ | $CH_3$ | $CH_3$ | n-$C_4H_9$ | 2 |
| 15 | $CH_3$ | $CH_3$ | $CH_3$ | $CH_3$ | $CH_3$ | 3 |
| 16 | $CH_3$ | $CH_3$ | $CH_3$ | $CH_3$ | $C_2H_5$ | 3 |
| 17 | $CH_3$ | $CH_3$ | $CH_3$ | $CH_3$ | n-$C_4H_9$ | 3 |
| 18 | $CH_3$ | $CH_3$ | $CH_3$ | $CH_3$ | $CH_3$ | 7.2 |
| 19 | $CH_3$ | $CH_3$ | $CH_3$ | $CH_3$ | $CH_3$ | 11.8 |
| 20 | $CH_3$ | $CH_3$ | $CH_3$ | $CH_3$ | $CH_3$ | 16.3 |
| 21 | H | H | H | H | $CH_3$ | 2 |
| 22 | H | H | H | H | $C_2H_5$ | 2 |
| 23 | H | H | H | H | n-$C_4H_9$ | 2 |
| 24 | H | H | H | H | $CH_3$ | 3 |
| 25 | H | H | H | H | $C_2H_5$ | 3 |
| 26 | H | H | H | H | n-$C_4H_9$ | 3 |
| 27 | H | H | H | H | $CH_3$ | 7.2 |
| 28 | H | H | H | H | $CH_3$ | 11.8 |
| 29 | H | H | H | H | $CH_3$ | 16.3 |
| 30 | Phenyl | H | Phenyl | H | $CH_3$ | 2 |
| 30a | Phenyl | H | Phenyl | H | n-$C_4H_9$ | 3 |
| 31 | Phenyl | H | Phenyl | H | $CH_3$ | 3 |
| 32 | Phenyl | H | Phenyl | H | $CH_3$ | 7.2 |
| 33 | Phenyl | H | Phenyl | H | $CH_3$ | 11.8 |

The physical data of some of these triazine derivatives of Tab. 3 are indicated in Table 4 below.

TABLE 4

| Ex. No. | Appearance | Tg in ° C. (DSC) | Empirical formula (Mol. wt.) | | C | H in % | N | UV (AcOEt) ε (max: 337 nm) ε (max: 228 nm) |
|---|---|---|---|---|---|---|---|---|
| 12 | orange-coloured resin | −12.8 | $C_{33}H_{39}N_3O_6$ | c: | 69.09 | 6.85 | 7.32 | 21 500 |
| | | | (573.69) | f: | 68.46 | 7.07 | 7.07 | 42 120 |
| 13 | orange-coloured resin | −18.7 | $C_{34}H_{41}N_3O_6$ | c: | 69.49 | 7.03 | 7.15 | 22 250 |
| | | | (587.72) | f: | 68.21 | 7.30 | 6.60 | 43 270 |
| 14 | orange-coloured resin | −22.0 | $C_{36}H_{45}N_3O_6$ | c: | 70.22 | 7.37 | 6.82 | 22 220 |
| | | | (615.77) | f: | 69.20 | 7.64 | 6.50 | 43 141 |
| 15 | orange-coloured resin | −24.0 | $C_{35}H_{43}N_3O_7$ | c: | 68.05 | 7.02 | 6.80 | 21 840 |
| | | | (617.75) | f: | 67.16 | 7.26 | 6.38 | 43 270 |
| 16 | pure yellow resin | −22.1 | $C_{36}H_{45}N_3O_7$ | c: | 68.44 | 7.18 | 6.65 | 22 290 |
| | | | (631.77) | f: | 68.16 | 7.37 | 6.30 | 43 214 |
| 17 | yellow resin | −23.8 | $C_{38}H_{49}N_3O_7$ | c: | 69.17 | 7.48 | 6.37 | 22 590 |
| | | | (659.83) | f: | 68.66 | 7.80 | 6.20 | 43 900 |
| 18 | resin | | $C_{43.4}H_{59.8}N_3O_{11.2}$ | c: | 69.94 | 7.51 | 5.23 | 21 250 |
| | | | (802.77) | f: | 63.37 | 7.68 | 4.49 | 40 900 |
| 19 | resin | | $C_{52.6}H_{78.2}N_3O_{15.8}$ | c: | 62.84 | 7.84 | 4.18 | 22 840 |
| | | | (1005.4) | f: | 61.50 | 7.83 | 3.72 | 43 750 |
| 20 | yellow wax | | $C_{61.6}H_{96.2}N_3O_{20.3}$ | c: | 61.47 | 8.06 | 3.49 | 20 760 |
| | | | (1203.7) | f: | 59.56 | 8.28 | | 40 130 |
| 27 | yellow wax | | $C_{39.4}H_{51.8}N_3O_{11.2}$ | | | | | 19 030 (340 nm) |
| | | | (746.67) | | | | | 38 270 (278 nm) |
| 28 | resin | | $C_{48.6}H_{70.2}N_3O_{15.8}$ | | | | | 17 810 (341 nm) |
| | | | (949.31) | | | | | 35 650 (278 nm) |
| 29 | yellow wax | | $C_{57.6}H_{88.2}N_3O_{20.3}$ | | | | | 18 290 (339 nm) |
| | | | (1147.55) | | | | | 35 710 (278 nm) |
| 30 | yellow | 107–110 | $C_{41}H_{39}N_3O_6$ | | | | | 65 900 (321 nm) |

TABLE 4-continued

| Ex. No. | Appearance | Tg in ° C. (DSC) | Empirical formula (Mol. wt.) | C | H in % | N | UV (AcOEt) ε (max: 337 nm) ε (max: 228 nm) |
|---|---|---|---|---|---|---|---|
| | solid | | (669.78) | | | | |
| 30a | yellow wax | | $C_{46}H_{49}N_3O_7$ (755.91) | | | | 62 900 (320 nm) |

EXAMPLE 34

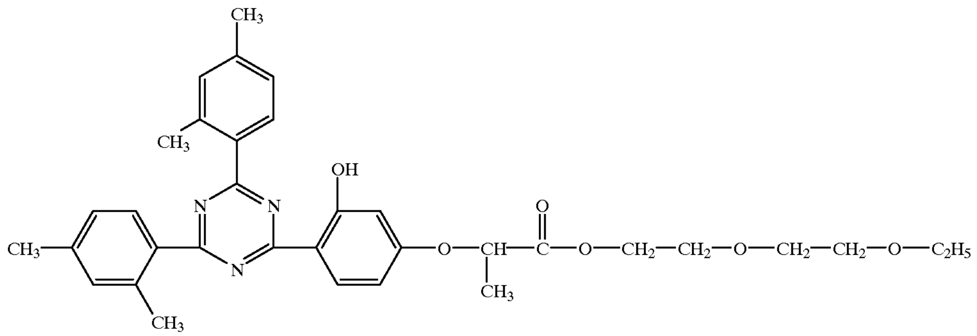

m = 2

A mixture of 2,4-bis(2',4'-dimethylphenyl)-6-(2"-hydroxy-4"-[(1-ethoxycarbonyl)ethoxy)phenyl)-1,3,5-triazine], diethylene glycol monoethyl ether and dibutyltin oxide is held at 120° C. for 16 hours, ethanol being stripped off using a Hickmann condenser. The mixture is concentrated on a rotary evaporator and the residue is placed on a silica gel column (Ø=6 cm, H=35 cm, silica gel 60, 230–400 mesh). It is eluted with ethyl acetate. After stripping off the solvent (150° C./0.1 mm), the compound of the above formula is obtained from the main fraction.

EXAMPLE 35

Following the procedure of Example 34 but using, instead of the 2,4-bis(2',4'-dimethylphenyl)-6-(2"-hydroxy-4"-[(1-ethoxycarbonyl)ethoxy)phenyl)-1,3,5-triazine], an equimolar amount of the triazine derivative of Table 5 below (compound I) and, instead of the diethylene glycol monoethyl ether of Example 34, an equimolar amount of the polyethylene glycol monoalkyl ether of Table 5 (compound II), a triazine derivative having a polyethylene glycol monoalkyl ether radical in accordance with Table 5 (compound III) is obtained.

TABLE 5

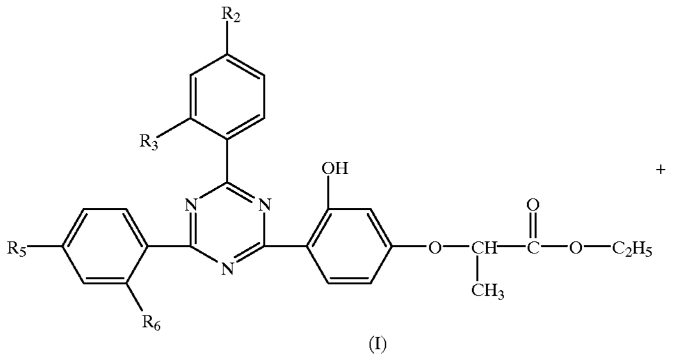

(I)

$HO-(CH_2-CH_2-O)_m-R_{16}$ ⟶

(II)

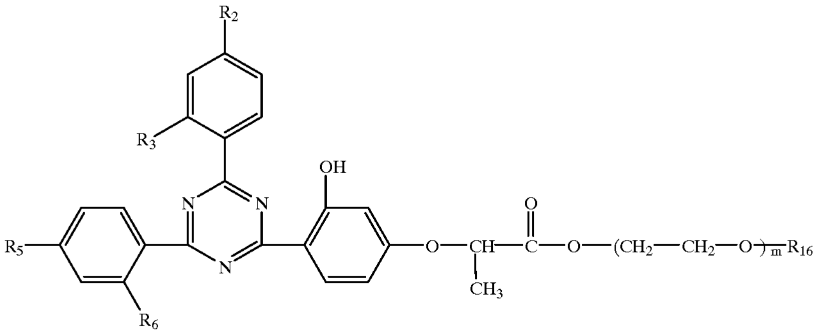

(III)

| Ex. No. | $R_2$ | $R_3$ | $R_5$ | $R_6$ | $R_{16}$ | m |
|---|---|---|---|---|---|---|
| 36 | $CH_3$ | $CH_3$ | $CH_3$ | $CH_3$ | n-$C_4H_9$ | 3 |
| 37 | $CH_3$ | $CH_3$ | $CH_3$ | $CH_3$ | $CH_3$ | 3 |
| 38 | $CH_3$ | $CH_3$ | $CH_3$ | $CH_3$ | $CH_3$ | 7.2 |
| 39 | $CH_3$ | $CH_3$ | $CH_3$ | $CH_3$ | $CH_3$ | 11.8 |
| 40 | H | H | H | H | $CH_3$ | 3 |
| 41 | H | H | H | H | $CH_3$ | 7.2 |
| 42 | H | H | H | H | $CH_3$ | 11.8 |
| 43 | Phenyl | H | Phenyl | H | $CH_3$ | 3 |
| 44 | Phenyl | H | Phenyl | H | $CH_3$ | 7.2 |
| 45 | Phenyl | H | Phenyl | H | $CH_3$ | 11.8 |

EXAMPLE 46

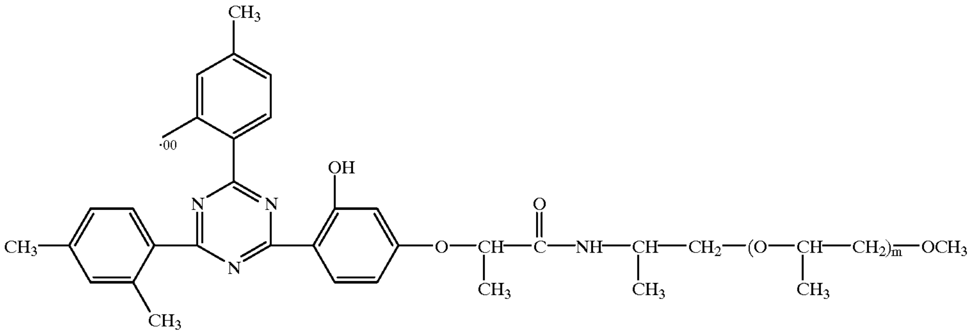

m=8.8

Following the procedure indicated in Example 34 but using, instead of the diethylene glycol monoethyl ether, equimolecular amounts of the monoamine of the formula

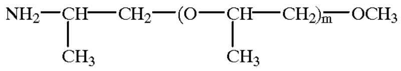

(m=8.8; Jeffamine® M series, M-600), the compound of the above formula is obtained.

EXAMPLE 47

Mixture of compounds of the formula

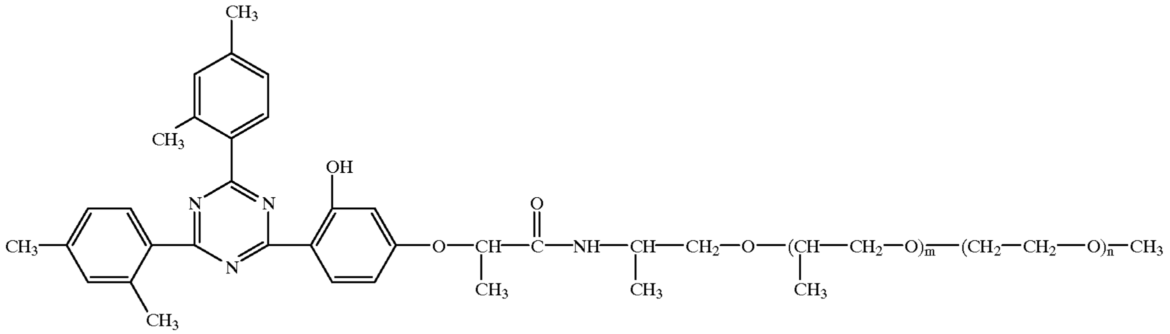

in which m is on average 10 and n is on average 31.

Following the procedure indicated in Example 34 but using, instead of the diethylene glycol monoethyl ether, equimolecular amounts of the monoamine of the formula

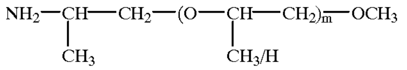

(in which m=41 and

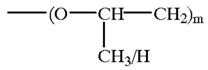

represents a mixture of 10 units

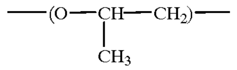

and 31 units —(—O—$CH_2$—$CH_2$)—; Jeffamine® M series, M-2070), the compound of the above formula is obtained.

EXAMPLE 48

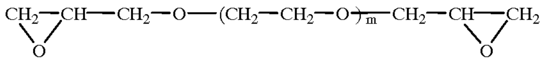

m = 8.7

The reaction is carried out under a nitrogen atmosphere.

42.0 g (1.05 mol) of pulverized NaOH (Merck, 99.0%) are added with stirring at a temperature of about 25° C. to a solution of 200 g (0.500 mol) of polyethylene glycol 400 (Fluka, Switzerland). An exothermic reaction is observed, during which the temperature rises to about 50° C. After cooling to about 25° C., 1.0 g (0.003 mol) of tetra-n-butylammonium bromide (TBAB, Fluka, 99%) is added with vigorous stirring and then 231.3 g (2.50 mol) of epichlorohydrin (Fluka 99.5%) are added in one portion. An exothermic reaction is observed, and the temperature is held, by cooling if necessary, at about 30° C. to 40° C. for about 2 hours.

After stirring for 2 hours more at 25° C., the solid is filtered off and washed with 20 ml of epichlorohydrin.

Excess epichlorohydrin and water are removed by evaporation at 80° C./50 mm to 20 mm Hg and finally at 100° C./0.15 mm Hg. The residue is filtered in order to separate out the solid. 238.6 g (92.9% yield) of diglycidyl ether of the above formula are obtained.

Analysis:

Appearance: pale brown oil $^1$H NMR ($CDCl_3$, 300 MHz): The spectrum is in agreement with the desired product.

Empirical formula: $C_{23.4}H_{44.8}O_{11.7}$ (molecular weight 513.41)

Analytical Data

| | C | H | Cl |
|---|---|---|---|
| Calculated: | 54.74 | 8.79 | 0.00% |
| Found: | 54.62 | 8.81 | <0.30% |

Epoxide content:

Calculated: 3.90 mol/kg

Found: 3.44 mol/kg

EXAMPLE 49

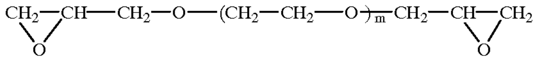

m = 2

Following the procedure of Example 48 and using, instead of polyethylene glycol 400, diethylene glycol, the diglycidyl ether of the above formula is obtained.

Analysis:

Appearance: colourless oil, boiling point 112°–117° C./0.30 mm Hg $^1$H NMR ($CDCl_3$, 300 MHz): The spectrum is in agreement with the desired product.

Empirical formula: $C_{10}H_{18}O_5$ (molecular weight 218.25).

Analytical Data

| | C | H | Cl |
|---|---|---|---|
| Calculated: | 55.03 | 8.31 | 0.00% |
| Found: | 55.31 | 8.22 | <0.30% |

Epoxide content:

Calculated: 9.16 mol/kg

Found: 8.71 mol/kg.

EXAMPLE 50

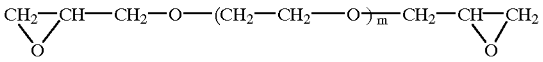

m = 3

Following the procedure of Example 48 and using, instead of polyethylene glycol 400, triethylene glycol (FLUKA), the diglycidyl ether of the above formula is obtained.

Analysis:

Appearance: pale yellow oil $^1$H NMR ($CDCl_3$, 300 MHz): The spectrum is in agreement with the desired product.

Empirical formula: $C_{12}H_{22}O_6$ (molecular weight 262.30)

Analytical Data

| | C | H | Cl |
|---|---|---|---|
| Calculated: | 54.95 | 8.45 | 0.00% |
| Found: | 54.71 | 8.46 | <0.30% |

Epoxide content:

Calculated: 7.63 mol/kg

Found: 6.05 mol/kg.

EXAMPLE 51

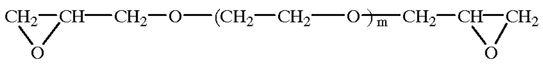

m = 4

Following the procedure of Example 48 and using, instead of polyethylene glycol 400, tetraethylene glycol (FLUKA), the diglycidyl ether of the above formula is obtained.

Analysis:

Appearance: brown oil $^1$H NMR ($CDCl_3$, 300 MHz): The spectrum is in agreement with the desired product.

Empirical formula: $C_{14}H_{26}O_7$ (molecular weight: 306.36)

Analytical Data

| | C | H | Cl |
|---|---|---|---|
| Calculated: | 54.89 | 8.55 | 0.00% |
| Found: | 54.69 | 8.57 | <0.30% |

Epoxide content:

Calculated: 6.53 mol/kg

Found: 5.25 Mol/kg.

EXAMPLE 52

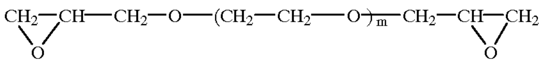

m = 6,4

Following the procedure of Example 48 and using, instead of polyethylene glycol 400, polyethylene glycol 300, the diglycidyl ether of the above formula is obtained.

Analysis:

Appearance: pale orange-coloured oil $^1$H NMR ($CDCl_3$, 300 MHz): The spectrum is in agreement with the desired product.

Empirical formula: $C_{18.8}H_{35.6}O_{9.4}$ (molecular weight: 412.09)

| | C | H | Cl |
|---|---|---|---|
| Calculated: | 54.80 | 8.70 | 0.00% |
| Found: | 54.79 | 8.79 | <0.30% |

Epoxide content:

Calculated: 4.85 mol/kg

Found: 4.09 mol/kg.

EXAMPLE 53

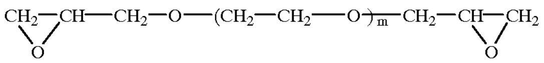

m = 13.2

Following the procedure of Example 48 and using, instead of polyethylene glycol 400, polyethylene glycol 600 (FLUKA), the diglycidyl ether of the above formula is obtained.

Analysis:

Appearance: pale brown oil $^1$H NMR ($CDCl_3$, 300 MHz): The spectrum is in agreement with the desired product.

Empirical formula: $C_{32.4}H_{62.8}O_{16.2}$ (molecular weight: 711.65)

Analytical Data

| | C | H | Cl |
|---|---|---|---|
| Calculated: | 54.68 | 8.89 | 0.00% |
| Found: | 54.48 | 8.93 | <0.30% |

Epoxide content:

Calculated: 2.81 mol/kg

Found: 2.44 mol/kg.

EXAMPLE 54

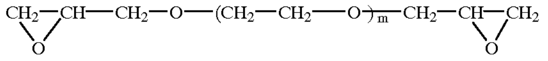

m = 22.3

Following the procedure of Example 48 using, instead of polyethylene glycol 400, polyethylene glycol 1000 (FLUKA), the diglycidyl ether of the above formula is obtained.

Analysis:

Appearance: pure red waxlike resin $^1H$ NMR ($CDCl_3$, 300 MHz): The spectrum is in agreement with the desired product.

Empirical formula: $C_{50.6}H_{99.2}O_{25.3}$ (molecular weight: 1112.53)

Analytical Data

| | C | H | Cl |
|---|---|---|---|
| Calculated: | 54.63 | 8.99 | 0.00% |
| Found: | 54.45 | 8.86 | <0.30% |

Epoxide content:

Calculated: 1,80 mol/kg

Found: 1.54 mol/kg.

EXAMPLE 55

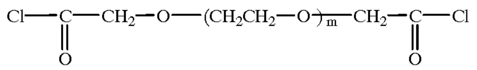

m = 10.6

The reaction is carried out under a nitrogen atmosphere.

59.5 g (0.500 mol) of thionyl chloride (>99%, from Fluka) are added with stirring at about 25° C. to a solution of 120.0 g (0.200 mol) of polyethylene glycol bis(carboxymethyl) ether (average MW=600, from Aldrich) in 100 ml of toluene (99.5%, from Merck) and 0.8 g (0.011 mol) of N,N-dimethylformamide (99.5%, from Fluka). A weakly exothermic reaction is observed, during which the temperature rises to about 30° C. This mixture is heated at a temperature of 50° C.–60° C., during which vigorous evolution of gas is observed.

The mixture is heated at a temperature of about 60° C. for about 1 hour and then held at about 80° C. for a further hour until the evolution of gas has ceased.

The solvent and excess thionyl chloride are removed on a rotary evaporator at 80° C./15 mm Hg and then at 75–80° C. /0.1 mm Hg.

The residue is filtered to remove solid particles, and 122.5 g (96.0% yield) of polyethylene glycol bis (chlorocarbonylmethyl) ether are obtained of the above formula (average molecular weight 638) as a pale yellow liquid.

Analysis:

Appearance: pale yellow oil $^1H$ NMR ($CDCl_3$, 300 MHz): The spectrum is in agreement with the desired product.

Empirical formula: $C_{25.2}H_{46.4}O_{13.6}Cl_2$ (molecular weight: 637.95)

Analytical Data

| | C | H | Cl |
|---|---|---|---|
| Calculated: | 47.45 | 7.33 | 11.11% |
| Found: | 47.63 | 7.36 | 10.00% |

IR: (film), $\bar{\upsilon}$1802 $cm^{-1}$

EXAMPLE 56

If equimolar amounts of a polyethylene glycol bis (carboxymethyl) ether having an average MW of 250 are used instead of the polyethylene glycol bis(carboxymethyl) ether having an average MW of 600, and the procedure is otherwise as indicated in Example 55, then a polyethylene glycol bis(chlorocarbonylmethyl) ether of the formula indicated in Example 55 is obtained in which m is 2.6 and which has an average MW of 287.

EXAMPLE 57

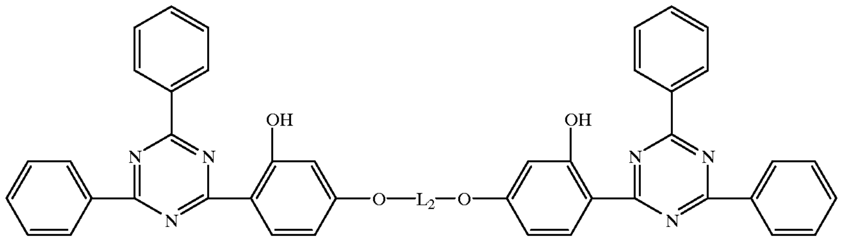

$L_2 = -CH_2-CH(OH)-CH_2-O-(CH_2-CH_2-O)_m-CH_2-CH(OH)-CH_2-$ m = 13.2

The reaction is carried out under a nitrogen atmosphere.

A mixture of 15.0 g (44.0 mmol) of 2,4-diphenyl-6-(2',4'-dihydroxyphenyl)-1,3,5-triazine, 18.0 g (26.0 mmol; 45.0 mmol of epoxide function) of diglycidyl ether of Example 53 (epoxide content: 2.44 mol/kg) and 0.8 g (2.2 mmol) of ethyltriphenylphosphonium bromide (97%, from Fluka) in 75 ml of xylene (isomer mixture from Fluka, ultrapure) is heated at a temperature of about 120° C. for about 20 hours. The yellow suspension becomes a reddish orange solution. The solvent is removed on a rotary evaporator and the crude product is subjected to column chromatography (Ø=9.5 cm; H=25 cm; silica gel 60: 230–400 mesh; eluent:

$CH_2Cl_2$methanol (95:5)). Then the solvent is removed and the product is dried at 150° C./0.1 mm Hg for 2 hours. 15.8 g (51.5% yield) of polyethylene glycol bis[3-(4-(2,4-diphenyl-1,3,5-triazin-6-yl)-3-hydroxyphenyloxy)-2-hydroxypropy]ether of the above formula are obtained as a yellow resin.

Analysis:

Appearance: hard yellow resin (melting point 60.3° C. (DSC))

$^1H$ NMR ($CDCl_3$, 300 MHz): The spectrum is in agreement with the desired product.

Empirical formula: $C_{74.4}H_{92.8}N_6O_{20.2}$ (molecular weight 1394.40)

| | C | H | N |
|---|---|---|---|
| Calculated: | 64.09 | 6.71 | 6.03 |
| Found: | 63.26 | 6.95 | 5.70 |

UV (AcOEt):

ε(max: 341 nm)=41 300

ε(max: 272 nm)=83 420

$^1H$ NMR ($CDCl_3$, 300 MHz): The spectrum is in agreement with the desired product.

Empirical formula: $C_{52}H_{48}N_6O_9$ (molecular weight: 901.00)

| | C | H | N |
|---|---|---|---|
| Calculated: | 69.32 | 5.37 | 9.33 |
| Found: | 68.90 | 5.56 | 9.10 |

UV (AcOEt):

ε(max: 340 nm)=39 980

ε(max: 272 nm)=81 590

EXAMPLE 58

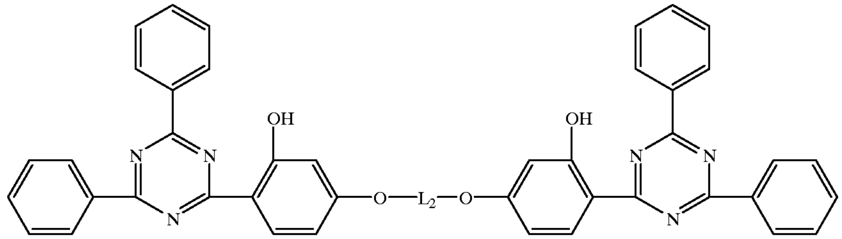

$L_2 = -CH_2-CH(OH)-CH_2-O-(CH_2-CH_2-O)_m-CH_2-CH(OH)-CH_2-$ m = 2

Following the procedure of Example 57 but using, instead of the diglycidyl ether of Example 53, the diglycidyl ether of Example 49, the polyethylene glycol bis[3-(4-(2,4-diphenyl-1,3,5-triazin-6yl)-3-hydroxyphenyloxy)-2-hydroxypropyl) ether of the above formula is obtained as a yellow resinous solid having the following analytical data:

Melting point: 111.5° C. (DSC)

EXAMPLE 59

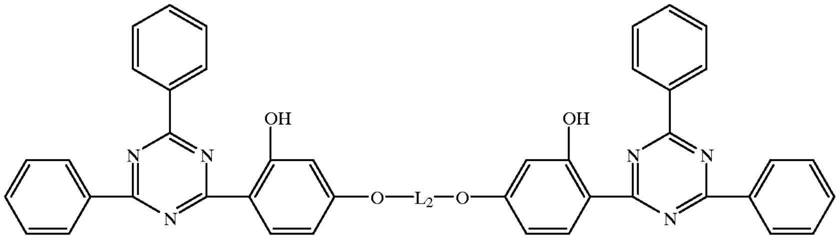

$L_2 = -CH_2-CH(OH)-CH_2-O-(CH_2-CH_2-O)_m-CH_2-CH(OH)-CH_2-$ m =3

Following the procedure of Example 57 but using, instead of the diglycidyl ether of Example 53, the diglycidyl ether of Example 50, the polyethylene glycol bis[3-(4-(2,4-diphenyl-1,3,5-triazin-6-yl-)-3-hydroxyphenyloxy)-2-hydroxypropyl]ether of the above formula is obtained as a hard yellow resin having the following analytical data:

Melting point: 104.3° C. (DSC)

$^1H$ NMR ($CDCl_3$, 300 MHz): The spectrum is in agreement with the desired product.

Empirical formula: $C_{54}H_{52}N_6O_{10}$ (molecular weight: 945.05)

| | C | H | N |
|---|---|---|---|
| Calculated: | 68.63 | 5.55 | 8.89% |
| Found: | 67.08 | 5.70 | 8.31% |

UV (AcOEt):

ε(max: 341 nm)=37 840

ε(max: 283 nm)=61 820

EXAMPLE 60

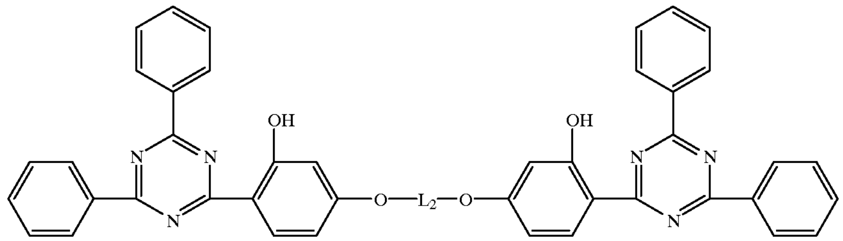

$L_2 = -CH_2-CH(OH)-CH_2-O-(CH_2-CH_2-O)_m-CH_2-CH(OH)-CH_2-$ m = 4

Following the procedure of Example 57 but using, instead of the diglycidyl ether of Example 53, the diglycidyl ether of Example 51, the polyethylene glycol bis[3-(4-(2,4-diphenyl-1,3,5-triazin6-yl-)-3-hydroxyphenyloxy)-2-hydroxypropyl]ether of the above formula is obtained as a yellow resinous solid having the following analytical data:

Melting point: 92.0° C. (DSC)

$^1H$ NMR ($CDCl_3$, 300 MHz): The spectrum is in agreement with the desired product.

Empirical formula: $C_{56}H_{56}N_6O_{11}$ (molecular weight: 989.10)

Analytical Data

| | C | H | N |
|---|---|---|---|
| Calculated: | 68.00 | 5.71 | 8.50% |
| Found: | 66.25 | 6.03 | 7.75% |

UV (AcOEt):

ε(max: 341 nm)=37 920

ε(max: 292 nm)=76 890

EXAMPLE 61

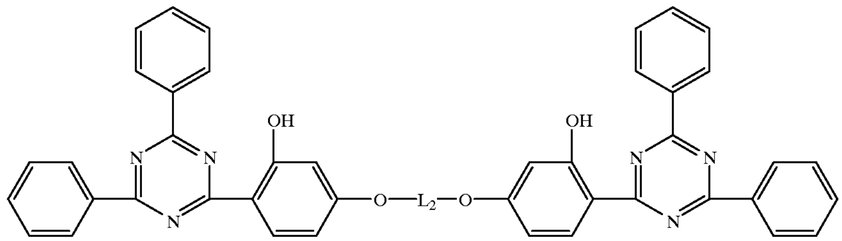

$L_2 = -CH_2-CH(OH)-CH_2-O-(CH_2-CH_2-O)_m-CH_2-CH(OH)-CH_2-$ m = 6.4

Following the procedure of Example 57 but using, instead of the diglycidyl ether of Example 53, the diglycidyl ether of Example 52, polyethylene glycol bis[3-(4-(2,4-diphenyl-1,3,5-triazin-6-yl-)-3-hydroxyphenyloxy)-2-hydroxypropyl] ether of the above formula is obtained as a hard yellow resin having the following analytical data:

Melting point: 84.1° C. (DSC)

$^1H$ NMR ($CDCl_3$, 300 MHz): The spectrum is in agreement with the desired product.

Empirical formula: $C_{60.8}H_{65.5}N_6O_{13.4}$ (molecular weight: 1094.83)

Analytical Data

| | C | H | N |
|---|---|---|---|
| Calculated: | 66.70 | 6.04 | 7.68% |
| Found: | 64.86 | 6.52 | 6.73% |

UV (AcOEt):

ε(max: 340 nm)=39 090

ε(max: 272 nm)=78 360

EXAMPLE 62

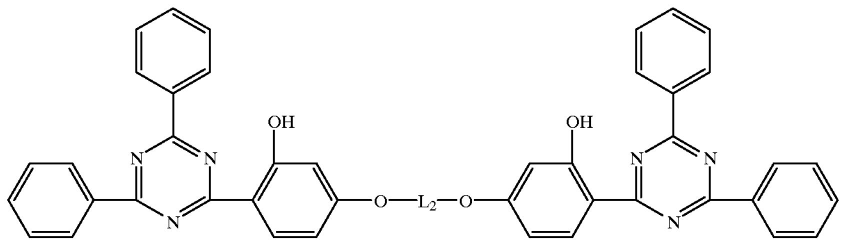

$L_2$ = —$CH_2$—CH(OH)—$CH_2$—O—($CH_2$—$CH_2$—O$)_m$—$CH_2$—CH(OH)—$CH_2$— m = 8.7

Following the procedure of Example 57 but using, instead of the diglycidyl ether of Example 53, the diglycidyl ether of Example 48, the polyethylene glycol bis[3-(4-(2,4-diphenyl-1,3,5-triazin-6-yl-)-3-hydroxyphenyloxy-)-2-hydroxypropyl]ether of the above formula is obtained as a hard yellow resin having the following analytical data:

Melting point: 74.5° C. (DSC)

$^1$H NMR ($CDCl_3$, 300 MHz): The spectrum is in agreement with the desired product.

Empirical formula: $C_{65.4}H_{74.8}N_6O_{15.7}$ (molecular weight: 1196.16)

Analytical Data

| | C | H | N |
|---|---|---|---|
| Calculated: | 65.67 | 6.30 | 7.03% |
| Found: | 64.98 | 6.56 | 6.73% |

UV (AcOEt):

ε(max: 341 nm)=35 940

ε(max: 272 nm)=74 020

EXAMPLE 63

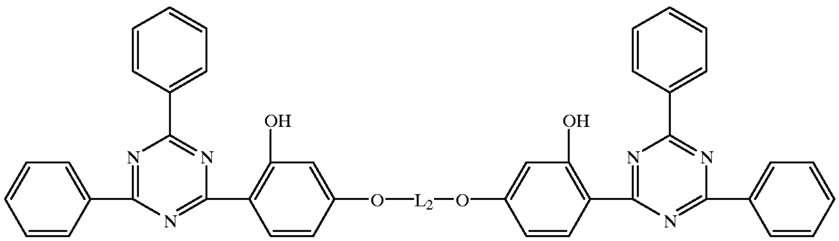

$L_2$ = —$CH_2$—CH(OH)—$CH_2$—O—($CH_2$—$CH_2$—O$)_m$—$CH_2$—CH(OH)—$CH_2$— m = 22.3

Following the procedure of Example 57 but using, instead of the diglycidyl ether of Example 53, the diglycidyl ether of Example 54, the polyethylene glycol bis[3-(4-(2,4-diphenyl-1,3,5-triazin-6-yl-)-3-hydroxyphenyloxy)-2-hydroxypropyl]ether of the above formula is obtained as a yellow resin having the following analytical data:

Melting point: 31.0° C. (DSC)

$^1$H NMR ($CDCl_3$, 300 MHz): The spectrum is in agreement with the desired product.

Empirical formula: $C_{92.6}H_{129.2}N_{29.3}$ (molecular weight: 1795.28)

Analytical Data

| | C | H | N |
|---|---|---|---|
| Calculated: | 61.95 | 7.25 | 4.68 |
| Found: | 60.55 | 7.27 | 4.02 |

UV (AcOEt):

ε(max: 341 nm)=36 900

ε(max: 273 nm)=72 390

EXAMPLE 64

Following the procedure of Example 57 but using, instead of 2,4-diphenyl-6-(2',4'-dihydroxyphenyl)-1,3,5-triazine, equimolar amounts of 2,4-bis(2',4'-dimethylphenyl)-6-(2',4'-dihydroxyphenyl)-1,3,5-triazine and, instead of the diglycidyl ether of Example 53, the diglycidyl ethers listed in Table 6 below, the polyoxyalkylene-bridged bistriazine derivatives indicated in Table 6 are obtained.

EXAMPLE 72

Following the procedure of Example 57 but using, instead of 2,4-diphenyl-6-(2',4'-dihydroxyphenyl)-1,3,5-triazine, equimolar amounts of 2,4-bis(4'-phenyl-p-phenyl)-6-(2',4'-dihydroxyphenyl)-1,3,5-triazine and, instead of the diglycidyl ether of Example 53, the diglycidyl ethers listed in Table 8 below, the polyoxyalkylene-bridged bistriazine derivatives indicated in Table 8 are obtained.

TABLE 6

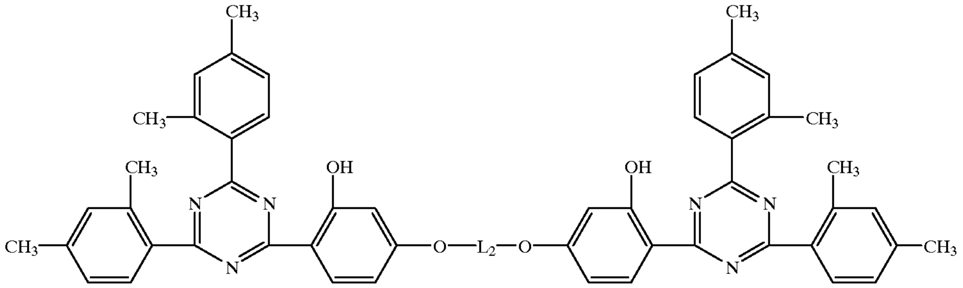

$L_2 = -CH_2-CH(OH)-CH_2-O-(CH_2-CH_2-O-)_m-CH_2-CH(OH)-CH_2-$

| Example | Diglycidyl ether of | m |
|---|---|---|
| 65 | Example 49 | 2 |
| 66 | Example 50 | 3 |
| 67 | Example 51 | 4 |
| 68 | Example 52 | 6.4 |
| 69 | Example 48 | 8.7 |
| 70 | Example 53 | 13.2 |
| 71 | Example 54 | 22.3 |

The physical data of the bistriazine derivatives of Table 6 are set out in Table 7 below:

TABLE 7

| Ex. No. | Appearance | Tg in ° C. (DSC) | Empirical formula (Mol wt.) | C H N in % | UV (acOEt) ε (max: 337 nm) ε (max: 288 nm) |
|---|---|---|---|---|---|
| 65 | hard yellow resin | 32.9 | $C_{60}H_{64}N_6O_9$ (1013.21) | c: 71.13 6.37 8.29<br>f: 71.15 6.73 7.80 | 39 950<br>82 840 |
| 66 | hard yellow resin | 36.2 | $C_{62}H_{68}N_6O_{10}$ (1057.27) | c: 70.44 6.48 7.95<br>f: 70.32 6.54 7.78 | 43 330<br>87 820 |
| 67 | yellow resin | 23 | $C_{64}H_{72}N_6O_{11}$ (1101.32) | c: 69.80 6.59 7.63<br>f: 69.37 6.56 7.21 | 42 830<br>89 916 |
| 68 | brownish orange resin | 10.4 | $C_{68.8}H_{81.6}N_6O_{13.4}$ (1207.05) | c: 68.46 6.81 6.96<br>f: 68.44 6.86 6.90 | 43 795<br>87 400 |
| 69 | brownish orange resin | 2.0 | $C_{73.4}H_{90.8}N_6O_{15.7}$ (1308.37) | c: 67.38 6.99 6.42<br>f: 66.82 7.01 6.35 | 44 250<br>88 360 |
| 70 | brownish orange resin | −17.1 | $C_{82.4}H_{108.8}N_6O_{20.2}$ (1506.61) | c: 65.69 7.28 5.58<br>f: 65.60 7.23 5.68 | 44 720<br>88 670 |
| 71 | non-transparent brownish-orange resin | −37.2 | $C_{100.6}H_{145.2}N_6O_{29.3}$ (1907.50) | c: 63.34 7.67 4.41<br>f: 62.26 8.07 3.93 | 40 690<br>80 575 |

TABLE 8

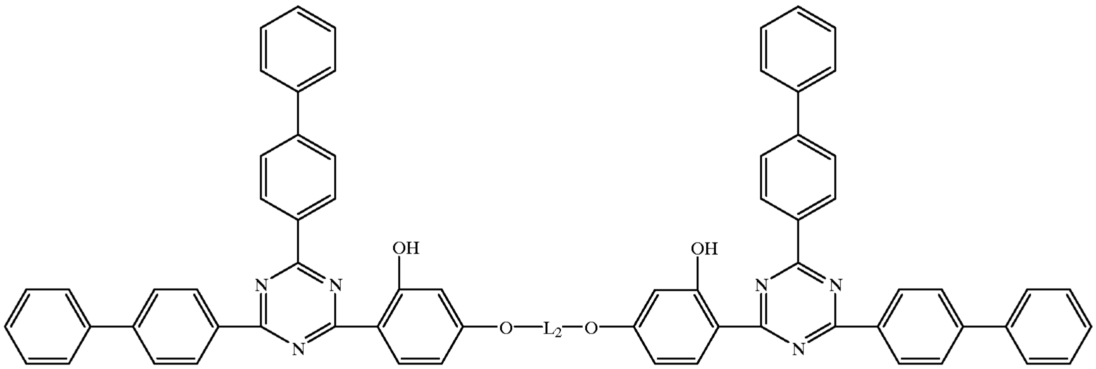

$L_2$ = $-CH_2-CH(OH)-CH_2-O-(CH_2-CH_2-O-)_m-CH_2-CH(OH)-CH_2-$

| Example | Diglycidyl ether of | m |
|---|---|---|
| 73 | Example 49 | 2 |
| 74 | Example 50 | 3 |
| 75 | Example 51 | 4 |
| 76 | Example 52 | 6.4 |
| 77 | Example 48 | 8.7 |
| 78 | Example 53 | 13.2 |
| 79 | Example 54 | 22.3 |

EXAMPLE 80

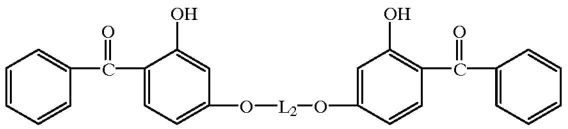

$L_2$ = $-CH_2-CH(OH)-CH_2-O-(CH_2-CH_2-O)_m-CH_2-CH(OH)-CH_2-$
m = 87

The reaction is carried out under a nitrogen atmosphere. A mixture of 20.0 g (93.0 mmol) of 2,4-dihydroxybenzophenone (99%, Fluka), 27.6 g (54.0 mmol; 95.0 mmol of epoxide function), diglycidyl ether of Example 48 (epoxide content: 3,44 mol/kg), 1.7 g (4.7 mmol) of ethyltriphenylphosphonium bromide (Fluka, 97%) in 75 ml of xylene (isomer mixture, ultrapure, Fluka) is heated at a temperature of about 120° C. for 20 hours.

After removing the solvent, a brown resin is obtained which is subjected to column chromatography (Ø=9.5 cm; H=25 cm; silica gel 60, 230–400 mesh; eluent $CH_2Cl_2$/methanol 95:5). The solvent is then removed and the residue is dried at a temperature of 150° C./0.1 mm Hg for 2 hours. 39.0 g (88.7% yield) of polyethylene glycol bis(3-(4-benzoyl-3-hydroxyphenyloxy)-2-hydroxypropyl]ether of the above formula are obtained as a yellow resin which has the following analytical data:

Tg: −21.8° C.

$^1H$ NMR ($CDCl_3$, 300 MHz): The spectrum is in agreement with the desired product.

Empirical formula: $C_{49.4}H_{64.8}O_{17.7}$ (molecular weight: 941.85)

| | C | H |
|---|---|---|
| Calculated: | 63.00 | 6.93% |
| Found: | 62.43 | 6.83% |

UV (AcOEt):

ε(max: 326 nm)=18 800

ε(max: 288 nm)=28 220

EXAMPLE 81

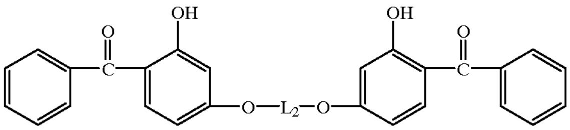

$L_2$ = $-CH_2-CH(OH)-CH_2-O-(CH_2-CH_2-O)_m-CH_2-CH(OH)-CH_2-$
m = 2

Following the procedure of Example 80 but using, instead of the diglycidyl ether of Example 48, the diglycidyl ether of Example 49, the polyethylene glycol bis[3-(4-benzoyl-3-hydroxyphenyloxy)-2-hydroxypropyl]ether of the above formula is obtained as a yellow resin which has the following analytical data:

Tg: 10.0° C.

$^1H$ NMR ($CDCl_3$, 300 MHz): The spectrum is in agreement with the desired product.

Empirical formula: $C_{36}H_{38}O_{11}$ (molecular weight: 646.70)

Analytical Data

| | C | H |
|---|---|---|
| Calculated: | 66.86 | 5.92% |
| Found: | 66.78 | 6.00% |

UV (AcOEt):

ε(max: 325 nm)=19 430

ε(max: 287 nm)=30'30

EXAMPLE 82

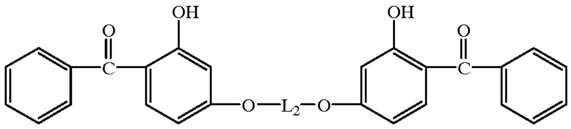

$L_2$ = $-CH_2-CH(OH)-CH_2-O-(CH_2-CH_2-O)_m-CH_2-CH(OH)-CH_2-$
m = 3

Following the procedure of Example 80 but using, instead of the diglycidyl ether of Example 48, the diglycidyl ether of Example 50, the polyethylene glycol bis[3-(4-benzoyl-3-hydroxyphenyloxy)-2-hydroxypropyl]ether of the above formula is obtained as a yellow resin which has the following analytical data:

Tg: −0.2° C.

$^1$H NMR ($CDCl_3$, 300 MHz): The spectrum is in agreement with the desired product.

Empirical formula: $C_{38}H_{42}O_{12}$ (molecular weight: 690.75)

Analytical Data

| | C | H |
|---|---|---|
| Calculated: | 66.08 | 6.13% |
| Found: | 65.07 | 6.39% |

UV (AcOEt):

ε(max: 325 nm)=18 480

ε(max: 287 nm)=28 960

EXAMPLE 83

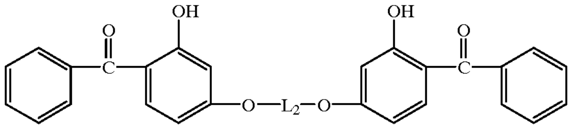

$L_2$ = $-CH_2-CH(OH)-CH_2-O-(CH_2-CH_2-O)_m-CH_2-CH(OH)-CH_2-$
m = 4

Following the procedure of Example 80 but using, instead of the diglycidyl ether of Example 48, the diglycidyl ether of Example 51, the polyethylene glycol bis[3-(4-benzoyl-3-hydroxyphenyloxy)-2-hydroxypropyl]ether of the above formula is obtained in a yellow resin which has the following analytical data:

Tg: −4.3° C.

$^1$H NMR ($CDCl_3$, 300 MHz): The spectrum is in agreement with the desired product.

Empirical formula: $C_{40}H_{46}O_{13}$ (molecular weight: 734.80)

Analytical Data

| | C | H |
|---|---|---|
| Calculated: | 65.38 | 6.31% |
| Found: | 64.95 | 6.52% |

UV (AcOEt):

ε(max: 325 nm)=19 350

ε(max: 288 nm)=29 150

EXAMPLE 84

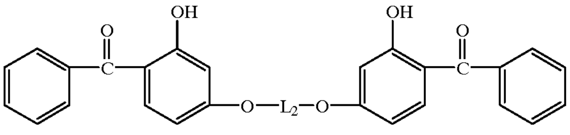

$L_2$ = $-CH_2-CH(OH)-CH_2-O-(CH_2-CH_2-O)_m-CH_2-CH(OH)-CH_2-$
m = 6.4

Following the procedure of Example 80 but using, instead of the diglycidyl ether of Example 48, the diglycidyl ether of Example 52, the polyethylene glycol bis-[3-(4-benzoyl-3-hydroxyphenyloxy)-2-hydroxypropyl]ether of the above formula is obtained as an orange-coloured resin which has the following analytical data:

Tg: −16.7° C.

$^1$H NMR ($CDCl_3$, 300 MHz): The spectrum is in agreement with the desired product.

Empirical formula: $C_{44.8}H_{55.6}O_{15.4}$ (molecular weight: 840.53)

Analytical Data

| | C | H |
|---|---|---|
| Calculated: | 64.02 | 6.67% |
| Found: | 62.43 | 6.91% |

UV (AcOEt):

ε(max: 326 nm)=17'900

ε(max: 288 nm)=26'760

EXAMPLE 85

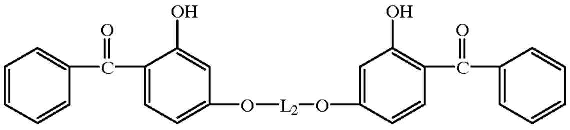

$L_2$ = $-CH_2-CH(OH)-CH_2-O-(CH_2-CH_2-O)_m-CH_2-CH(OH)-CH_2-$
m = 13.2

Following the procedure of Example 80 but using, instead of the diglycidyl ether of Example 48, the diglycidyl ether of Example 53, the polyethylene glycol bis[3-(4-benzoyl-3-hydroxyphenyloxy)-2-hydroxypropyl]ether of the above formula is obtained as a yellow resin which has the following analytical data:

Tg: −30.2° C.

$^1$H NMR ($CDCl_3$, 300 MHz): The spectrum is in agreement with the desired product.

Empirical formula: $C_{58.4}H_{82.8}O_{22.2}$ (molecular weight: 1140.09)

Analytical Data

| | C | H |
|---|---|---|
| Calculated: | 61.53 | 7.32% |
| Found: | 61.22 | 7.44% |

UV (AcOEt):

ε(max: 325 nm)=19 160

ε(max: 288 nm)=28 380

EXAMPLE 86

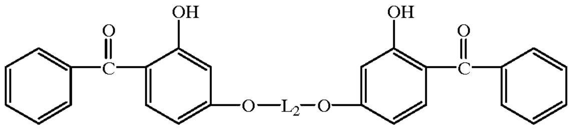

$L_2$ = $-CH_2-CH(OH)-CH_2-O-(CH_2-CH_2-O)_m-CH_2-CH(OH)-CH_2-$ m = 22.3

Following the procedure of Example 80 but using, instead of the diglycidyl ether of Example 48, the diglycidyl ether of Example 54, the polyethylene glycol bis[3-(4-benzoyl-3-hydroxyphenyloxy)-2-hydroxypropyl] ether of the above formula is obtained.

EXAMPLE 87

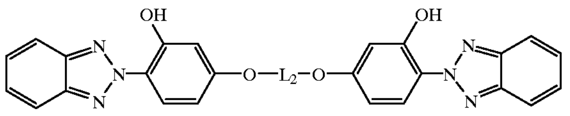

$L_2$ = $-CH_2-CH(OH)-CH_2-O-(CH_2-CH_2-O)_m-CH_2-CH(OH)-CH_2-$ m = 2

The reaction is carried out under a nitrogen atmosphere.

A mixture of 2-(2',4'-dihydroxyphenyl)-1,2,3-benzo(2H) triazole, diglycidyl ether of Example 49 and ethyltriphenylphosphonium bromide in xylene is heated for about 20 hours at a temperature of about 120° C. The solvent is removed on a rotary evaporator and the crude product is subjected to column chromatography (Ø=9.5 cm; H=25 cm; silica gel 60; 230–400 mesh; eluent: $CH_2Cl_2$/methanol (95:5)). Then the solvent is removed and the product is dried. The compound of the above formula is obtained.

EXAMPLE 88

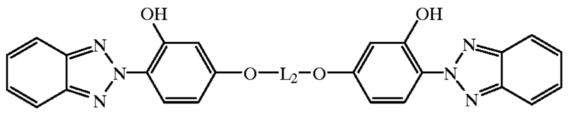

$L_2$ = $-CH_2-CH(OH)-CH_2-O-(CH_2-CH_2-O)_m-CH_2-CH(OH)-CH_2-$ m =4

Following the procedure of Example 87 but using, instead of the diglycidyl ether of Example 49, equimolecular amounts of the diglycidyl ether of Example 51, the polyoxyalkylene-bridged bisbenzotriazole compound of the above formula is obtained.

EXAMPLE 89

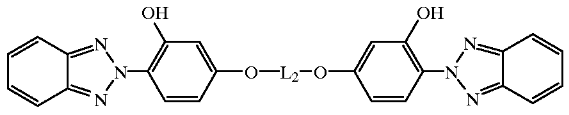

$L_2$ = $-CH_2-CH(OH)-CH_2-O-(CH_2-CH_2-O)_m-CH_2-CH(OH)-CH_2-$ m = 8.7

Following the procedure of Example 87 but using, instead of the diglycidyl ether of Example 49, equimolecular amounts of the diglycidyl ether of Example 48, the polyoxyalkylene-bridged bisbenzotriazole compound of the above formula is obtained.

EXAMPLE 90

Polytetrahydrofuran α,ω-diglycidyl ether 361

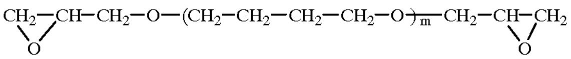

m =3,2

The reaction is carried out under a nitrogen atmosphere.

To a stirred solution of 125.0 g (0.50 mol) of polytetrahydrofuran 250 (Terathan® 250) (average molecular weight=250) (Aldrich), 1.0 g (0.003 mol) of tetra-n-butylammonium bromide (FLUKA, 99%) and 231.3 g (2.5 mol) of epichlorohydrin (FLUKA, 99.5%) there are added, in portions over the course of 15 minutes, 48.0 g (1.20 mol) of pulverized sodium hydroxide (FLUKA, 98%). An exothermic reaction is observed and the temperature is held at 30–40° C. by occasional cooling. After stirring for 2 hours more at 25° C., the solid is filtered off and pressed dry. The filtrate is evaporated at 70° C./15 mm Hg and then at 80° C./0.7 mm Hg (rotary evaporator) in order to remove excess epichlorohydrin and water. 155.7 g (86.1% yield) of polytetrahydrofuran α,ω)-diglycidyl ether 361 (molecular weight 360.89) are obtained as a pale yellow liquid.

Analysis:

Appearance: pale yellow oil

$^1$H NMR ($CDCl_3$, 300 MHz): The spectrum is in agreement with the desired product.

Empirical formula: $C_{18.8}H_{35.6}O_{6.2}$ (molecular weight: 360.89)

Analytical Data

| | C | H |
|---|---|---|
| Calculated: | 62.57 | 9.94% |
| Found: | 61.49 | 10.07% |

Epoxide content:

Calculated: 5.54 mol/kg

Found: 4.59 mol/kg

EXAMPLE 91

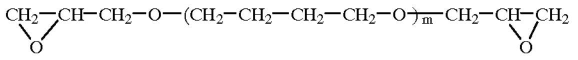

m =8.8

Following the procedure of Example 90 but using, instead of polytetrahydrofuran 250, polytetrahydrofuran 650 (Terathan® 650, Aldrich, a Dupont product) (average molecular weight 650), the polytetrahydrofuran α,ω-diglycidyl ether 765 of the above constitution (average molecular weight 764.69) is obtained.

Analysis:

Appearance: pale yellow oil $^1$H NMR ($CDCl_3$, 300 MHz): The spectrum is in agreement with the desired product.

Empirical formula: $C_{41.2}H_{80.4}O_{11.8}$ (molecular weight 764.69)

Analytical Data

| | C | H |
|---|---|---|
| Calculated: | 64.71 | 10.60% |
| Found: | 64.57 | 10.76% |

Epoxide content:

Calculated: 2.62 mol/kg

Found: 2.19 mol/kg

EXAMPLE 92

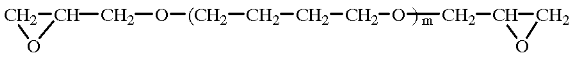

m = 13.6 m=13.6

Following the procedure of Example 90 but using, instead of the polytetrahydrofuran (m=3.2), a polytetrahydrofuran where m=13.6, the diglycidyl ether of the above formula is obtained.

Analysis:

$^1$H NMR ($CDCl_3$, 300 MHz): The spectrum is in agreement with the desired product.

Empirical formula: $C_{60.4}H_{118.8}O_{16.6}$ (molecular weight: 1110.80)

EXAMPLE 93

The procedure of Examples 57 and 64 and 72 but using, instead of the diglycidyl ether of example 53, equimolar amounts of the diglycidyl ether of Example 90, and of Example 91, and 92, respectively, the polyoxyalkylene-bridged bistriazine derivatives according to Table 9 are obtained.

TABLE 9

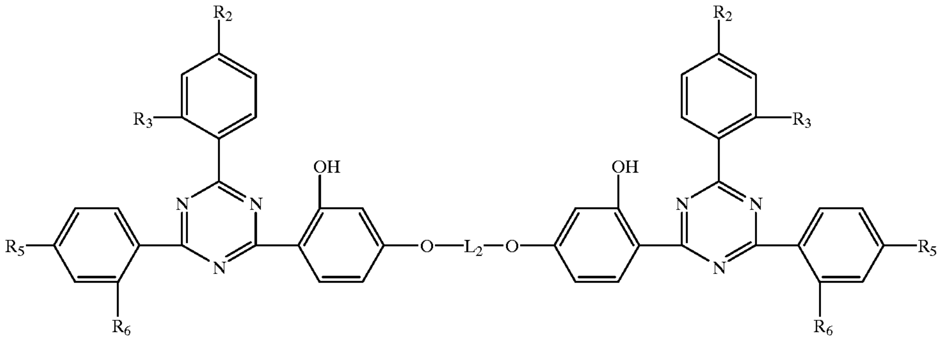

$L_2$ = $-CH_2-CH(OH)-CH_2-O-(CH_2-CH_2-CH_2-CH_2-O-)_m-CH_2-CH(OH)-CH_2-$

| Example No. | $R_2$ | $R_3$ | $R_5$ | $R_6$ | m |
|---|---|---|---|---|---|
| 94 | H | H | H | H | 3.2 |
| 95 | H | H | H | H | 8.8 |
| 96 | H | H | H | H | 13.6 |
| 97 | $CH_3$ | $CH_3$ | $CH_3$ | $CH_3$ | 3.2 |
| 98 | $CH_3$ | $CH_3$ | $CH_3$ | $CH_3$ | 8.8 |
| 99 | $CH_3$ | $CH_3$ | $CH_3$ | $CH_3$ | 13.6 |
| 100 | Phenyl | H | Phenyl | H | 3.2 |
| 101 | Phenyl | H | Phenyl | H | 8.8 |
| 102 | Phenyl | H | Phenyl | H | 13.6 |

Compound No. 97 ($C_{68.8}H_{81.6}N_6O_{10.2}$; 1155.85 g/mol) is a yellow resin with UV maxima ($CHCl_3$) at 337 nm (ε=43 600) and 291 nm (ε=86 300). Compound No. 98 ($C_{91.2}H_{126.4}N_6O_{15.8}$; 1559.65 g/mol) is a clear resin with UV maxima (AcOET) at 336 nm (ε=49 200) and 291 nm (ε=96 640).

EXAMPLE 103

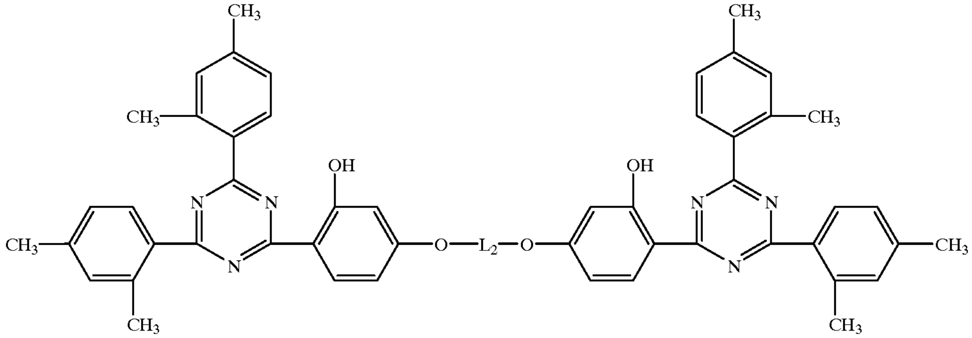

$L_2 = -CO-CH_2-O-(CH_2-CH_2-O)_m-CH_2-CO-$ m = 10.6

The reaction is carried out under a nitrogen atmosphere.

4.4 g (55.0 mmol) of pyridine (99.8%, Fluka) are added at a temperature of about 54° C. to a solution of 19.9 g (50.0 mmol) of 2,4-bis(2',4'-dimethylphenyl)-6-(2',4'-dihydroxyphenyl)-1,3,5-triazine in 100 ml of diethylene glycol dimethyl ether (diglyme 99.5%, Fluka). This pale red solution is treated by dropwise addition, with stirring, of 19.1 g (30.0 mmol) of polyethylene glycol bis (chlorocarbonylmethyl) ether (average molecular weight 638) of Example 55. The solution turns pale yellow and a solid is deposited.

The mixture is stirred and heated at a temperature of about 70° C. for 14 hours. After cooling, the solid is filtered off and the product is subjected to column chromatography (silica gel 60, 230–400 mesh; Ø=7 cm; H=32 cm; eluent toluenel-methanol 9:1).

Following removal of the solvent and drying at 80° C./0.1 mm Hg for 2 hours, the main fraction yields 22.3 g (65.6% yield) of polyethylene glycol bis[(4-(2,4-bis(2',4'-dimethylphenyl)-1,3,5-triazin-6-yl)-3-hydroxyphenyloxycarbonylmethyl]ether of the above formula as an orange-brown resin which has the following analytical data:

Softening point: −20.9° C. (DSC)

$^1$H NMR ($CDCl_3$, 300 MHz): The spectrum is in agreement with the desired product.

Empirical formula: $C_{75.2}H_{90.4}N_6O_{17.6}$ (molecular weight: 1359.98)

Analytical Data

| | C | H | N |
|---|---|---|---|
| Calculated: | 66.41 | 6.70 | 6.18% |
| Found: | 65.27 | 6.88 | 5.51% |

UV (AcOEt):

ε(shoulder: 341 nm)=22 430

ε(max: 281 nm)=84 960

Following the procedure of Example 103 but using, instead of the polyethylene glycol bis (chlorocarbonylmethyl) ether with an average molecular weight of 638, one with an average molecular weight of 250 as in Example 56, a polyoxyalkylene-bridged bistriazine derivative of the above formula in which m=2.63 is obtained.

EXAMPLE 104

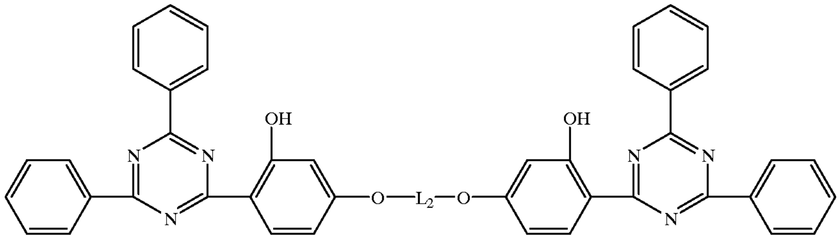

$L_2 = -CO-CH_2-O-(CH_2-CH_2-O)_m-CH_2-CO-$ m = 10.6 and 2.63

Following the procedure of Example 103 but using, instead of 2,4-bis(2',4'-dimethylphenyl)-6-(2',4'-dihydroxyphenyl)-1,3,5-triazine, equimolecular amounts of 2,4-bis(phenyl)-6-(2',4'-dihydroxyphenyl)-1,3,5-triazine, a polyoxyalkylene-bridged bistriazine derivative of the above formula is obtained in which m=10.6 and 2.63 respectively.

EXAMPLE 105

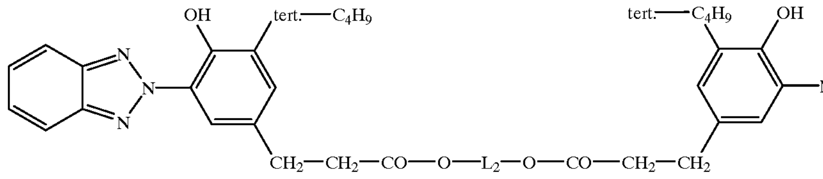

$L_2 = -CH_2-CH(OH)-CH_2-O-(CH_2-CH_2-O)_m-CH_2-CH(OH)-CH_2-$ m = 2

The reaction is carried out under a nitrogen atmosphere. A mixture of 3-(3'-(2"H-benzotriazol-2"-yl)-4'-hydroxy-5'-tert-butylphenyl)propionic acid, diglycidyl ether of Example 49 and ethyltriphenylphosphonium bromide in xylene is heated for about 20 hours at a temperature of about 120° C. The solvent is removed on a rotary evaporator and the crude product is subjected to column chromatography (Ø=9.5 cm; H=25 cm; silica gel 60; 230–400 mesh; eluent: $CH_2Cl_2$/methanol (95:5)). Then the solvent is removed and the product is dried at 150° C./0.1 mm Hg for 2 hours. The polyoxyalkylene-bridged bis-1,2,3-triazole compound of the above formula is obtained.

EXAMPLE 106

Triethylene glycol α,ω-bis[3-(2'-(3"-(2H-benzotriazol-2-yl)-4"-hydroxy-5"-tert-butylphenyl) ethylcarbonyloxy)-2-hydroxypropyl]ether The reaction is carried out under a nitrogen atmosphere. A mixture of 33.9 g (0.100 mol) of 3-(3'-(2"H-benzotriazol-2"-yl)-4'-hydroxy-5'-tert-butylphenyl) propionic acid, 15.1 g (0.058 mol; 0.091 mol of epoxide function) of triethylene glycol α,ω-diglycidyl ether (Example 50) and 2.9 g (0.008 mol) of ethyltriphenylphosphonium bromide (FLUKA, 97%) in 50 ml of xylene (isomer mixture, FLUKA) is heated with stirring for 24 hours at a temperature of 140° C. After cooling, the solvent is removed by evaporation (rotary evaporator). The crude material, a viscous residue, is subjected to column chromatography (500 g of silica gel 60; 230–400 mesh; Ø=6 cm; H=50 cm) eluent: ethyl acetate). After removal of the solvent and drying, 9.9 g of an unreacted reactant is obtained as a first eluted compound.

In a second eluted fraction, 7.0 g of triethylene glycol α,ω-bis[3-(2'-(3"-(2H-benzotriazol-2-yl)-4"-hydroxy-5"-tert-butylphenyl)ethylcarbonyloxy)-2-hydroxypropyl]ether are obtained as a yellow, nontransparent resin which has the following analytical data:

Appearance: yellow, nontransparent resin;

Tg=18.9° C. (DSC)

$^1H$ NMR ($CDCl_3$, 300 MHz): The spectrum is in agreement with the desired product.

Empirical formula: $C_{50}H_{64}N_6O_{12}$

Molecular weight: 941.10

| | C % | H % | N % |
|---|---|---|---|
| Calculated: | 63.81 | 6.85 | 8.93% |
| Found: | 63.97 | 6.81 | 8.76% |

UV (AcOEt):

ε(max: 342 nm)=31 690

ε(max: 301 nm)=32 080

Following the procedure of Example 106 but using, instead of the diglycidyl ether mentioned, one according to Examples 52, 48 and 53, the polyoxyalkylene-bridged bis-triazole derivatives evident from Table 10 are obtained.

TABLE 10

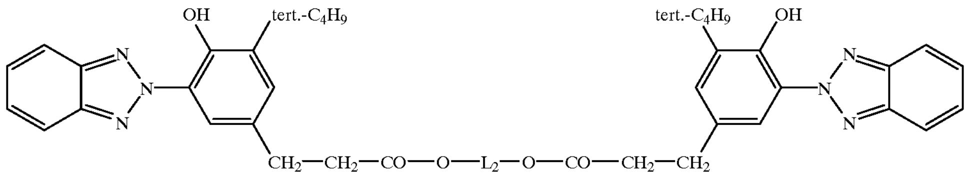

$L_2 = -CH_2-CH(OH)-CH_2-O-(CH_2-CH_2-O-)_m-CH_2-CH(OH)-CH_2-$

| Example | Diglycidyl ether of | m |
|---|---|---|
| 107 | Example 52 | 6.4 |
| 108 | Example 48 | 8.7 |
| 109 | Example 53 | 13.2 |

EXAMPLE 110

Following the procedure of Example 105 but using, instead of 3-(3'-(2"H-benzotriazol-2"-yl)-hydroxy-5'-tert-butylphenyl)propionic acid, equimolar amounts of 3-(3'-(5"-chloro-2"H-benzotriazol-2"-yl)-4'-hydroxy-5'-tert-butylphenyl)propionic acid, the compound of the formula

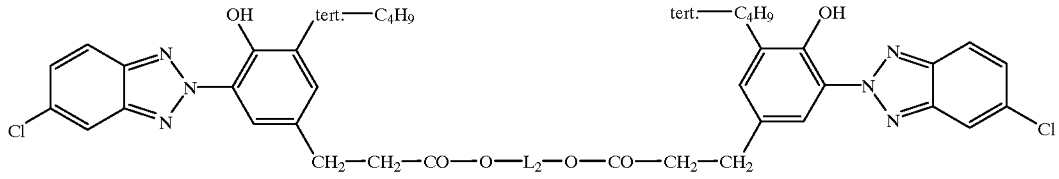

$L_2$ = —$CH_2$—CH(OH)—$CH_2$—O—($CH_2$—$CH_2$—O$)_m$—$CH_2$—CH(OH)—$CH_2$— m = 2 is obtained.

After cooling, the solid is filtered off and the product is subjected to column chromatography (silica gel 60, 230–400 mesh; Ø=7 cm; H=32 cm); eluent toluene/methanol (9:1). After removal of the solvent and drying at 80° C./0.1 mm Hg for 2 hours, the main fraction yields the compound of the above formula.

EXAMPLE 112

Following the procedure of Example 110 but using a diglycidyl ether of Example 51 or 52 or 48 or 53, compounds are obtained which are illustrated in Table 11.

Following the procedure of Example 116 but using, instead of the polyethylene glycol bis(chlorocarbonylmethyl) ether having an average molecular weight of 638, one having an average molecular weight of 250 as in Example 56, a polyoxyalkylene-bridged bistriazole derivative of the above formula is obtained in which m2.63.

TABLE 11

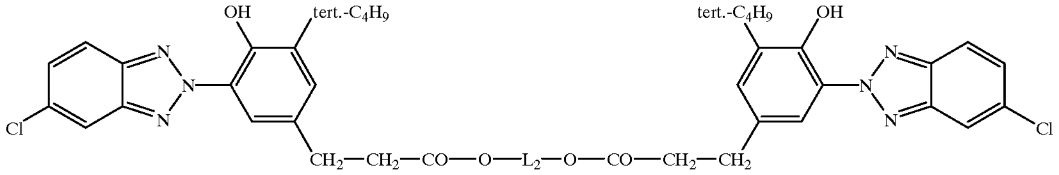

$L_2$ = —$CH_2$—CH(OH)—$CH_2$—O—($CH_2$—$CH_2$—O—$)_m$—$CH_2$—CH(OH)—$CH_2$—

| Example No. | m |
|---|---|
| 112 | 4 |
| 113 | 6.4 |
| 114 | 8.7 |
| 115 | 13.2 |

EXAMPLE 116

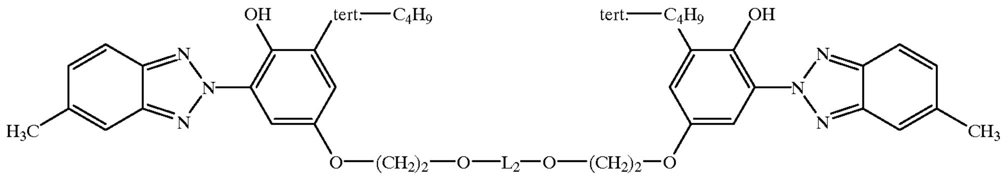

$L_2$ = —CO—$CH_2$—O—($CH_2$—$CH_2$—O$)_m$—$CH_2$—CO— m = 10.6

The reaction is carried out under a nitrogen atmosphere. Pyridine (99.8%, Fluka) is added at a temperature of about 54° C. to a solution of 6-tert-butyl-4-(2'-hydroxyethoxy)-2-(5"-methyl-2'H-benzotriazol-2"-yl) phenol in diethylene glycol dimethyl ether (99.5%, Fluka). To this solution is added dropwise with stirring the polyethylene glycol bis(chlorocarbonylmethyl) ether (average molecular weight 638) of Example 55. The mixture is stirred and heated for 14 hours at a temperature of about 70° C.

EXAMPLE 117a 2.4-Bis(2',4'-dimethylphenyl)-6-(2'-hydroxa-4'-(1"-(ethoxycarbonyl)ethoxy)phenyl)-1,3,5-triazine To a mixture of 37.9 g (0.100 mol) of 2,4-bis(2',4'-dimethylphenyl)-6-(2',4'-dihydroxyphenyl)-1,3,5-triazine, 14.5 g ( 0.105 mol) of potassium carbonate (Fluka, 99.0%) in 250 ml of N,N-dimethylformamide (DMF, Fluka, 99.5%) there are added dropwise with stirring at 80° C. 19.0 g (0.105 mol) of ethyl 2-bromopropionate (Fluka, 98%). The mixture is held at 80° C. for 1 h, then poured into 4 l of cold water and subjected to extraction with 2 l of ethyl acetate. The organic phase is filtered and washed with 2×500 ml of water and dried ($MgSO_4$). Removal of the solvent and drying at 60° C./60 mmHg/24 h give 39.0 g of 2,4-bis(2',4'-dimethylphenyl)-6-(2'-hydroxy-4'-(1"-(ethoxycarbonyl)ethoxy)phenyl)-1,3,5-triazine as pale yellow crystals of m.p. 120–122° C.

EXAMPLE 117b

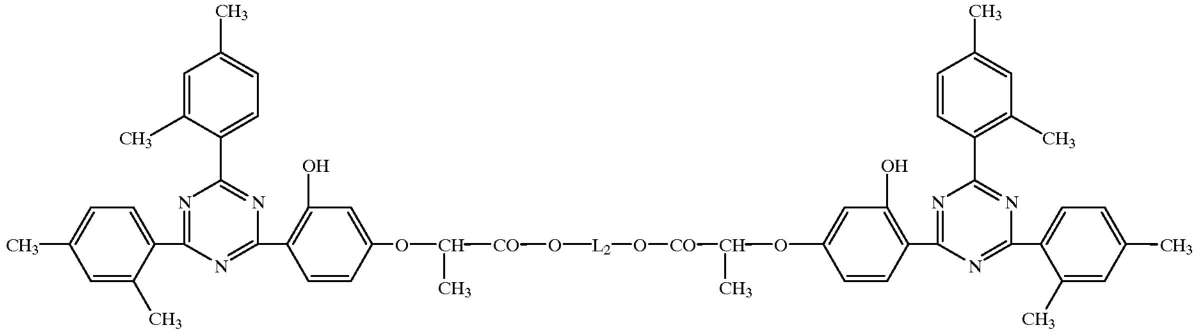

$L_2$ = $—(CH_2—CH_2—O)_m—CH_2—CH_2—$
m = 3

A mixture of 49.7 g (0.100 mol) of 2,4-bis(2',4'-dimethylphenyl-)-6-(2"-hydroxy-4"-(1'"-(ethoxycarbonyl)ethoxy)phenyl)-1,3,5-triazine (compound from Example 117a), 9.7 (50 mmol) of tetraethylene glycol and 0.65 g (3 mmol) of dibutyltin oxide is heated to 150° C. with stirring under inert gas ($N_2$) in a reactor fitted with a Claisen condenser. 50 ml of toluene are added dropwise over 2 hours, after which the reaction mixture is held 150' C. for a further 5 h 30 min. Then a further 100 ml of toluene are added, the reaction mixture is cooled and concentrated on a rotary evaporator, and the residue is placed on a silica gel column (Ø=7 cm, H=50 cm, silica gel 60, 230–400 mesh). Elution is carried out with petroleum ether/ethyl acetate (9:1). After stripping off the solvent and drying the residue (50° C./60.1 mm Hg/24 h), 22.6 g of the title product are obtained; m.p. 68–72° C.

EXAMPLE 118

Following the procedure of Example 117 but using, instead of tetraethylene glycol, eqimolecular amounts of the polyethylene glycol as indicated in Table 12, the bistriazine derivatives listed in Table 12 are obtained.

TABLE 12

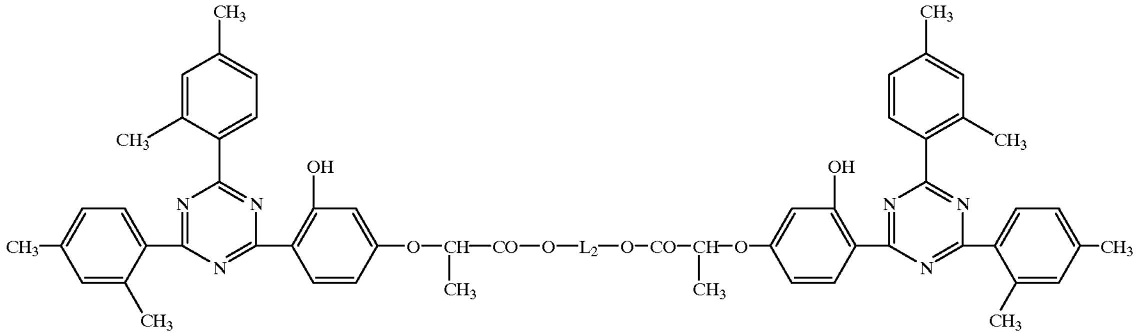

| Example No. | $L_2$ = $—(CH_2—CH_2—O—)_m—CH_2—CH_2—$ m | Polyethylene glycol |
|---|---|---|
| 119 | 5.4 | Polyethylene glycol 300 |
| 120 | 7.7 | Polyethylene glycol 400 |
| 121 | 12.2 | Polyethylene glycol 600 |
| 122 | 21.3 | Polyethylene glycol 1000 |

EXAMPLE 123

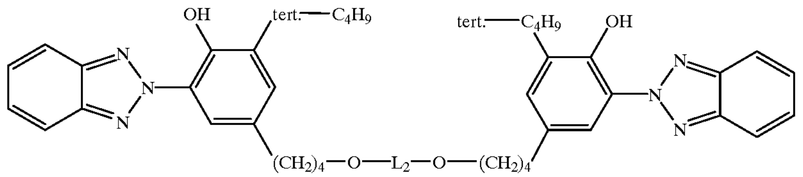

$L_2 = -CO-CH_2-O-(CH_2-CH_2-O)_m-CH_2-CO-$
m = 2.6

$L_2=-CO-CH_2-O-(CH_2-CH_2-O-)_m-CH_2-CO-$ m=2.6 reaction is carried out under a nitrogen atmosphere.

Pyridine (99.8%, Fluka) is added at a temperature of about 54° C. to a solution of 4-[3'-tert-yl-4'-hydroxy-5'-(2"H-benzotriazol-2"-yl)phenyl]butanol in diethylene glycol dimethyl ether (diglyme 99.5% Fluka). Polyethylene glycol bis(chlorocarbonylmethyl) ether with an average molecular weight of 287 (Example 56) is then added dropwise with stirring. The mixture is stirred and heated at a temperature of about 70° C. for 14 hours. After cooling, the solid is filtered off and the product is subjected to column chromatography (silica gel 60, 230–400 mesh, Ø=7 cm, H=32 cm; eluent toluene/methanol (9:1)). Following removal of the solvent and drying, the main fraction yields the bistriazole compound of the above formula.

EXAMPLE 124

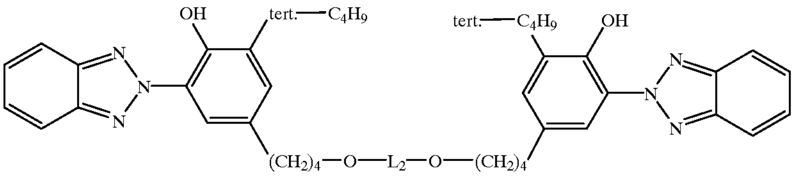

$L_2 = -CO-CH_2-O-(CH_2-CH_2-O)_m-CH_2-CO-$
m = 10.6

Following the procedure of Example 123 but using a polyethylene glycol bis(chlorocarbonylmethyl) ether with an average molecular weight of 638 (Example 55), the bistriazole compound of the formula is obtained.

EXAMPLE 125

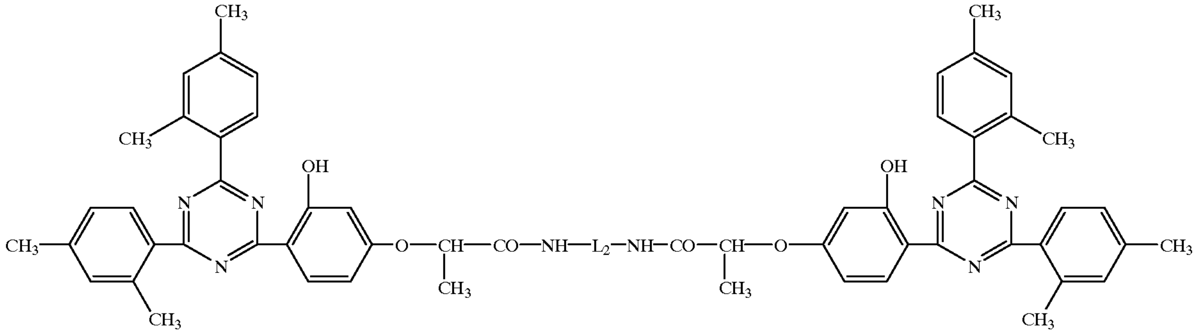

$L_2 = -(CH_2-CH_2-O)_m-CH_2-CH_2-$
m = 2

By reacting 2 mol of a triazine derivative of the formula

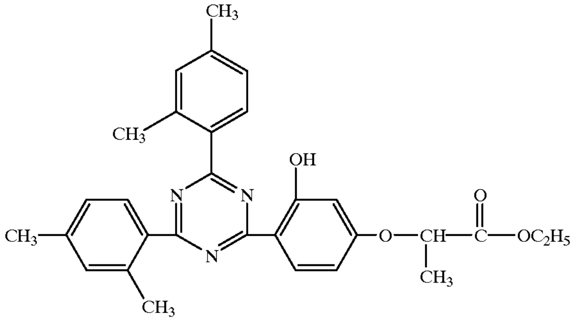

with 1 mol of a diamine (Jeffamine® EDR series) of the formula $NH_2-(CH_2-CH_2-O-)_m-CH_2-CH_2-NH_2$ (m=2)

in the presence of lithium amide as catalyst, amidation gives the polyoxyalkylene-bridged bistriazine compound of the above formula.

By proceeding analogously and using a diamine (Jeffamine® EDR series) of the stated formula where m=3, the bistriazine compound of the formula given at the outset, in which m=3, is obtained.

EXAMPLE 126

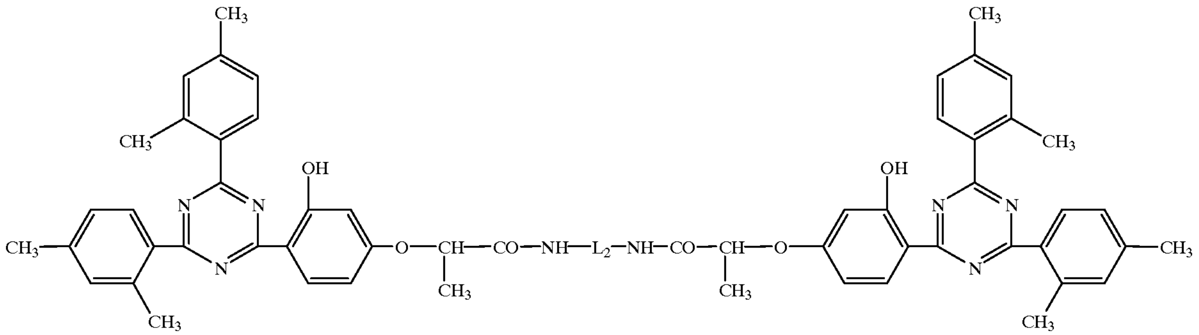

$L_2$ = 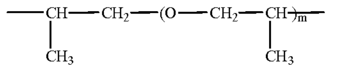

m = 2.7

Following the procedure of Example 125 but using as diamine one of the formula

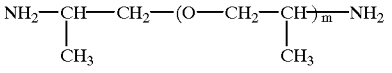

(m=5.6; Jeffamine® D series)

or an analogous diamine where m=33.2, polyoxyalkylene-bridged bistriazine compounds of the above formula are obtained in which m=5.6 or 33.2, respectively.

EXAMPLE 127

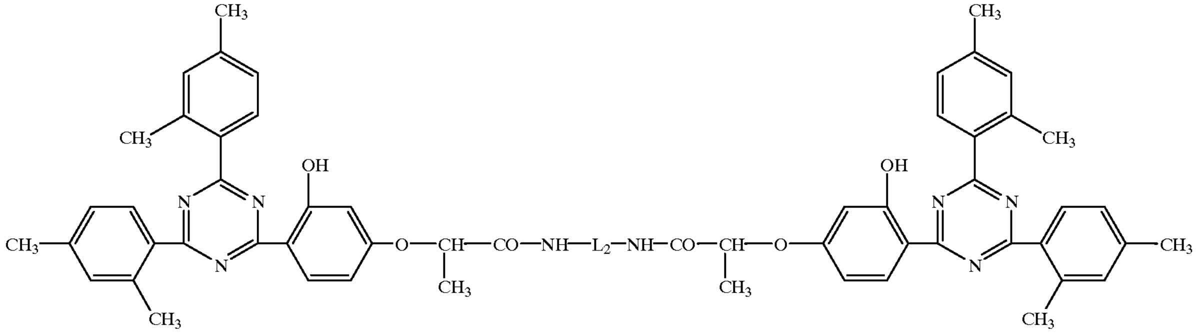

-continued $L_2$ = 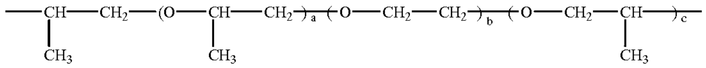

Following the procedure of Example 125 but using as diamine one as indicated in Table 13, polyoxyalkylene-bridged bistriazine compounds of the above formula are obtained in which the symbols a), b) and c) have the values indicated in Table 13.

TABLE 13

| Diamine (Jeffamine ® ED series) | | |
|---|---|---|
| 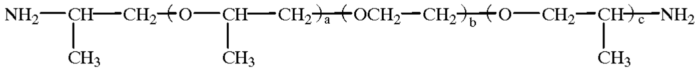 | | |
| Example | approximate value of: | |
| No. | a + c | b |
| 128 | 2.5 | 8.5 |
| 129 | 2.5 | 15.5 |
| 130 | 2.5 | 40.5 |

EXAMPLE 131

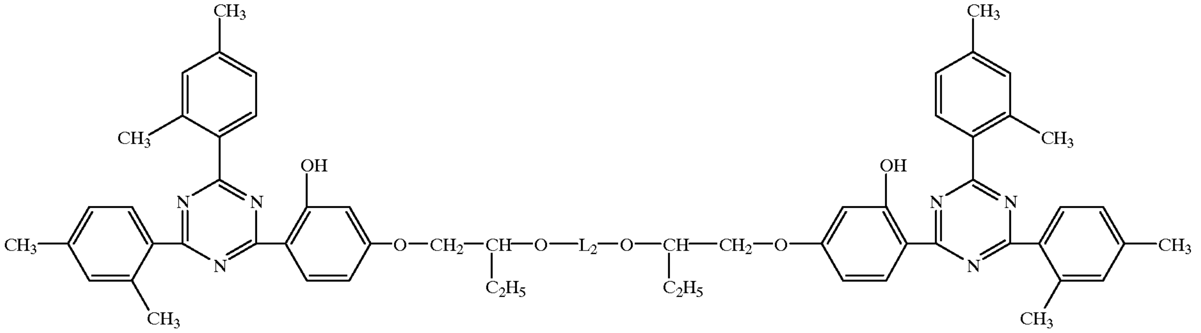

$L_2$ = 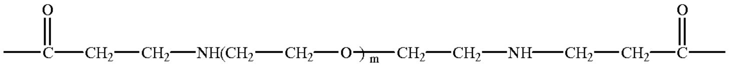

m = 2

By reacting 2 mol of a triazine derivative of the formula

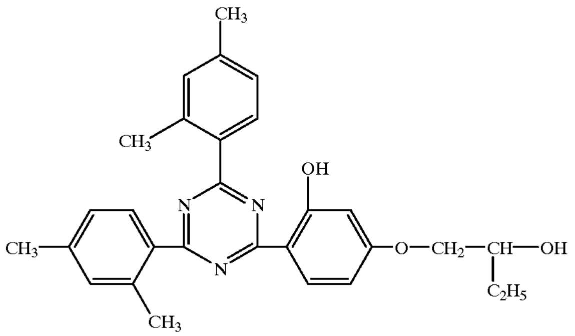

(from the corresponding 2,4-dihydroxytriazine derivative reacted with butylene oxide) with 1 mol of the diester of the formula $C_2H_5OOC—CH_2—CH_2—NH(CH_2—CH_2—O—)_m—CH_2—CH_2—NH—CH_2—CH_2COOC_2H_5$ m=2

(obtained from ethyl acrylate and the diamine of the formula $NH_2—(CH_2—CH_2—O—)_m—CH_2—CH_2—NH_2$ (Jeffamine® D series)) in the presence of dibutyltin oxide as catalyst, the polyoxyalkylene-bridged bistriazine derivative of the above formula is obtained.

EXAMPLE 132

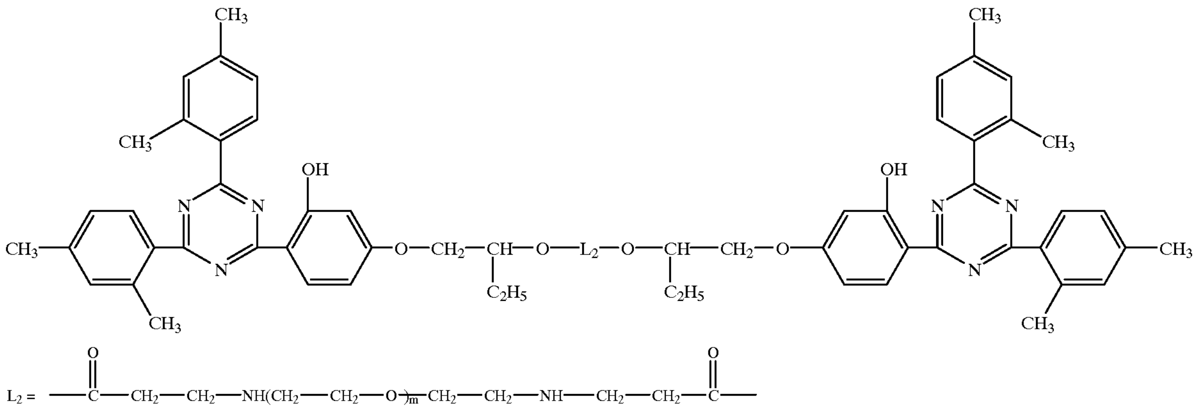

m = 3

Following the procedure of Example 131 but using, instead of the diester indicated therein where m=2, equimolecular amounts of the analogous diester where m=3, the compound of the above formula is obtained.

EXAMPLE 133

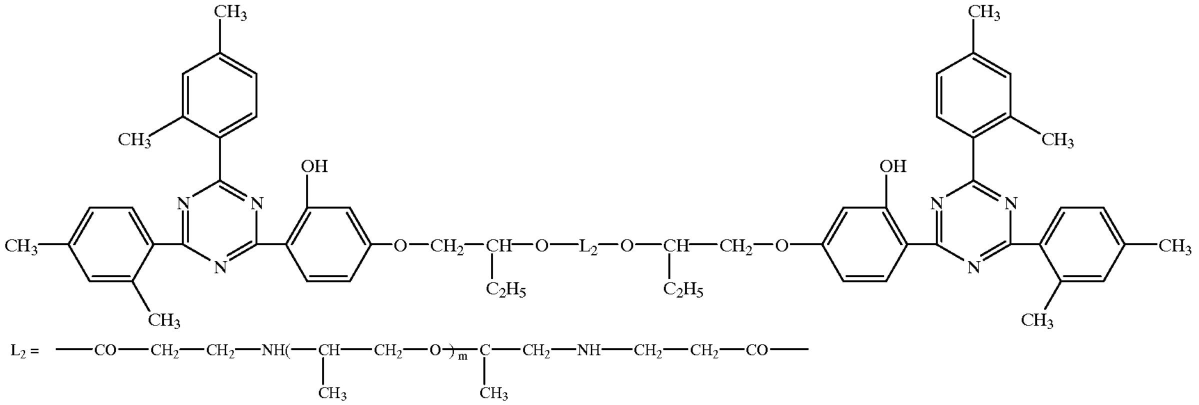

m = 2.7

Following the procedure of Example 131 but using, instead of the diester indicated therein, eqimolecular amounts of the diester of the formula

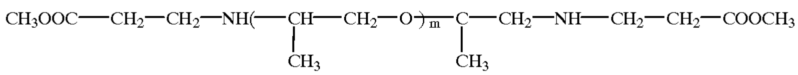

m = 2.7

(Jeffamine® D series), the polyoxyalkylene-bridged bistriazine derivative of the above formula is obtained.

Following the procedure indicated above but using eqimolecular amounts of analogous diesters where m=5.6 or m=33.2, the bistriazine derivatives of the above formula in which m=5.6 or m=33.2, respectively, are obtained.

EXAMPLE 134

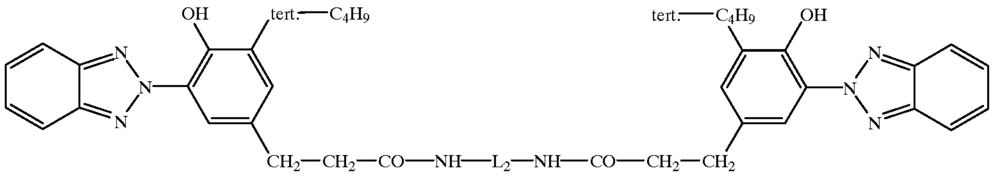

By reacting 2 mol of a benzotriazole derivative of the formula

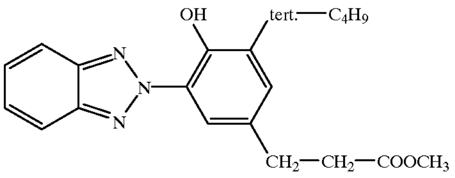

with 1 mol of a diamine $H_2N\text{-}L_2\text{-}NH_2$ in accordance with Table 14 below in the presence of lithium amide as catalyst, amidation gives the polyoxyalkylene-bridged bistriazole compound of the above formula.

TABLE 14

| Example No. | Diamine $H_2N—L_2—NH_2$ | |
|---|---|---|
| | $L_2$ = —$(CH_2—CH_2—O—)_m$—$CH_2—CH_2$— (Type: Jeffamine ® EDR series) | |
| 135 | m = 2 | |
| 136 | m = 3 | |
| | $L_2$ = —$CH(CH_3)—CH_2(O—CH_2—CH(CH_3))_m$— (Type: Jeffamine ® D series) | |
| 137 | m = 2.7 | |
| 138 | m = 5.6 | |
| 139 | m = 33.2 | |
| | $L_2$ = —$CH(CH_3)—CH_2(O—CH(CH_3)—CH_2)_a$—(O—$CH_2—CH_2)_b$—(O—$CH_2—CH(CH_3))_c$— (Type: Jeffamine ® ED series) | |
| 140 | a + c = ~ 2.5; | b = ~ 8.5 |
| 141 | a + c = ~ 2.5; | b = ~ 15.5 |
| 142 | a + c = ~ 2.5; | b = ~ 40.5 |

EXAMPLE 143

(Application Example): Stabilizing a 2-coat Metallic Coating Material

The novel, polyoxyalkylene substituted and bridged triazine, benzotriazole and benzophenone derivatives are dissolved in 20–50 g of Solvesso® and tested in a clearcoat of the following composition:

| | |
|---|---|
| Synthacryl ® SC 303[1)] | 27.51 |
| Synthacryl ® SC 370[2)] | 23.34 |
| Maprenal ® MF 650[3)] | 27.29 |
| Butyl acetate/Butanol (37/8) | 4.33 |
| Isobutanol | 4.87 |
| Solvesso ® 100[4)] | 2.72 |
| Kristallöl K-30[5)] | 8.74 |
| Levelling assistant Baysilon ® MA[6)] | 1.20 |
| | 100.00 g |

[1)]Acrylate resin from Hoechst AG; 65% solution in xylene/butanol 26:9
[2)]Acrylate resin from Hoechst AG; 75% solution in Solvesso ® 100[4)]
[3)]Melamine resin from Hoechst AG; 55% solution in isobutanol
[4)]Aromatic hydrocarbon mixture, boiling range 182–203° C. (Solvesso ® 150) or 161–178° C. (Solvesso ® 100); (manufacturer: Esso)
[5)]Aliphatic hydrocarbon mixture: boiling range 145–200° C.; (manufacturer: Shell)
[6)]1% in Solvesso ® 150[4)]; (manufacturer: Bayer AG)

1.5% of the novel compounds, based on the solids content of the coating material, are added to the clearcoat. In addition to the novel compounds 0.7% or 1% of a costabilizer A (mixture of 80% by weight of a compound of the formula

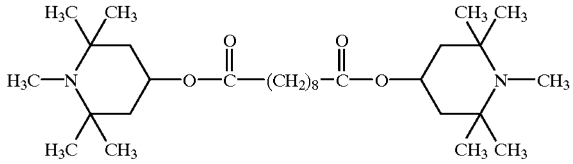

and 20% by weight of its monoester) is added to a number of additional samples; amounts are based in each case on the solids content of the coating material. A clearcoat prepared in the same way but containing no novel compound is used for comparison.

The clearcoat is diluted to spray viscosity with Solvesso® 100 and applied by spraying to a prepared aluminium panel (coil coat, filler, silber-metallic basecoat) and is stoved at 130° C. for 30 minutes, to give a dry film thickness of 40–50 μm of clearcoat.

The samples are then weathered in an UVCON® weathering apparatus (from Atlas Corporation; UVB-313 lamps) with a cycle of 8 hours of UV radiation at 70° C. and 4 hours of condensation at 50° C.

The surface gloss (20° gloss in accordance with DIN 67530) of the samples is measured at regular intervals. The results are illustrated in Tables 15 to 18 below.

TABLE 15

20° gloss, cracking after x hours of weathering in the UVCON (UVB-313)

| 1.5% bistriazine | Cracking after x hours | x hours | | | | |
|---|---|---|---|---|---|---|
| compound of: | x = | x = 0 | 800 | 1600 | 2000 | 2400 |
| Unstabilized | 1200 | 91 | 50 | | | |
| Example 61 | 1600 | 92 | 92 | | | |
| Example 60 | 2400 | 92 | 92 | 90 | 87 | 43 |
| Example 62 | 2400 | 92 | 91 | 86 | 86 | 48 |
| Example 57 | 2400 | 92 | 90 | 89 | 82 | 42 |
| Example 63 | 2400 | 92 | 92 | 89 | 80 | 44 |

TABLE 16

20° gloss, cracking after x hours of weathering in the UVCON (UVB-313)
Combination of the novel stabilizer with 0.7% of costabilizer A

| 1.5% bistriazine | Cracking after x hours | x hours | | | | |
|---|---|---|---|---|---|---|
| compound of: | x = | x = 0 | 1200 | 2800 | 3200 | 3600 |
| Unstabilized | 1200 | 91 | 4 | | | |
| Example 61 | 3600 | 92 | 90 | 89 | 64 | 29 |
| Example 60 | 3600 | 92 | 89 | 89 | 52 | 31 |
| Example 62 | 3200 | 92 | 82 | | | |
| Example 57 | 2800 | 92 | 82 | | | |
| Example 63 | 2800 | 92 | 86 | | | |

TABLE 17

20° gloss, cracking after x hours of weathering in the UVCON (UVB-313)

| 1,5% bisbenzophenone | Cracking after x hours | x hours | | | | |
|---|---|---|---|---|---|---|
| compound of: | x = | x = 0 | 800 | 1600 | 2000 | 2400 |
| Unstabilized | 1600 | 91 | 87 | 15 | | |
| Example 81 | 2400 | 91 | 91 | 89 | 61 | 7 |

TABLE 18

20° gloss, cracking after x hours of weathering in the UVCON (UVB-313)
Combination of the novel stabilizer with 1.0% of costabilizer A

| 1,5% bisbenzophenone | Cracking after x Stunden | x hours | | | | |
|---|---|---|---|---|---|---|
| compound of: | x = | x = 0 | 1200 | 2000 | 2400 | 2800 |
| Unstabilized | 1600 | 91 | 70 | | | |
| Example 81 | 3200 | 91 | 91 | 89 | 89 | 81 |

As evident from the results of Tables 15–18, the samples comprising the novel compounds have better weathering stability (gloss retention, crack resistance) than the comparison sample containing no novel compound (unstabilized).

What is claimed is:

1. A compound of formula II $$A_1—L_2—A_1 \quad (II)$$

in which $A_1$ is a radical of formula VA (VA)

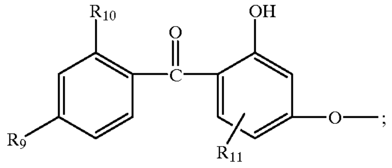

$B_1$ is a bridge member —O— or —NH—, $L_2$ is a polyoxyalkylene bridge member of formula XIV $$—CH_2—CH(OH)—CH_2—O—[CH_2—(CH_2)_u—O—]_m—CH_2—CH(OH)—CH_2— \quad (XIV)$$

or is a polyoxyalkylene bridge member of formula XV $$—CO—(CH_2)_u—O—[CH_2—(CH_2)_u—O—]_m—(CH_2)_u—CO— \quad (XV)$$

or is a polyoxyalkylene bridge member of formula XVI $$—Y—O—CO(CH_2)_u—O—[CH_2—(CH_2)_u—O—]_m—(CH_2)_u—COO—Y— \quad (XVI)$$

or is a polyoxyalkylene bridge member of formula XVII $$—(CH_2)_k—CH(R_{12})—CO—B_1—(C_nH_{2n}—O—)_m—C_nH_{2n}—B_1—CO—CH(R_{12})—(CH_2)_k— \quad (XVII)$$

or is a polyoxyalkylene bridge member of formula XVIII $$—CO—CH(R_{21})—CH_2—NH—(C_nH_{2n}—O—)_m—C_nH_{2n}—NH—CH_2—CH(R_{21})—CO— \quad (XVIII)$$

or is a polyoxyalkylene bridge member of formula XIX $$—Y—O—CO—(CH_2)_2—NH—(C_nH_{2n}—O—)_m—C_nH_{2n}—NH—(CH_2)_2—COO—Y— \quad (XIX)$$

or is a polyoxyalkylene bridge member of formula XXI $$—CH(CH_3)—CH_2—[O—CH(CH_3)—CH_2]_a—(O—CH_2CH_2)_b—(O—CH_2—CH(CH_3)_c)— \quad (XXI)$$

in which a+c=2.5 and b=8.5 to 40.5;

$R_9$ is hydrogen, halogen, $C_1$–$C_{18}$alkoxy, $C_3$–$C_6$alkenoxy or aryl-S(O)$_t$;

$R_{10}$ is hydrogen or OH;

$R_{11}$ is hydrogen, $C_1$–$C_{12}$alkyl, aryl-$C_1$–$C_4$alkyl or $C_3$–$C_6$alkenyl;

$R_{12}$ is hydrogen or $C_1$–$C_{16}$alkyl;

$R_{21}$ is hydrogen, $C_1$–$C_4$alkyl or —CN;

Y is unsubstituted or substituted $C_2$–$C_{20}$alkylene;

k is zero or a number from 1–16;

m is a number from 2–60;

n is a number from 2–6;

t is zero, 1 or 2; and u is a number from 1–4.

2. A compound according to claim 1 in which $R_9$ is hydrogen, halogen, $C_1$–$C_{18}$alkoxy or phenyl-S(O)$_t$;

$R_{10}$ is hydrogen or OH;

$R_{11}$ is hydrogen, $C_1$–$C_8$alkyl, phenyl-$C_1$–$C_3$alkyl or allyl;

$R_{12}$ is $C_1$–$C_{10}$alkyl;

$R_{21}$ is hydrogen or methyl;

Y is unsubstituted or substituted $C_2$–$C_{12}$alkylene;

k is zero or a number from 1–6;

m is a number from 2–50;

n is a number from 2–4;

t is zero, 1 or 2; and u is a number from 1–3.

3. A compound according to claim 1 in which $R_9$ is hydrogen, chlorine, methoxy or phenyl-S(O)$_t$;

$R_{10}$ is hydrogen;

$R_{11}$ is hydrogen, $C_1$–$C_8$alkyl or phenyl-$C_1$–$C_3$alkyl;

$R_{12}$ is $C_1$–$C_{10}$alkyl;

m is a number from 2–23; and n is a number 2 or 3.

4. A compound according to claim 2 in which $L_2$ is a bridge member of one of formulae XIV, XV, XVII, XVIII or XXI.

5. A compound according to claim 1 in which $B_1$ is —O— or —NH—;

$L_2$ is a polyoxyalkylene bridge member of formula XIV, XV, XVII, XVIII or XXI;

$R_9$, $R_{10}$ and $R_{11}$ are each hydrogen;

$R_{12}$ is hydrogen or methyl;

$R_{21}$ is hydrogen;

Y is $C_3$–$C_6$alkylene;

k is zero or 1;

m is a number from 2–23;

n is 2 or 3; and u is 1 to 3.

6. A compound according to claim 1 of formula $VA_2$ ($VA_2$)

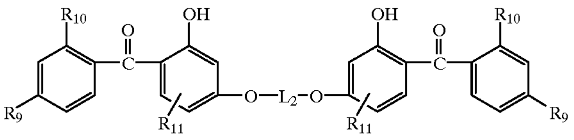

in which $R_9$, $R_{10}$, $R_{11}$ and $L_2$ are described in claim 1.

7. A compound of formula $VA_2$ according to claim 1 wherein $R_9$, $R_{10}$ and $R_{11}$ are each hydrogen, and $L_2$ is a polyoxyalkylene bridge member of formula XIV wherein u is 1, and m is 2, 3, 4, 6.4, 13.2, 22.3 or 87.

* * * * *